(12) United States Patent
Marks et al.

(10) Patent No.: US 9,387,065 B2
(45) Date of Patent: Jul. 12, 2016

(54) IMPLANT AND FILAMENT MANAGEMENT DEVICE

(71) Applicant: Medos International Sàrl, Le Locle (CH)

(72) Inventors: Jacob A. Marks, Foxboro, MA (US); Meghan A. Pasquali, Providence, RI (US); Danielle Dufour, Franklin, MA (US)

(73) Assignee: MEDOS INTERNATIONAL SÀRL, Le Locle (CH)

(*) Notice: Subject to any disclaimer, the term of this patent is extended or adjusted under 35 U.S.C. 154(b) by 188 days.

(21) Appl. No.: 14/229,498

(22) Filed: Mar. 28, 2014

(65) Prior Publication Data
US 2015/0272721 A1 Oct. 1, 2015

(51) Int. Cl.
*A61F 2/08* (2006.01)
*A61B 17/04* (2006.01)
*A61F 2/00* (2006.01)

(52) U.S. Cl.
CPC ........... *A61F 2/0811* (2013.01); *A61B 17/0401* (2013.01); *A61F 2/0095* (2013.01); *A61F 2/0805* (2013.01); *A61F 2/08* (2013.01); *A61F 2002/0817* (2013.01); *A61F 2240/002* (2013.01); *A61F 2240/005* (2013.01); *A61F 2250/0097* (2013.01)

(58) Field of Classification Search
USPC ........................................................ 606/148
See application file for complete search history.

(56) References Cited

U.S. PATENT DOCUMENTS

| 3,939,969 | A | 2/1976 | Miller et al. |
| 4,483,437 | A | 11/1984 | Cerwin et al. |
| 4,491,218 | A | 1/1985 | Aday |
| 4,496,045 | A | 1/1985 | Ferguson et al. |
| 4,615,435 | A | 10/1986 | Alpern et al. |
| 4,782,954 | A | 11/1988 | Reynolds |

(Continued)

FOREIGN PATENT DOCUMENTS

| EP | 0 579 377 A2 | 1/1994 |
| FR | 2 814 359 A1 | 3/2002 |
| FR | 2 873 567 A1 | 2/2006 |

OTHER PUBLICATIONS

Extended European Search Report for EP Application No. 15161442.7, issued Jul. 8, 2015. (7 pages).

(Continued)

*Primary Examiner* — Thomas J Sweet
*Assistant Examiner* — Wade P Schutte

(57) ABSTRACT

A variety of configurations of implant management devices are provided. The configurations provide different combinations of features for maintaining a location of an implant with respect to the device and managing filaments of the implant. One exemplary embodiment of a device includes a generally rectangular-shaped body having an implantable body retainer, an opening disposed a distance apart from the retainer and configured to receive a ligament graft therein, and a fold extending across the body and intersecting the opening. Folding one end of the body towards a bottom surface of the body along the fold can form a filament loop engaging region to hold in tension a filament loop extending from the implant. Additional filament(s) associated with the implant can be managed by various filament retention features. Methods for preparing a ligament graft for implantation by relying upon indicia formed on a surface of the device body are also provided.

7 Claims, 33 Drawing Sheets

(56) References Cited

U.S. PATENT DOCUMENTS

| | | |
|---|---|---|
| 4,884,681 A | 12/1989 | Roshdy et al. |
| 5,048,678 A | 9/1991 | Chambers |
| 5,092,455 A | 3/1992 | Leary |
| 5,121,836 A | 6/1992 | Brown et al. |
| 5,169,041 A | 12/1992 | Tan |
| 5,174,087 A | 12/1992 | Bruno |
| 5,197,597 A | 3/1993 | Leary et al. |
| 5,199,561 A | 4/1993 | Roshdy et al. |
| 5,226,535 A | 7/1993 | Rosdhy et al. |
| 5,271,494 A | 12/1993 | Odermatt et al. |
| 5,298,012 A | 3/1994 | Handlos |
| 5,358,624 A | 10/1994 | Roshdy et al. |
| 5,425,445 A | 6/1995 | Brown et al. |
| 5,487,469 A | 1/1996 | Roshdy et al. |
| 5,529,175 A | 6/1996 | Brunken |
| 5,566,821 A | 10/1996 | Brown et al. |
| 5,566,822 A | 10/1996 | Scanlon |
| 5,669,490 A | 9/1997 | Colligan et al. |
| 5,715,942 A | 2/1998 | Li et al. |
| 5,733,293 A | 3/1998 | Scirica et al. |
| 5,788,062 A | 8/1998 | Cerwin et al. |
| 5,788,063 A | 8/1998 | Van Ness |
| 6,047,815 A | 4/2000 | Cerwin et al. |
| 6,080,184 A | 6/2000 | Peters et al. |
| 6,260,696 B1 | 7/2001 | Braginsky et al. |
| 6,796,977 B2 | 9/2004 | Yap et al. |
| 7,600,634 B2 | 10/2009 | Malinowski et al. |
| 7,611,008 B2 | 11/2009 | Ruffieux et al. |
| 8,307,978 B2 | 11/2012 | Kirsch et al. |
| 8,460,317 B2 | 6/2013 | Merves |
| 9,028,547 B2 | 5/2015 | Lebeau et al. |
| 2002/0040240 A1 | 4/2002 | Heckele et al. |
| 2003/0065247 A1 | 4/2003 | Yap et al. |
| 2005/0065533 A1 | 3/2005 | Magen et al. |
| 2005/0241961 A1 | 11/2005 | Ferguson |
| 2007/0162125 A1 | 7/2007 | LeBeau et al. |
| 2007/0270857 A1 | 11/2007 | Lombardo et al. |
| 2009/0112053 A1 | 4/2009 | Viitala et al. |
| 2010/0018164 A1 | 1/2010 | Malinowski et al. |
| 2010/0044262 A1 | 2/2010 | Malinowski et al. |
| 2012/0330323 A1* | 12/2012 | Lizardi ............ A61B 19/46 606/102 |
| 2014/0074239 A1 | 3/2014 | Albertorio et al. |
| 2014/0094912 A1 | 4/2014 | Walker |
| 2014/0214163 A1 | 7/2014 | Demmer et al. |
| 2014/0257346 A1 | 9/2014 | Sengun et al. |
| 2015/0012094 A1 | 1/2015 | Denham et al. |
| 2015/0157449 A1 | 6/2015 | Gustafson et al. |
| 2015/0272720 A1 | 10/2015 | Marks et al. |

OTHER PUBLICATIONS

Extended European Search Report for EP Application No. 15161474.0, issued Aug. 5, 2015. (7 pages).

* cited by examiner

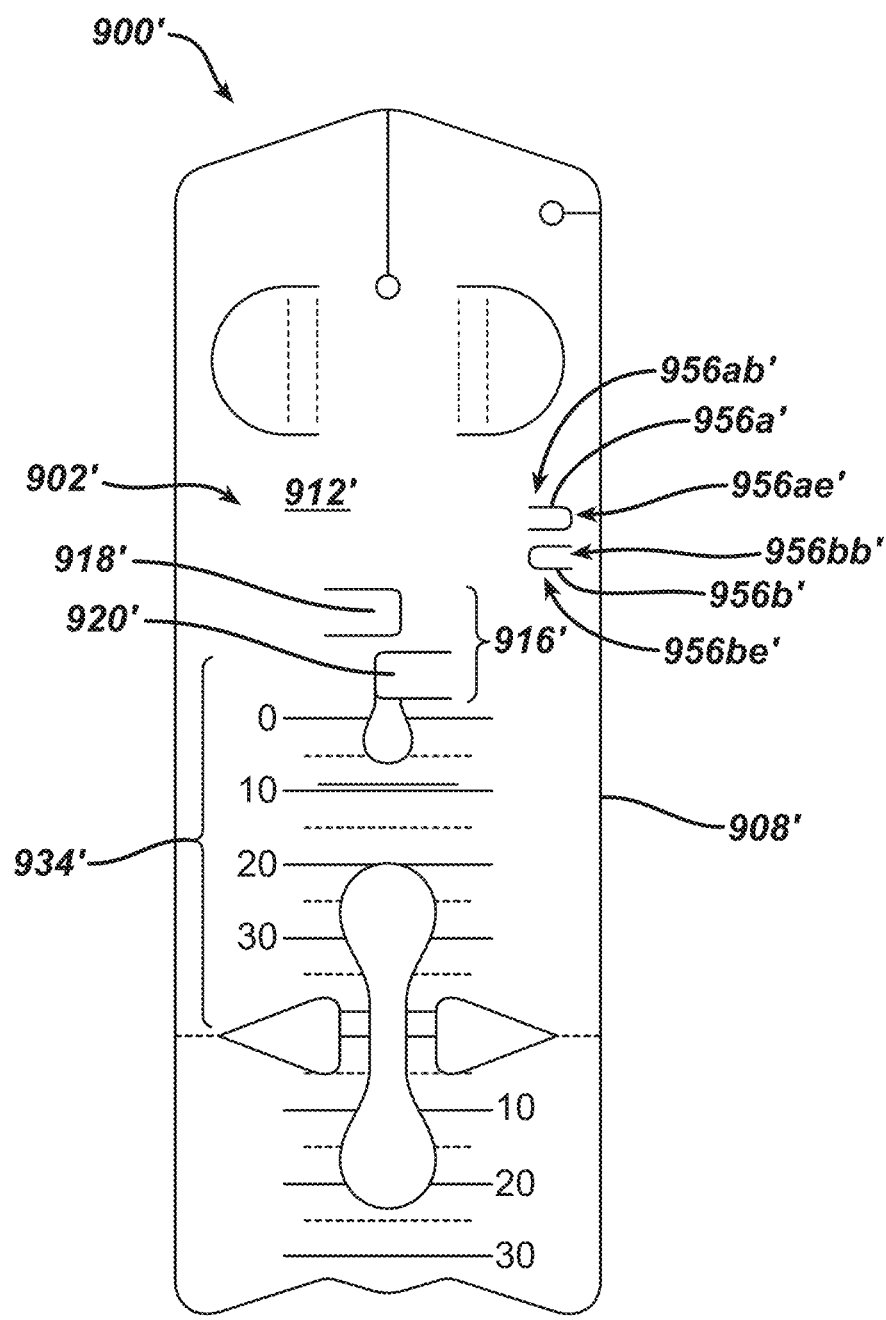

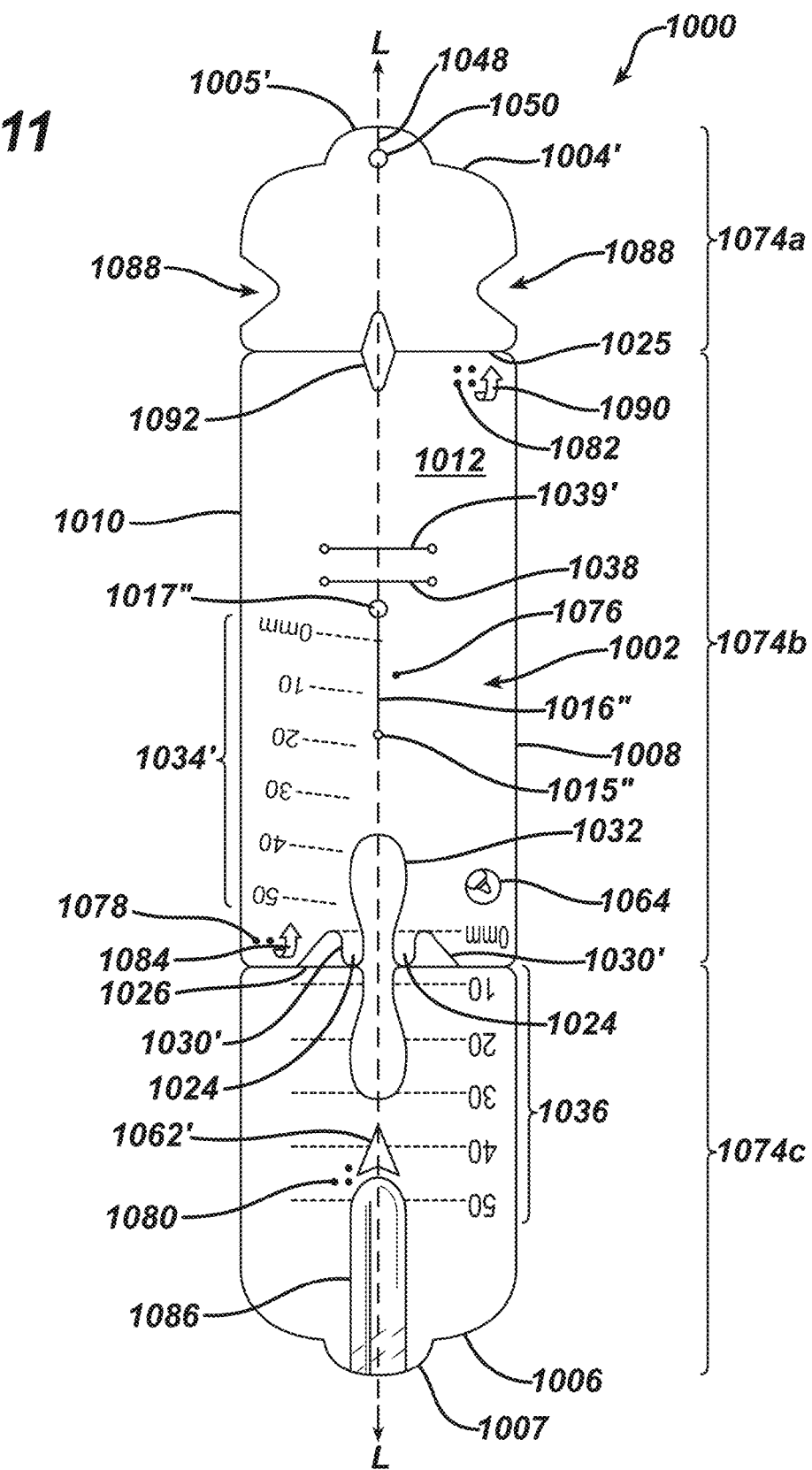

IMPLANT AND FILAMENT MANAGEMENT DEVICE

FIELD

The present disclosure relates to devices and methods for managing surgical implants having one or more surgical filaments associated therewith, and more particularly relates to storage cards or devices that can be used to hold the implant in preparation for surgical procedures.

BACKGROUND

Joint injuries may commonly result in the complete or partial detachment of ligaments, tendons, and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves forming aligned femoral and tibial tunnels in a knee to repair a damaged anterior cruciate ligament ("ACL"). In one ACL repair procedure, a ligament graft is associated with a surgical implant and secured to the femur. A common ACL femoral fixation means includes an elongate "button," sometimes referred to as a cortical button. The cortical button is attached to a filament loop that is sized to allow an adequate length of a soft tissue graft to lie within the femoral tunnel while providing secure extra-cortical fixation. A size of the filament loop can be adjusted by filament limbs extending therefrom. Further, the cortical button can have one or more additional filaments or sutures coupled thereto for purposes of guiding and positioning the implant and ligament graft to desired locations in the body during the surgical procedure.

While the inclusion of filament limbs and additional filaments for positioning the implant can be useful for the procedure, it can be difficult to manage the various filaments both prior to and during a surgical procedure. For instance, prior to a surgical procedure, it can be difficult to package the implant in an efficient manner while limiting the likelihood of filament becoming intertwined with itself and/or other filament associated with the implant. The possibility of filament becoming intertwined once the implant is removed from the initial packaging can also cause difficulties. For example, a location at which a ligament graft is to be associated with the implant may be difficult to discern due to intertwined filament. As a result, a user may associate a ligament graft with an incorrect filament, or portion thereof (e.g., not all of the loops when an implant includes multiple filament loops), which can lead to premature failure of the implant or other undesirable outcomes. Further, even in use during the procedure, it can be difficult to keep track of the various filaments, which can lead to user error in which a surgeon thinks he or she is pulling one filament for a particular purpose but instead pulls another that serves a different purpose.

Still further, misuse of the implant can occur due to a user not knowing where within the body the implant is located. It can be important to know the exact location of the implant and/or the ligament graft with respect to the bone and tissue in the body during the procedure so that the ligament graft can be properly secured. Otherwise, a surgeon may try to secure the implant and ligament graft when they are not in desirable positions, or the surgeon may try to pull the implant or ligament graft further than desired, which can damage the implant, ligament graft, or parts of the body. While measurements can be taken and markings can be made on the implant to assist a surgeon in knowing the location of the implant and ligament graft, mechanisms and methods for measuring and marking remain primitive.

Accordingly, there remains a need for improved devices and methods for managing implants and ligament grafts, including filaments associated therewith, prior to and during surgical procedures.

SUMMARY

Devices and methods are generally provided for managing surgical implants. The implants typically have one or more filaments associated therewith, and are used in conjunction with ligament graft. In one exemplary embodiment, a surgical implant management device includes a body having a first end, a second end, opposed walls, extending between the first and second ends, a top side, and a bottom side. The device can also be described as being a card. A number of features can be incorporated into the device. One such feature can be an implantable body retainer that is configured to retain an implantable body on a top side of the body. Another such feature can be an opening disposed more proximate to the second end than the first end of the device, sometimes referred to as a graft-receiving opening. Still another such feature can be a fold extending across the body, between the opposed walls, and intersecting the opening. The fold can be configured such that the second end of the body is folded toward the bottom side of the body to form a filament loop engaging region along the fold. The filament loop engaging region can be configured to receive one or more filament loops coupled to an implantable body retained by the implantable body retainer.

In some embodiments, the graft-receiving opening can be approximately symmetrical along a central longitudinal axis extending approximately parallel to the opposed walls, and approximately symmetrical along the fold. A pair of opposed openings can be disposed on either side of the central longitudinal axis of the body, which itself can be approximately parallel to the opposed walls. The pair of opposed openings can be intersected by the fold. The configuration of the graft-receiving opening and the opposed openings can be such that a portion of the body disposed between the opposed openings and the graft-receiving opening forms prongs of the filament loop engaging region for receiving one or more filament loops.

A slit can be formed in the body between the graft-receiving opening and the implantable body retainer. The slit can be configured to receive the second end of the body that is folded toward the bottom side of the body. In some embodiments, an alignment opening can be formed adjacent to the implantable body retainer. The alignment opening can be configured to align the device on a graft preparation board.

A further feature of the implant management device can be one or more indicia formed on the top side of the body between the implantable body retainer and the fold. The indicia can be configured for use to mark an indicator on one or more filament loops coupled to an implantable body retained by the implantable body retainer, with the indicator being indicative of a relevant depth for a surgical procedure, such as a depth of a bone tunnel. In some embodiments, in addition to or in the alternative to the aforementioned indicia, indicia can be formed on the top side of the body between the fold and the second end. The indicia can be configured for use to mark an indicator on a ligament graft associated with one or more filament loops coupled to an implantable body retained by the implantable body retainer, with the indicator being indicative of a relevant depth for a surgical procedure.

One or more filament retention features can also be incorporated as part of the device. In some embodiments, the feature(s) can be disposed between the first end and the implantable body retainer. One example of such a feature can be a pair of opposed tabs extending below the bottom side of the body, with the tabs being configured to hold one or more filament limbs extending from an implantable body associated with the device. Further, a bore can be formed in the body and can be in communication with a slit formed in the first end. The bore can be configured to receive the one or more filament limbs extending from the implantable body via the slit. Another example of a filament retention feature can be a bore formed in the body and in communication with a slit formed in one of the opposed walls. The bore can be configured to hold one or more filament limbs extending from an implantable body associated with the device. The limb(s) can be slid into the bore via the slit. Still a further example of a filament retention feature can be a tab formed from two slits formed in one of the opposed walls. The tab can be configured to hold one or more filament limbs extending from an implantable body associated with the device.

In some embodiments, a device can be associated with the implant management device. The device can have a variety of configurations, but in one exemplary embodiment the device includes an implantable body and one or more filament loops coupled to the body. The one or more filament loops can have at least one limb extending therefrom. In some embodiments, the limb(s) can be configured to adjust a size of one or more of the loops when tension is applied to the limb(s). The implantable body can be retained by the implantable body retainer, the loop(s) can be held in tension by the filament loop engaging region, and the limb(s) can be held in tension by one or more of the filament retention features of the device. In some embodiments, the implant can further include at least one of a shuttle filament and a toggle filament coupled to the implantable body. The shuttle and/or toggle filament can be held in tension by one or more of the filament retention features.

Another exemplary embodiment of a surgical implant management device includes a body having opposed first and second surface and opposed first and second ends. The device can again also be described as a card, and a number of features can be incorporated in to the device. One such feature can be an implantable body retainer positioned between the first and second ends. Another such feature can be a first filament receiving region located at a second end of the body. The first filament receiving region can include at least one feature protruding from the second end in a direction that is substantially parallel to a longitudinal axis of the body. Further, the first filament receiving region can be configured to receive one or more filament loops coupled to an implantable body held by the implantable body retainer. Still another feature can be an opening disposed between the implantable body retainer and the first filament receiving region. The opening, sometimes referred to as a graft-receiving opening, can extend between the first and second surfaces of the body, and can be configured to receive a ligament graft to be coupled to one or more of the filament loops. Yet a further feature of the device can be one or more indicia formed on the first surface of the body. The indicia can be located between the implantable body retainer and the first filament receiving region, and can be configured for use to mark an indicator on one or more of the one or more filament loops. The indicator can be indicative of a relevant depth for a surgical procedure, such as a depth of a bone tunnel.

The implant management device can also include a second filament receiving region that is formed proximate to the first end of the body. One or more of a variety of filament retention features can be included as part of the second filament receiving region, and thus such features can be disposed between the first end and the implantable body retainer. For example, the region can include a pair of opposed tabs raised above the second surface of the body, with the tabs being configured to hold one or more filament limbs extending from an implantable body associated with the implant management device. By way of further example, a bore can be formed in the body and can be in communication with a slit formed in the first end. The bore can be configured to receive one or more filament limbs extending from an implantable body via the slit. Yet a further example of a filament retention feature provided as part of the second filament receiving region can be a bore formed in the body and in communication with a slit formed in one of a first opposed wall and a second opposed wall, the opposed walls both extending between the first and second ends. The bore can be configured to hold one or more filament limbs extending from an implantable body and slid into the bore via the slit. A still further example of a filament retention feature is a tab formed from two slits formed in an opposed wall of the body. The tab can be configured to hold one or more filament limbs extending from an implantable body.

In some embodiments, the at least one protruding feature of the first filament region can include two prongs. In certain configurations, a space between the two prongs can form an open pathway to the graft-receiving opening disposed between the implantable body retainer and the first filament receiving region. Another feature of the implant management device can be an alignment opening formed adjacent to the implantable body retainer. The alignment opening can extend between the first and second surfaces and can be configured to align the device on a graft preparation board.

The implant management device can also include one or more second indicia. The second indicia can be formed on the second surface of the body between the second end of the body and a terminal end of the graft-receiving opening disposed a distance away from the second end. The indicia can be configured for use to mark an indicator on a ligament graft associated with one or more filament loops coupled to an implantable body retained by the implantable body retainer, with the indicator being indicative of a relevant depth for a surgical procedure. In some embodiments, a portion of the second surface can result from folding the body of the device along a fold that extends substantially transverse to the longitudinal axis of the body at a location between the implantable body retainer and the second end.

The implantable body retainer can include a pair of opposed tabs. A base of the first tab can be disposed on a first side of a central longitudinal axis that extends lengthwise through the body, and a terminal end of the tab can be disposed on a second, opposite side of the central longitudinal axis. A base of the second tab can be disposed on the second side of the central longitudinal axis, and a terminal end of the tab can be disposed on the first side of the central longitudinal axis. A distance between the second tab and the first end can be shorter than a distance between the first tab and the first end.

In some embodiments, a device can be associated with the implant management device. The device can have a variety of configurations, but in one exemplary embodiment the device includes an implantable body and one or more filament loops coupled to the body. The one or more filament loops can have at least one limb extending therefrom. In some embodiments, the limb(s) can be configured to adjust a size of one or more of the loops when tension is applied to the limb(s). The implantable body can be retained by the implantable body retainer, the loop(s) can be held in tension by the first filament receiving region, and the limb(s) can be held in a tensioned state by the second filament receiving region.

One exemplary embodiment of a method for preparing a ligament graft for implantation includes positioning a ligament graft through a graft-receiving opening of an implant management card. An implantable body can be disposed on the card, the body having one or more filament loops associated therewith. At least a portion of the graft-receiving opening can be disposed within a loop opening of at least one loop of the one or more filament loops. The method can for preparing the ligament graft can further include applying tension to the ligament graft, and marking a depth on at least one loop of the filament loop(s), with the indicia for use in marking the first depth are provided on a first surface of the implant management card. In some embodiments, the first depth marked can be a total bone stock depth.

The method can also include decoupling the implantable body and the filament loop(s) associated therewith from the implant management card. In some embodiments, a second depth can be marked, with that depth being marked on the ligament graft. The indicia for use in marking the second depth can be provided on a second, opposed surface of the implant management card. The second depth marked can be indicative of a graft-in-tunnel depth. When marking a second depth on the ligament graft, the method can include unfolding the implant management card to reveal the indicia for use in marking the second depth. Still further, a step of applying tension to the ligament graft can include positioning a post of a graft preparation board in an alignment opening of the implant management card and moving the ligament graft away from the post to apply tension to the ligament graft.

BRIEF DESCRIPTION OF DRAWINGS

This invention will be more fully understood from the following detailed description taken in conjunction with the accompanying drawings, in which:

FIG. 10B is a top view of still another exemplary embodiment of a surgical implant management device, the device being in an unfolded configuration;

FIG. 11 is a top view of an exemplary embodiment of a surgical implant management device, the device being in an unfolded configuration;

DETAILED DESCRIPTION

Figure 1A:
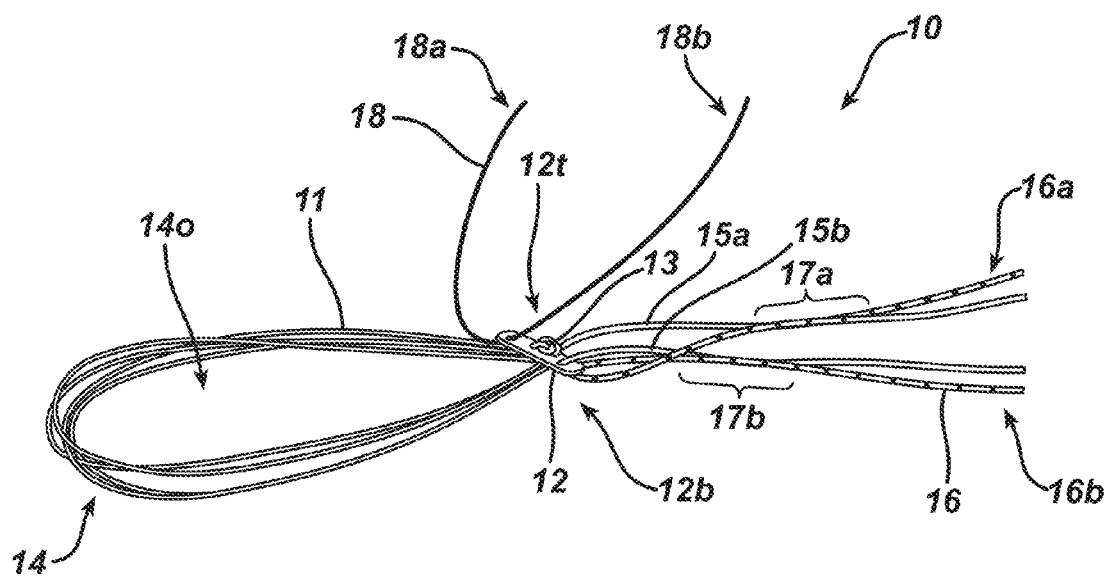
FIG. 1A is a perspective view of one exemplary embodiment of a surgical implant in the prior art.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. As a result, to the extent one exemplary embodiment of a surgical implant management device includes a particular feature, a person skilled in the art would be able to incorporate that feature into other surgical implant management devices, including in the various embodiments of devices provided for herein, as well as in other devices and the like used to manage implants that are known to those skilled in the art.

In the present disclosure, like-numbered components of the embodiments generally have similar features and/or purposes. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the implant management devices, and the components associated therewith, can depend at least in part on the anatomy of the subject in which the implants will be used, the sizes and shapes of the components with which the implant management devices will be used, and the methods and procedures in which the systems and devices will be used. To the extent features are described herein as being a "first feature" or a "second feature," such numerical ordering is generally arbitrary, and thus such numbering can be interchangeable.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. Additionally, a number of terms may be used throughout the disclosure interchangeably but will be understood by a person skilled in the art. By way of non-limiting example, the terms "suture" and "filament" and "flexed" and "folded" may be used interchangeably.

The present disclosure generally relates to a surgical implant management device for selectively retaining a surgical implant or other construct. The management device can be used both to hold the components of the implant prior to use of the implant in a surgical procedure, and it can be used to help prepare for the surgical procedure, at least due in part to some of the features provided for as part of the device. For example, as described in further detail below, the device can include features that allow for a user to easily mark particular distances on the device, the implant, and/or a ligament graft associated therewith to help the user better know the location of the implant and ligament graft during a surgical procedure. The device can include features incorporated therewith, such as measurement indicia on a surface of the device, such that additional devices, for example rulers, are not needed to determine particular distances or lengths. Still further, the various configurations provided for herein can make it easier to keep various filaments of the implant from getting tangled, to more easily identify the filaments, and in general, can make it easier to use the implant and perform the procedures associated therewith.

Surgical Implant

Figure 1B:
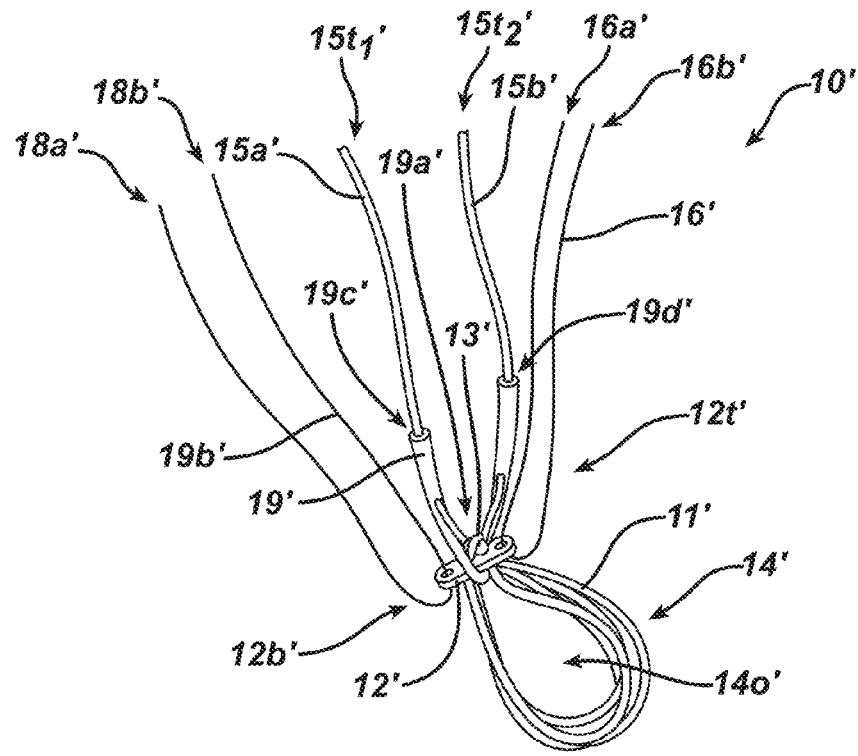
FIG. 1B is a perspective view of another exemplary embodiment of a surgical implant in the prior art.

While the disclosure provided for herein can be used in conjunction with a variety of implants, two non-limiting exemplary embodiments are illustrated in FIGS. 1A and 1B. Each of the implants 10, 10' generally includes an implantable body 12, 12' associated with one or more filaments in which at least one filament forms one or more adjustable coils or loops 14, 14'. More particularly, FIG. 1A illustrates an implant 10 that includes a body 12 having thru-holes formed therein and a first suture filament 11 associated therewith. The first filament 11, sometimes referred to as a graft-holding suture, can be coupled to or otherwise associated with the body 12 and configured to hold a ligament graft for implantation. In the illustrated embodiment, a portion of the first filament 11 is formed into a plurality of adjustable coils or loops 14 defined by a self-locking knot 13 disposed on a top side 12t of the body 12, with the loops 14 primarily being disposed on a bottom side 12b of the body 12. The filament 11 can include at least one adjustable limb or tail, as shown a first adjustable limb 15a and a second adjustable limb 15b, extending from the knot 13, and the limbs 15a, 15b can be operable to adjust a size of one or more openings 14o formed by one or more of the loops 14 when tension is applied thereto.

One or more additional filaments can be removably associated with the body 12 to help control the implant during a surgical procedure. As shown, a second filament 16, sometimes referred to herein as a shuttle suture or filament or a leading suture or filament, is disposed in a thru-hole located in a first end of the body 12, and a third filament 18, sometimes referred to herein as a trailing or toggle suture or filament, is disposed in a thru-hole located in a second end of the body 12. These two filaments 16, 18, collectively referred to as guide filaments, can be used to help position and set the implant 10, and thus the ligament graft associated therewith, at a desired implant location. In the illustrated embodiment, a first limb 16a and a second limb 16b of the second filament 16 extend from opposed sides of one thru-hole, and a first limb 18a and a second limb 18b of the third filament 18 extend from opposed sides of another thru-hole.

Further, in some exemplary embodiments, each limb 16a, 16b can include a receiving portion 17a, 17b configured to receive respective portions of the first and second adjustable limbs 15a, 15b. Disposing the limbs 15a, 15b within the receiving portions 17a, 17b can assist in filament management, as well as provide a convenient way to help insure that any cutting of the first and second adjustable limbs 15a, 15b is not to the detriment of the integrity of the self-locking knot 13. More particularly, a portion of the limbs 15a, 15b disposed within the receiving portions 17a, 17b can be trimmed to maintain the integrity of the knot 13. A person having skill in the art will recognize that the integrity of the knot 13, and thus the strength of the implant 10, can be compromised when the limbs 15a, 15b are cut too close to the body 12. Further details about implants of the nature illustrated in FIG. 1A are provided in U.S. patent application Ser. No. 14/103,167, entitled "Implant Having Filament Limbs of an Adjustable Loop Disposed in a Shuttle Suture," filed Dec. 11, 2013, the content of which is incorporated by reference herein in its entirety.

The implant of FIG. 1B is another exemplary embodiment of an implant 10' that can be used in conjunction with the implant management devices and surgical methods provided for herein. As shown, the implant 10' is similar to the implant 10 of FIG. 1A, except that it provides for an alternative configuration for protecting the integrity of a knot of a first filament. Similar to the implant 10, the implant 10' includes a body 12' having thru-holes formed therein, a first filament 11' coupled to or otherwise associated with the body 12', and second and third filaments 16', 18' removably coupled to opposed thru-holes of the body 12'. A portion of the first filament 11' can be formed into a plurality of adjustable coils or loops 14' defined by a self-locking knot 13' disposed on a top side 12t' of the body 12', with the loops 14' primarily being disposed on a bottom side 12b' of the body 12'. The filament 11' can include at least one adjustable limb or tail, as shown a first adjustable limb 15a' and a second adjustable limb 15b', extending from the knot 13', and the limbs 15a', 15b' can be operable to adjust a size of one or more openings 14o' formed by one or more of the loops 14' when tension is applied thereto. The second and third filaments 16', 18' can serve as leading and trailing filaments, with first and second limbs 16a', 16b' of the second filament 16' extending from opposed sides of one thru-hole d, and first and second limbs 18a', 18b' of the third filament 18' extending from opposed sides of another thru-hole.

Unlike the embodiment of FIG. 1A, the second filament 16' does not receive portions of the adjustable limbs 15a', 15b'. Instead, a sleeve or spacer 19' is disposed over a portion of the first and second adjustable limbs 15a', 15b' on the top side 12t' of the body 12', adjacent to a top surface of the body 12'. More particularly, as illustrated, the sleeve 19' is a single suture filament having a plurality of bores formed therein to receive first and second adjustable limbs 15a', 15b'. The sleeve 19' can be disposed around a portion of the first limb 15a' on the top side 12t', wrap around a bottom surface of the body 12', and then wrap back around to the top side 12t' so it can be disposed around a portion of the second limb 12b'. Wrapping the sleeve 19' around the bottom surface of the body 12' can help minimize proximal movement of the sleeve 19', towards terminal ends $15t_1'$, $15t_2'$ of the adjustable limbs 15a', 15b', when the limbs 15a', 15b' are tightened. The first terminal end $15t_1'$ can pass into the sleeve 19' at a first bore 19a' and out of the sleeve 19' at a second bore 19b', while the second terminal end $15t_2'$ can pass into the sleeve 19' at a third bore 19c' and out of the sleeve 19' at a fourth bore 19d'. Similar to the receiving portions 17 of the implant 10, the sleeve 19' can assist in preventing a surgeon from cutting the limbs 15a', 15b' too close to the body 12'. More particularly with respect to this embodiment, the sleeve 19' can generally have elastic properties such that it bunches as compressive forces are applied, and a surgeon can then cut the limbs 15a', 15b' at a location proximate to the bores 19b', 19d'. Further details about an implant of the nature illustrated in FIG. 1B are provided in U.S. patent application Ser. No. 13/793,514, entitled "Implant Having Adjustable Filament Coils," filed Mar. 11, 2013, the content of which is incorporated by reference herein in its entirety.

A variety of other configurations of implants of the nature provided for herein, as well as other types of implants, can be used in conjunction with the disclosures provided herein pertaining to implant management devices and methods. By way of non-limiting example, in some embodiments, one or more loops associated with an implant body can be fixed as opposed to adjustable, and one or more limb(s) extending therefrom can be configured for other purposes besides adjusting a size of the loops, such purposes being known to those skilled in the art.

Implant Management Device

Figure 2A:
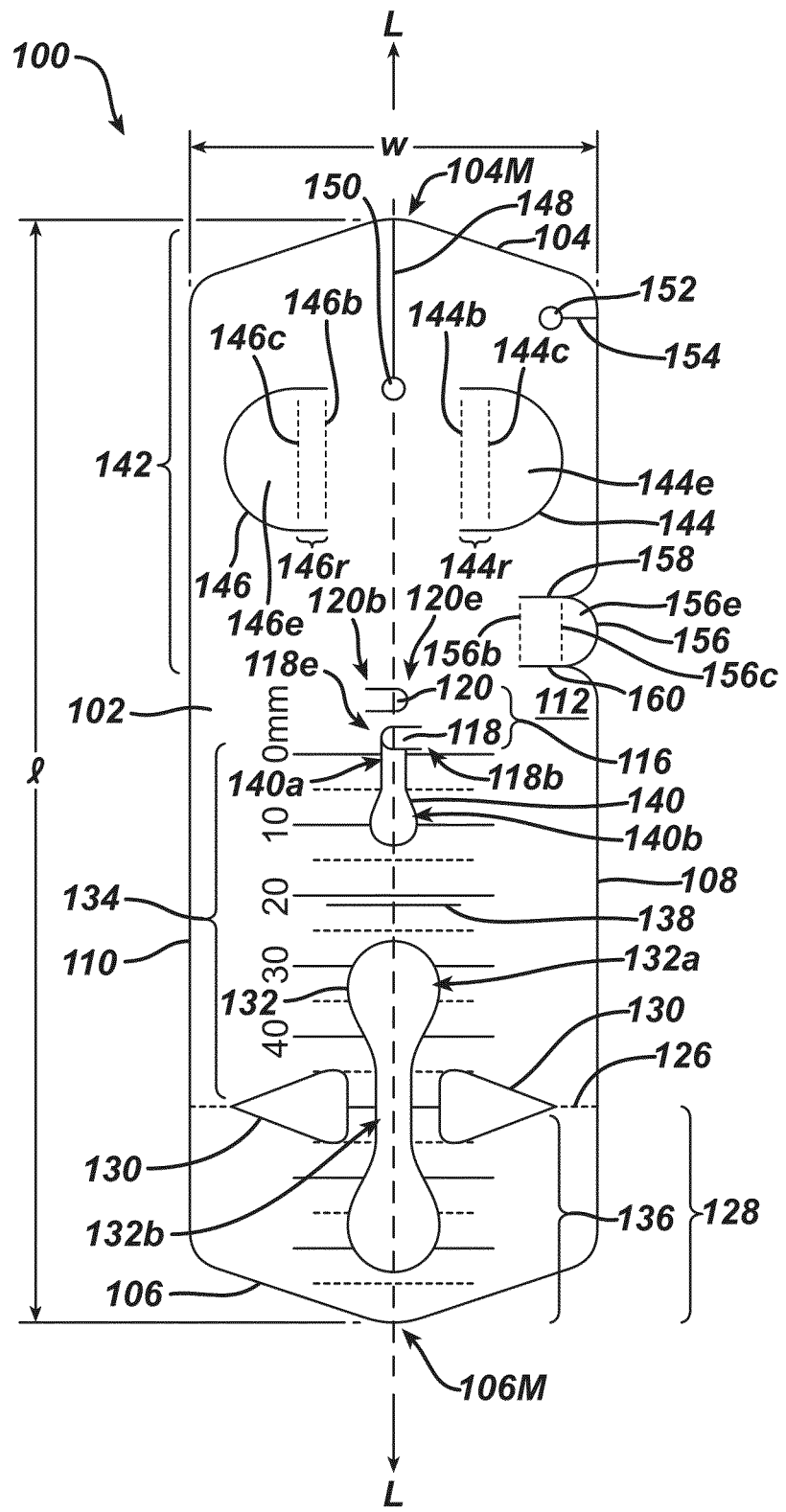
FIG. 2A is top view of one exemplary embodiment of a surgical implant management device, the device being in an unfolded configuration.
Figure 2B:
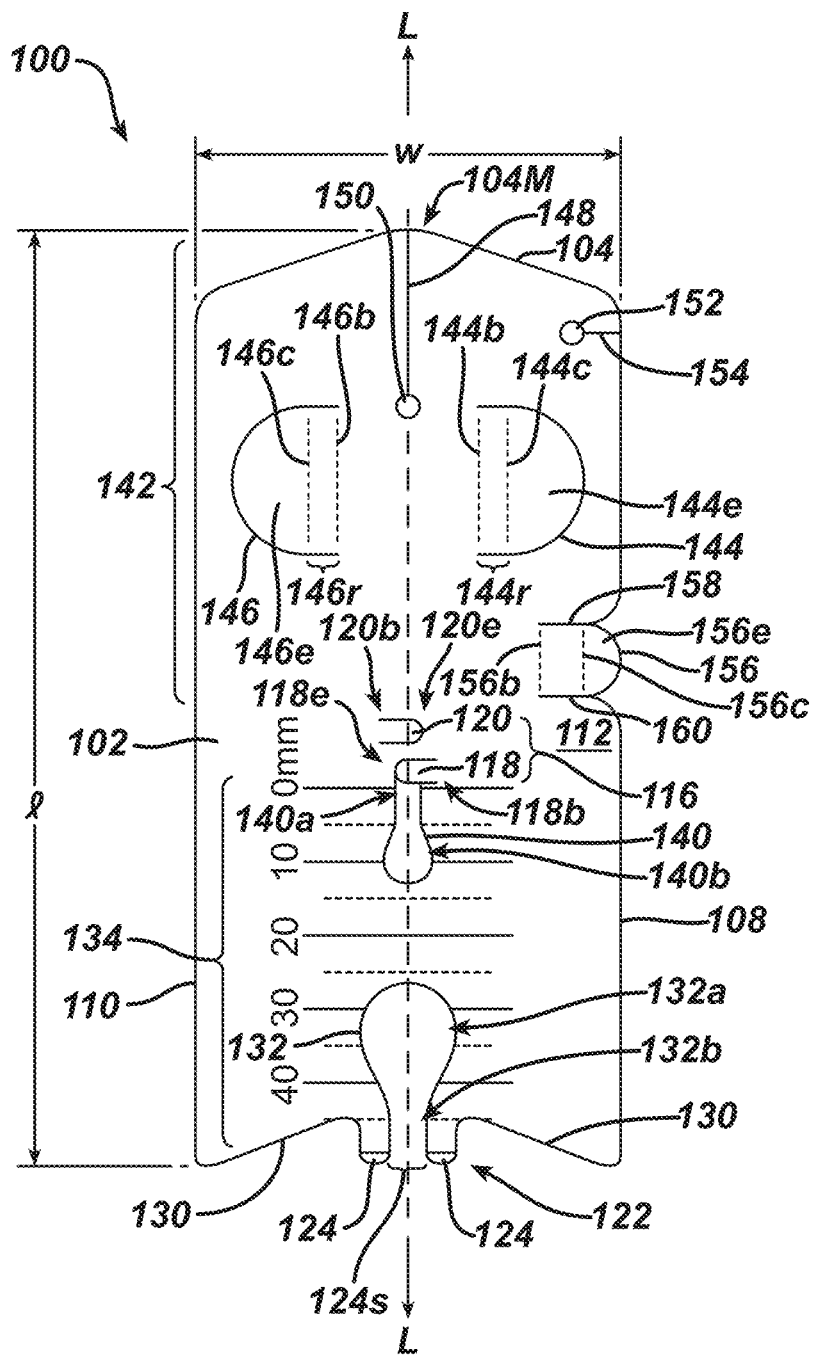
FIG. 2B is a top view of the device of FIG. 2A, the device being in a folded configuration.
Figure 2C:
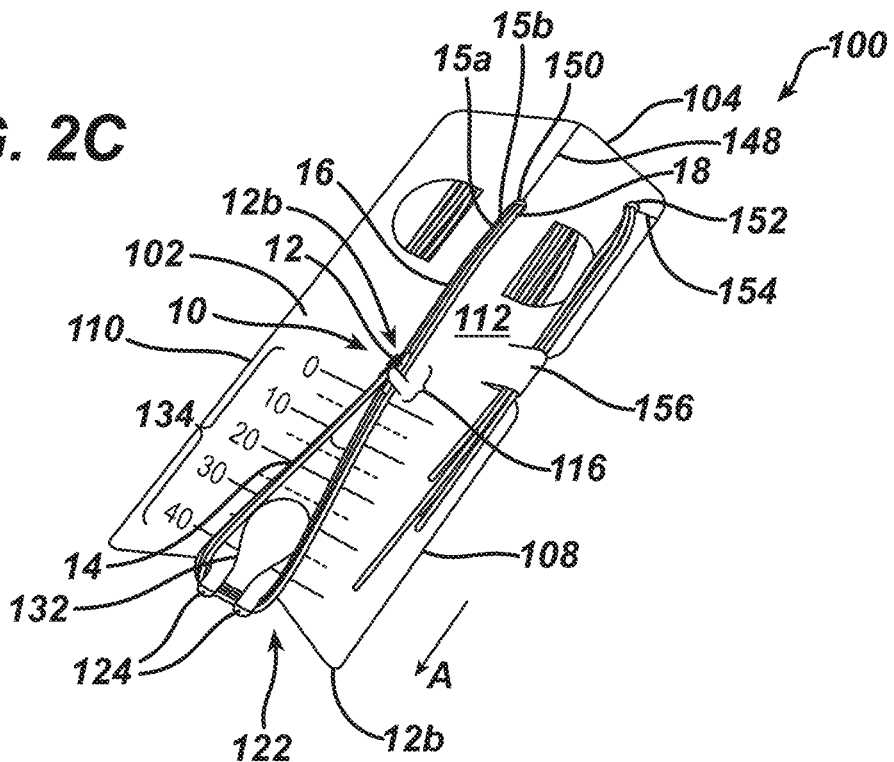
FIG. 2C is a perspective top view of the device of FIG. 2B having the implant of FIG. 1A associated therewith.
Figure 2D:
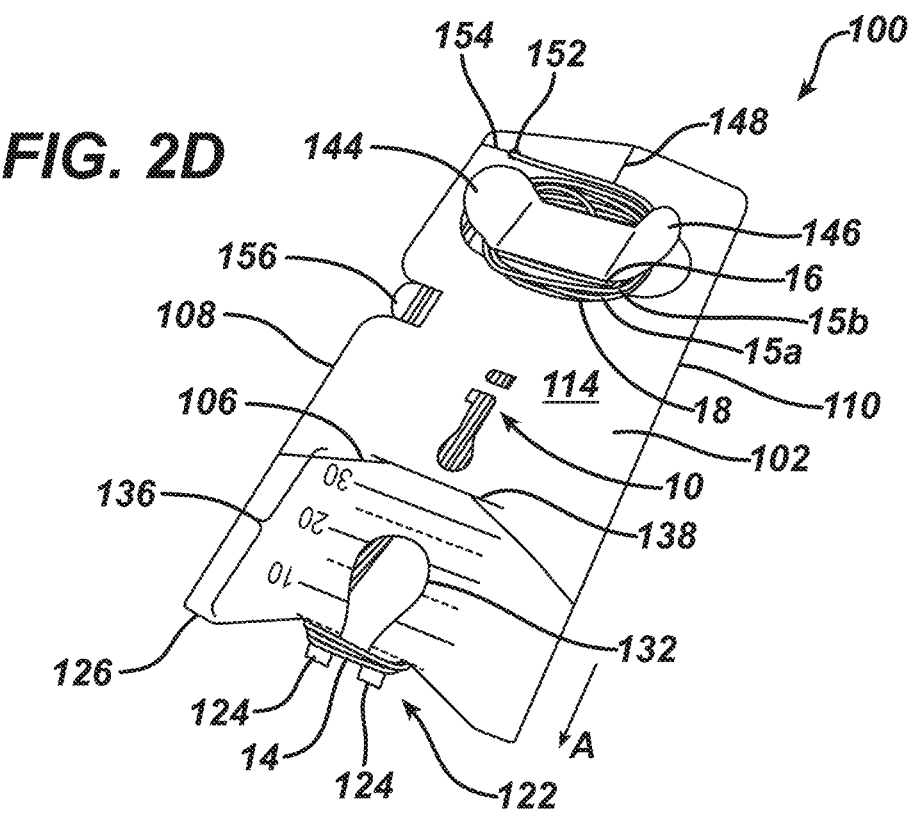
FIG. 2D is a perspective bottom view of the device of FIG. 2C.

FIGS. 2A and 2B illustrate one exemplary embodiment of a surgical implant management device 100, sometimes referred to herein as an implant management card. The card 100 in its unfolded state is shown in FIG. 2A, while a configuration of the card 100 in a folded state, sometimes referred to herein as a compact configuration, is shown in FIG. 2B. More particularly, FIG. 2B results from folding a second portion 128 of the card 100 underneath the illustrated top side or surface 112, i.e., towards a bottom side or surface 114 (FIG. 2D) of the card 100. This results in indicia 136 formed on the second portion 128, as shown in FIG. 2A, being visible on the bottom side 114 of the card 100, as shown in FIG. 2D. In the folded or compact configuration, the second portion 128, and in particular the indicia 136 formed thereon, can, for all intents and purposes, become part of the bottom surface 114.

While a body 102 of the card 100 itself can have a variety of shapes and configurations, some of which are illustrated herein and many others of which are derivable based on the present disclosure, in the illustrated embodiment the body 102 has a generally rectangular shape defined by a first end 104, a second end 106, and opposed walls 108, 110 extending between the two ends 104, 106. The device also includes a top side or surface 112, sometimes referred to as a first side or surface, and a bottom side or surface 114, sometimes referred to as a second side or surface. A central longitudinal axis L can extend the length of the body 102, and can be located approximately equidistant from the two opposed sides 108, 110. For ease of reference, the central longitudinal axis L will be used in each embodiment described herein, even when the other reference numerals change. The body 102 can generally be defined as having a length l, a width w, and a thickness t (not labeled, but extending between the top surface 112 and the bottom surface 114). Depending on configuration of the card 100, any of the length l, the width w, and the thickness t can change when the card 100 is moved from an unfolded configuration to a folded configuration.

Although the body 102 is described as being generally rectangular in shape, a person skilled in the art will see that the first and second ends 104, 106 are not singular straight lines that are perpendicular to the central longitudinal axis L as in a typical rectangle. Instead each end 104, 106 is tapered toward a midpoint 104M, 106M thereof, thus creating symmetrical ends. As discussed below, the first and second ends 104, 106 can have a variety of other shapes, depending, at least in part, on the other features, shapes, and dimensions of the cards, without departing from the spirit of the present disclosure. In exemplary embodiments, the length l in the unfolded configuration can be approximately in the range of about 100 millimeters to about 250 millimeters, in the folded configuration it can be approximate in the range of about 80 millimeters to about 220 millimeters, the width w in the folded or unfolded configuration can be approximately in the range of about 35 millimeters to about 80 millimeters, and the thickness t in the unfolded configuration can be approximately in the range of about 0.01 millimeters to about 1 millimeters, with the thickness t changing for portions of the card in the folded configuration based on the amount of folding that occurs, such thickness changes being easily determinable by a person skilled in the art. In one exemplary embodiment, the length l in the unfolded configuration can be approximately 160 millimeters, the length l in the folded configuration can be approximately 130 millimeters, the width w can be approximately 55 millimeters, and the thickness t in the unfolded configuration can be approximately 0.5 millimeters.

The surgical implant management device 100 includes a number of different features that improve a user's ability to manage the filaments before and during a surgical procedure. One such feature is an implantable body retainer 116. As shown, the implantable body retainer includes two staggered, opposed tabs 118, 120 configured to grasp opposite ends of an implantable body. The tabs 118, 120 can be configured to hold the body at a particular location consistent with indicia 134, 136 formed on the device 100. Accordingly, the first tab 118 can be adjacent to a 0 millimeter indicia line and the second tab 120 can be a distance apart from the location of the first tab 118, closer to the first end 104 than the first tab 118 is. Both tabs 118, 120 can be configured to pivot at their respective bases 118b, 120b so that the ends 118e, 120e of the tabs 118, 120 can be moved out of a plane that extends substantially through the top surface 112. As designed, both tabs 118, 120 can pivot out of the page, as shown in FIG. 2C, thus allowing an implant body to be tucked underneath the tabs 118, 120 and be supported by other portions of the top surface 112. Thus, in the illustrated embodiment, the tabs 118, 120 operate to retain an implant body on the top surface 112 of the implant management device 100.

While the tabs 118, 120 of the implantable body retainer 116 can have a variety of shapes and sizes, depending, at least in part, on the size and shape of the other portions of the implant management device and the implant itself, in the illustrated embodiment the two tabs 118, 120 have a finger-like shape that can be also be described as being elongate and semi-elliptical. A length of each tab 118, 120 is such that the base 118b, 120b extends on one side of the central longitudinal axis L, while the terminal end 118d, 120e of the same tab 118, 120 extends on the opposite side of the central longitudinal axis L. This geometry can help secure an implant body to the surface 112 in use.

Another feature of the device 100 can be a filament loop engaging region 122, sometimes referred to herein as a first filament receiving region, which can be used to retain and tension one or more filament loops that extend below a bottom side of an implant body. The filament loop engaging region 122 can have many different configurations. In the embodiment illustrated in FIG. 2B, the filament loop engaging region 122 includes at least one protruding feature, as shown two prongs 124, around which the filament loops can be disposed. As a result, all of the loops of the implant can be held together, in a tensioned state, by a single component. The prongs 124 can be formed by folding a portion of the device 100 along a fold 126 formed in the body 102. More particularly, a second portion 128 of the device 100, which as shown is the portion of the device 100 disposed between the fold 126 and the second end 106, can be folded toward a bottom surface 114, i.e., into the page as illustrated. As a result, a combination of the opposed cutouts or openings 130 formed through the body 102 and a central cut-out or opening 132 also formed through the body, can form the opposed prongs 124. In the illustrated embodiment, the opposed openings 130 have a generally triangular shape, although a variety of other shapes can also be used to form the opposed openings. Further, as shown, the fold 126 intersects and substantially bisects the triangularly-shaped cutouts 130. The taper formed by sides of the triangularly-shaped cutouts 130 can help prevent the loop(s) from slipping off the prongs 124.

The fold 126 can extend across the width w of the body 102, between the opposed walls 108, 110. A person skilled in the art will recognize that a location of the fold 126, and thus the end of the prongs 124, can depend on a variety of factors, including the implant being used in conjunction with the implant management device, and the type of procedure in which the implant is being used. In some exemplary embodiments, the fold 126 is generally located to allow the loops to have a tension applied thereto as a result of engaging the prongs 124. In some implant embodiments, the size of the loops can be adjusted using filament limbs so that the loops can be appropriately tensioned on the prongs 124.

Although the prongs 124 that form the filament loop engaging region 122 illustrated in FIG. 2B are formed by folding over a portion of the body 102, other configurations can be used to engage filament loops extending from an implant body. For example, in some instances the filament loop engaging region 122 can be pre-formed on the device 100 such that no folding or other changes to the initial configuration are necessary to form the filament loop engaging region 122. Thus, in some embodiments prongs 124 can be pre-formed at the second end 106 of the device 100.

The opening 132 that forms the part of the prongs 124 can also be used to receive a ligament graft. As shown, at least a portion of the graft-receiving opening 132 can be disposed between the implantable body retainer 116 and the prongs 124 so that when a ligament graft is passed through the opening 132, it is passed through at least one of the openings of the filament loop(s) of an implant, as described in further detail below. In the illustrated embodiment, the opening 132 is more proximate to the second end 106 than the first end 104.

The opening 132 can have any number of shapes and sizes, but in the illustrated embodiment it is symmetrical along the central longitudinal axis L. The opening 132 can also be bisected by the fold 126, and thus can be symmetrical with respect to the fold 126. As a result, when the second portion 128 is folded toward the bottom side 114, the resulting configuration is one in which one half of the opening 132 is substantially aligned with the other half of the opening 132.

In the illustrated embodiment, the approximate shape of the opening 132 in the unfolded configuration can be similar to a dumbbell. Once folded, the larger portion 132a of the dumbbell-shaped opening 132 can be large enough to receive a ligament graft, while the smaller portion 132b of the opening 132 can help to form the shape of the prongs 124. In particular, the portion of the device 100 disposed between the smaller portion 132b and the opposed openings 130 forms the prongs 124 of the filament loop engaging region 122. As shown in FIG. 2B, a space 124s between the two prongs 124 can form an open pathway to the remainder of the opening 132. In other embodiments, material can be disposed between the two prongs 124, thereby eliminating the open pathway.

Another feature of the device 100 can be first indicia 134 formed on the top side 112. The first indicia 134 can be used for a variety of reasons, but in one exemplary embodiment they can assist a user in marking particular measurements on loops of an implant coupled to the device 100. In some instances, the first indicia 134 can be used in marking particular measurements on a ligament graft. In the illustrated embodiment, the first indicia 134 begins proximate to the first tab 118 at 0 millimeters and extend to 50 millimeters, which is located approximately at the fold 126. Each indicia line extends substantially parallel to the fold 126. Each solid indicia line denotes an increment of 10 millimeters, and each dotted indicia line denotes an increment of 5 millimeters between each 10 millimeter indicia line. Other indicia are also permitted on the top surface of the device. For example, second indicia 136 can also be provided on the top side 112 between the fold 126 and the second end 106. As shown, an additional 30 millimeters are marked off in 5 millimeter increments between the fold 126 and the second end 106. The second indicia 136 can be used to assist in marking particular measurements on a ligament graft associated with an implant, or on filaments of the implant, depending on the implant and implant management device configurations.

A receiving slit 138 can be formed in the body 102 for receiving the second end 106 when it is folded toward the bottom side 114. As shown in FIG. 2A, the receiving slit 138 can be disposed between the fold 126 and the first end 104, and can extend substantially parallel to the fold 126. In the illustrated embodiment the receiving slit 138 is actually between the implantable body retainer 116 and the fold 126. The location of the receiving slit 138, however, can generally be dependent on the shape and length of the second end 106 that is folded over toward the bottom side 114. Accordingly, a length between the fold 126 and the receiving slit 138 can be approximately the same as the length of the second portion 128. The length and shape of the slit 138 can correspond to the shape of the second end 106 that the slit is configured to receive.

Another feature that can be incorporated into the device 100 is an alignment opening 140 for associating the device 100 with a graft preparation device. In the illustrated embodiment, the alignment opening 140 is located adjacent to the implantable body retainer 116, between the implantable body retainer 116 and the fold 126. The hole 140 can have a variety of shapes and sizes adapted to receive a post of a graft preparation device. A person skilled in the art will recognize that a graft preparation device can be used with ligament grafts so that appropriate notations can be made on the ligament grafts, as well as on implant management devices, in view of the disclosures provided for herein. An example of a graft preparation device is discussed below, and a person having skill in the art will recognize a variety of graft preparation devices configurations with which the implant management device 100 can be adapted for use. The alignment opening 140 can be generally elongate, and in the illustrated embodiment is generally teardrop shaped. A first end 140a of the opening 140 can be configured to be complementary to the size of a post of the graft preparation device, while a second end 140b can have a bigger diameter than the first end 140 to make it easier to initially receive the post and position the implant management device 100 such that the post engages the device 100 at the first end 140a.

A number of features to help manage limbs and other filaments extending generally from the top side of the implant can also be included as features of the device 100. These features can generally be referred to as filament retention features, and the location of at least some of these features on the device 100 can sometimes be referred to as a second filament receiving region 142. In addition to retaining filament associated with the implant, at least some of these features can apply tension to the filament to help keep the filament out of the way.

One example of a filament retention feature is shown in FIGS. 2A and 2B as opposed tabs 144, 146 formed between the implantable body retainer 116 and the first end 104. As shown, the tabs 144, 146 can be spaced approximately equidistant from the central longitudinal axis L, and can be described as being horizontally-disposed with respect to the central longitudinal axis L. Each tab 144, 146 can include two folds 144b, 144c and 146b, 146c. A first, more centrally-disposed fold 144b, 146b can be formed between the tab 144, 146 and the body 102, thereby allowing the tab 144, 146 to be moved out of a plane extending substantially through the body 102. In the illustrated embodiment, as shown in FIG. 2D, the tabs 144, 146 can be configured to move in an opposite direction of the implantable body retainer tabs 118, 120, and thus can extend into the page when folded. Each tab 144, 146 can be folded along the second fold 144c, 146c to provide a receiving region 144r, 146r along which filaments can be wound. As shown in FIG. 2D, end portions 144e, 146e of the tab 144, 146 can be substantially parallel to the plane extending substantially through the body 102. Any and all portions of any filament associated with the implant can be wrapped around the tabs 144, 146, as described in greater detail below. The tabs 144, 146 can help to keep the various filaments organized, and can also decrease the likelihood that any filaments will become tangled. The filaments can also be kept in a tensioned state once they are wrapped around the tabs 144, 146.

A centrally disposed slit 148 can be formed in the first end 104 and extend towards the tabs 144, 146. The slit 148 can serve as an access point for filament to be disposed prior to winding it around the tabs 144, 146. As shown, the slit 148 terminates at a bore 150 extending through the body 102. A portion of the filament can be disposed in the bore 150 prior to winding it around the tabs 144, 146.

Another feature for retaining filament is provided by way of a bore 152 extending through the body 102 and configured to receive any and all of the filaments. The bore 152 can be disposed in the second filament receiving region 142, proximate to the first end 104, between the centrally disposed slit 148 and one of the first and second opposed walls 108, 110. A slit 154 can be in communication with the bore 152 and can extend to the opposed wall nearest to the bore 152, as shown the first wall 108. As shown by FIGS. 2C and 2D, filament can wrap around the tabs 144, 146, extend from the tabs 144, 146 toward the bore 152, and can be slid through the slit 154 to enter the bore 152. In addition to the tabs 144, 146 maintaining a tensioned state in the filaments, in some embodiments, the bore 152 can also help to maintain tension in the filaments, for instance when the bore 152 has a diameter similar to the total diameter of filaments disposed therein.

A retention tab 156 can be provided as a further feature to assist with filament retention and management. As shown, the retention tab 156 can be located along one of the opposed walls 108, 110, as shown the first wall 108, and can be more centrally disposed along the wall 108 than the bore 152 and slit 154. In particular, the retention tab 156 can be disposed along the length l of the body 102 between the opposed tabs 144, 146 and the implantable body retainer 116. The retention tab 156 can be formed by two slits 158, 160 extending from the wall 108 and toward the central longitudinal axis L, approximately parallel to the fold 126, and can include two folds 156b, 156c formed therein, approximately perpendicular to the two slits 158, 160. The folds 156b, 156 can allow the tab 156 to form a sleeve for receiving filament, and at least in some instances, can apply tension to and/or maintain a tension in the filament disposed therein. The more centrally disposed fold 156b can be formed between the body 102 and the tab 156 so that the tab 156 can extend into or out of the page. The second fold 156c can allow an end 156e of the tab 156 to be folded over back toward the body 102 to form a sleeve, as shown in FIGS. 2C and 2D. By keeping filaments toward an edge of the device 100, users can more easily view the implant loops, ligament graft, and the indicia 134, 136 without filament impairing the view.

FIGS. 2C and 2D illustrate the device 100 having the implant 10 associated therewith. As shown, the body 12 of the implant 10 can be held at a desired location by the implantable body retainer 116 such that the start of the loops 14 extending from the bottom side 12b is approximately at the 0 millimeter indicia line. The loops can extend towards the filament loop engaging region 122 and can be held in place in a tensioned state by the prongs 124. As a result, the opening 132 for receiving the ligament graft is framed by the loops 14.

Each of the adjustable limbs 15a, 15b, as well as the two guide filaments 16, 18 also associated with the body 12, can extend from the body 12 towards the first end 104. The limbs 15a, 15b and guide filaments 16, 18 can extend through the slit 148 to the centrally disposed bore 150, and then can be wrapped around the tabs 144, 146 below the bottom side 114 of the device 100. The limbs 15a, 15b and guide filaments 16, 18 can extend towards the first wall 108, where they can be disposed in the side slit 154 to access the bore 152. The limbs 15a, 15b and guide filaments 16, 18 can then extend towards the filament loop engaging region 122, and can be grasped by the sleeve formed by the retention tab 156, before eventually terminating. Further details regarding techniques for attaching an implant to a device or card are described in greater detail below with respect to FIGS. 15L-S.

As shown, the first indicia 134 can be used to mark measurements on the loops 14 because the 0 millimeter indicia line coincides with the approximate starting point of the loops 14 with respect to the body 12. The second indicia 136 can be used in one of two manners. As shown in FIG. 2D, the second indicia 136 are located on the bottom side 114 of the device. In one exemplary embodiment, the second end 106 can be removed from the receiving slit 138 and returned approximately to its location in the unfolded configuration. Then a ligament graft disposed in the loops 14 and extending away from the prongs, in a direction A, can have measurements marked thereon using the second indicia 136, as described in greater detail below. Alternatively, a ligament graft can be associated with the loops and then extended towards the first end 104, along the bottom side 114, so that the second indicia 136 can be used to mark measurements on the ligament graft when the body 102 is in the folded configuration.

Alternative Embodiments of Implant Management Devices

FIGS. 3A-13 provide for various other embodiments of implant management devices. The features illustrated by these embodiments include some of the same features described with respect to the device of FIGS. 2A-2D in combination with other features and/or alternative embodiments of the same features of the device of FIGS. 2A-2D. A person skilled in the art will recognize that to the extent these embodiments include features in one embodiment but not in other embodiments, each and every embodiment is generally capable of being modified to include or exclude particular features without departing from the spirit of the disclosure. Further, to the extent some features are illustrated in multiple embodiments, such features may not be described in each embodiment for efficiency purposes. A person skilled in the art will recognize how these illustrated features are configured and capable of being used in light of the entirety of the present disclosure and the knowledge of the skilled person. Generally, features that have a similar configuration between different embodiments are numbered alike (e.g., 198, 298, 398), while features that serve a similar purpose but have a different configuration are numbered alike but have prime designations (e.g., 198, 298', 398").

Figure 3A:
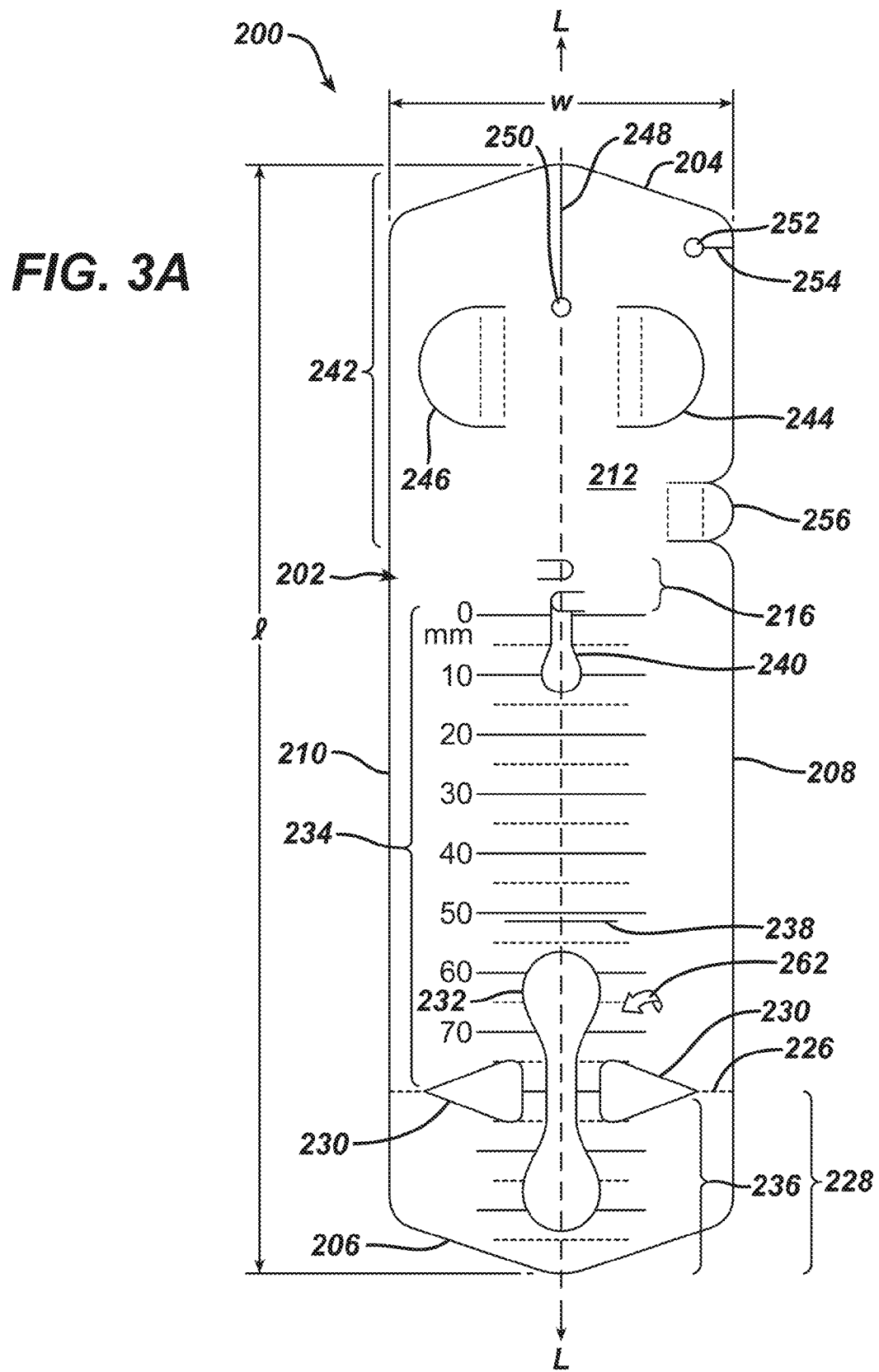
FIG. 3A is a top view of another exemplary embodiment of a surgical implant management device, the device being in an unfolded configuration.
Figure 3B:
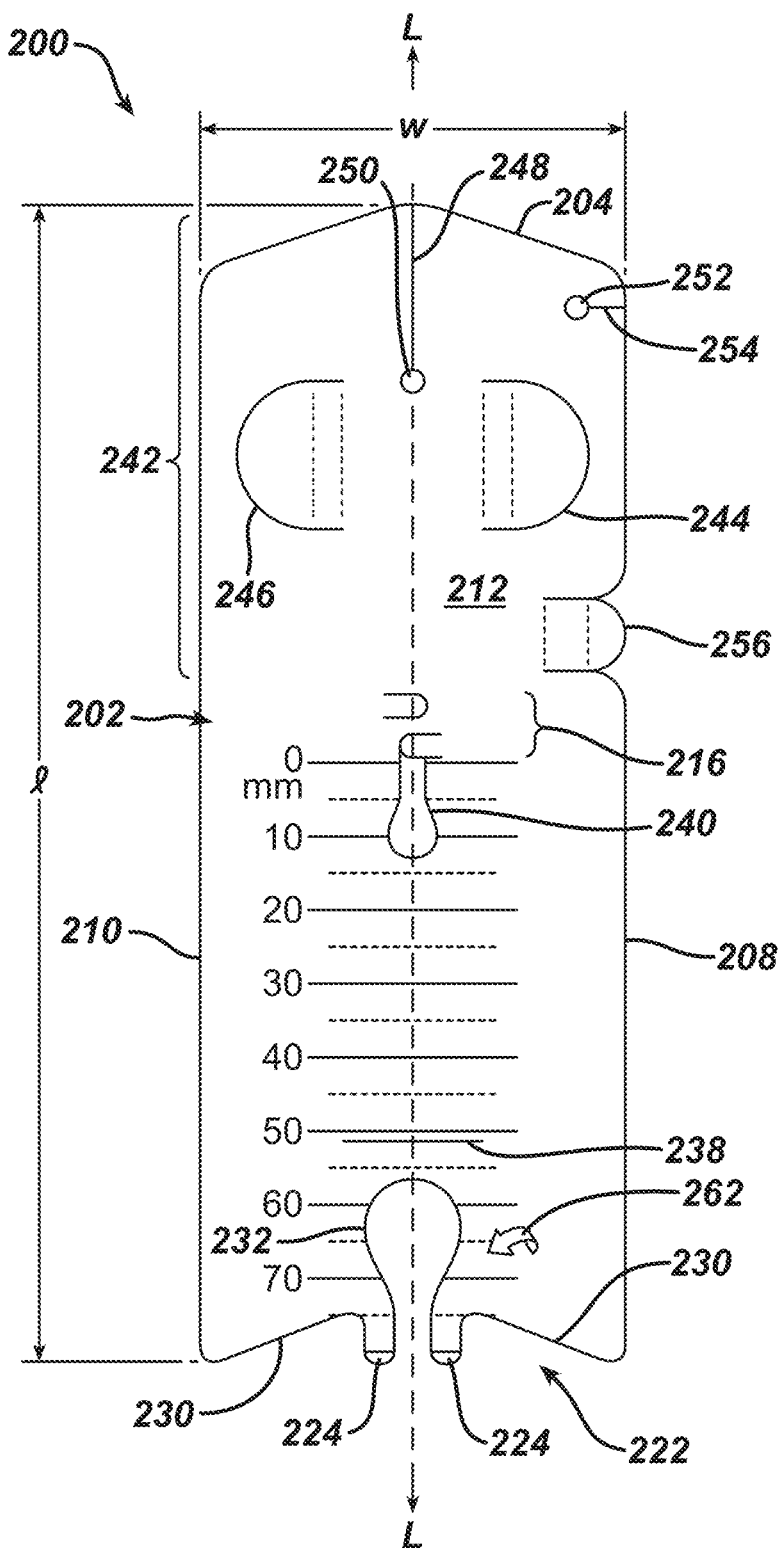
FIG. 3B is a top view of the device of FIG. 3A, the device being in a folded configuration.

FIGS. 3A and 3B illustrate an implant management device or card 200 in an unfolded configuration and a folded or compact configuration, respectively. The device 200 is similar to the device of FIGS. 2A-2D in that it has body 202 having a generally rectangular shape defined by a first end 204, a second end 206, and opposed walls 208, 210 extending between the two ends 204, 206, has a central longitudinal axis L extending a length of the body 202, and that it also includes a top side or surface 212 and a bottom side or surface 214 (not shown). The device further includes features such as an implantable body retainer 216, an alignment opening 240, prongs 224 formed as part of a filament loop engaging region 222 that results from folding a second portion 228 along a fold 226 and inserting the second end 206 into a retention slit 238, opposed openings 230, a graft-receiving opening 232, first indicia 234, second indicia 236, and filament retention features formed in a second filament receiving region 242, for example horizontally-disposed filament retention tabs 244, 246, a plurality of bores 250, 252 and slits 248, 254, and a retention tab 256.

Despite having many similar features, the device 200 of FIGS. 3A and 3B is significantly longer than the device 100 of FIGS. 2A-2D. As shown, in the unfolded configuration a length l of the device is approximately 220 millimeters, and in the folded configuration the length l is approximately 160 millimeters. The longer device 200 can allow for longer measurements to be designated on loops of an implant associated therewith because the fold 226 is approximately 80 millimeters away from the implantable body retainer 216. Longer devices can be useful for collateral ligament repairs, e.g., a medial collateral ligament ("MCL") or a medial patellofemoral ligament ("MPFL") repair, in which a length of an implant loop is typically larger, in the range of about 80 millimeters to about 120 millimeters. In some embodiments, a length of an implant loop can be about 80 millimeters, and in some other embodiments a length of an implant loop can be about 90 millimeters. Shorter devices like the device 100 can be useful for cruciate ligament repairs, e.g., an ACL or a posterior cruciate ligament ("PCL") repair, in which a length of an implant loop is typically no more than about 50 millimeters to about 70 millimeters. In some embodiments, a length of an implant loop can be about 60 millimeters.

Another feature included as part of the device 200 is an instructional marking, as shown an arrow 262. The arrow 262 can be located adjacent to the graft receiving opening 232, thereby indicating to a user that, in use, the ligament graft should be disposed in the opening 232. Other instructional markings can also be provided for on the top and bottom surfaces 212, 214, and some further, non-limiting examples of such markings are provided for in other embodiments. The instructional markings can be particularly useful when the device comes pre-packaged so a user can easily identify the various features and functionalities of the device.

Similar to the device 100, the retention slit 238 for receiving the second end 206 can be disposed between the first end 204 and the start of the graft-receiving opening 232. However, because in the illustrated embodiment the length of the second portion 228 is substantially similar to the length of the second portion 128 in the first device 100, but the length between the first end 204 and the fold 226 is substantially longer than in the device 100, the slit 238 is located further from the implantable body retainer 216 than is the comparable slit 138.

FIGS. 4-8 provide further alternative configurations of an implant management device. Unlike the previous two embodiments, these embodiments do not illustrate both an unfolded configuration and a folded or compact configuration. Although only a compact configuration is illustrated in the devices of FIGS. 4-8, the illustrated configurations can be the result of folding using techniques described herein or otherwise known to those skilled in the art. Alternatively, the illustrated configurations can be the only configurations of the body provided for, thus requiring no folding to result in the illustrated configurations.

Each of these alternative configurations of FIGS. 4-8 is for an implant management device 300, 400, 500, 600, 700 that has a body 302, 402, 502, 602, 702 having a generally rectangular shape defined by a first end 304, 404, 504, 604, 704, a second end 306, 406, 506, 606, 706, and opposed walls 308 and 310, 408 and 410, 508 and 510, 608 and 610, 708 and 710 extending between the two ends 304 and 306, 404 and 406, 504 and 506, 604 and 606, 704 and 706. Each also includes a top side or surface 312, 412, 512, 612, 712 and a bottom side or surface 314, 414, 514, 614, 714, and has a central longitudinal axis L extending a length of the body 302, 402, 502, 602, 702, the location of the axis L having being previously defined with respect to other embodiments. Because the illustrated embodiments are in a compact configuration, the second end 306, 406, 506, 606, 706 is illustrated as being located at the portion in the earlier embodiments identified as the fold 126, 226. Such identification does not preclude an unfolded configuration for the devices 300, 400, 500, 600, 700 having a second end that is retained in a retention slit as described with respect to the devices 100, 200.

Figure 4:
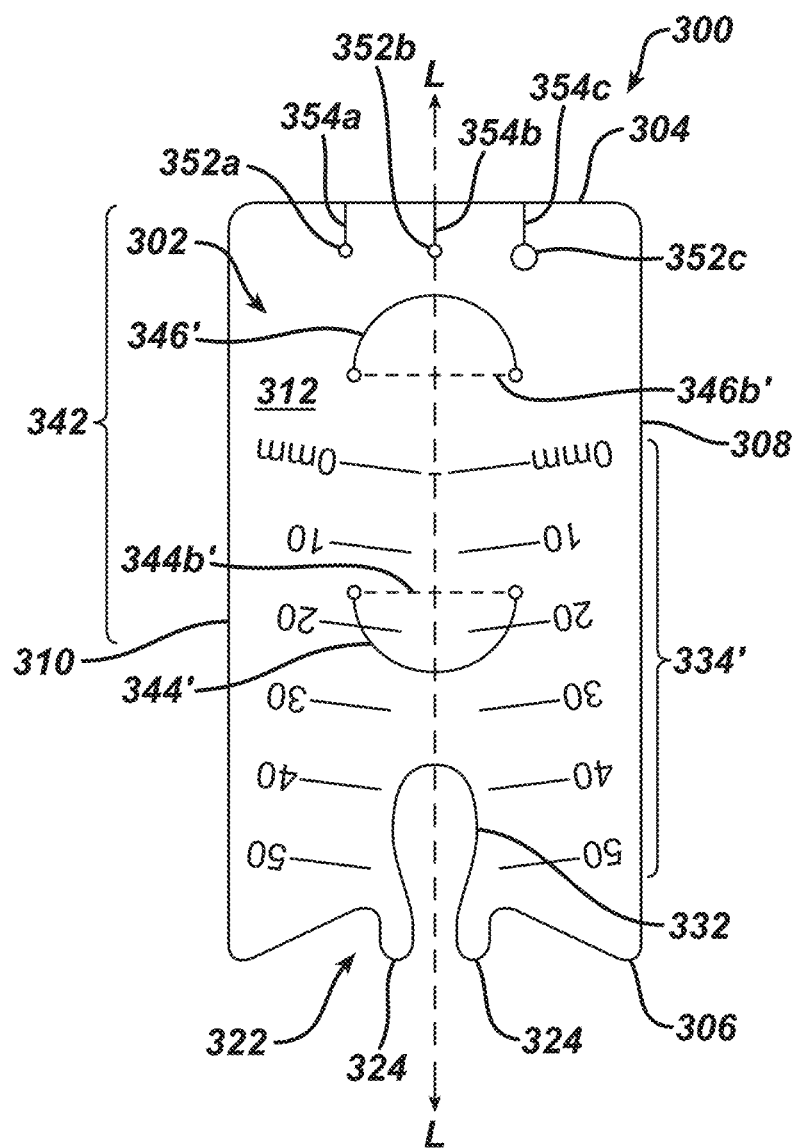
FIG. 4 is a top view of yet another exemplary embodiment of a surgical implant management device.

In the implant management device 300 of FIG. 4, the device 300 includes a filament loop engaging region 322, e.g., prongs 324, located at the second end 306, a graft-receiving opening 332, and indicia 334' located on the top surface 312. The illustrated embodiment does not include an implantable body retainer. Instead, a user can hold an implant at the 0 millimeter indicia line to mark loops and ligament grafts as desired. Additionally, as shown, the indicia 334' can be slightly angled as compared to an approximate straight line formed by the first end 304. The angled lines can allow for a more true representation of the anatomy of the loop being marked. However, it was found that in most instances any difference in the accuracy of making markings using straight lines versus angled lines for the indicia was negligible.

The implant management device includes a plurality of filament retention features for retaining filaments extending from the implant, e.g., adjustable limbs, a leading filament, and a trailing filament. The features can be formed in a second filament receiving region 342 of the body 302, and can include, for example, a pair of opposed tabs 344', 346'. The tabs 344', 346' in this embodiment are different than the tabs 144, 146 and 244, 246 both because they are formed differently and disposed in a different location.

The tabs 344', 346' are formed only from a single fold 344b', 346b'. The tabs 344', 346' can be bent to extend into or out of the page, and filaments can then be wrapped around the tabs 344', 346', proximate to the folds 344b', 346b'. Regarding their location, both tabs 344', 346' can be centrally disposed on the device 300 such that the central longitudinal axis L substantially bisects the tabs 344', 346'. Tabs extending in this direction can be referred to herein as being vertically-disposed with respect to the central longitudinal axis L. As shown, the two tabs 344', 346' are approximately equidistant from the 0 millimeter indicia line, although other locations are certainly possible, including some locations that are provided for herein. In some instances, filament that is wrapped around the tabs 344', 346' can help to maintain a location of an implant body in the absence of an implantable body retainer. Although there is no slit extending from one of the walls and towards the tabs 344', 346', like the slit 148, 248 of the devices 100, 200, such a slit can be included in alternative configurations of the device 300.

The second filament receiving region 342 can also include a plurality of bores formed therein, as shown three bores 352a, 352b, 352c, with each bore 352a, 352b, 352c having a slit 354a, 354b, 354c associated therewith extending from the first end 304. Each bore 352a, 352b, 352c can be used to retain a different filament. For example, the first bore 352a can be used to hold the adjustable limbs, the second bore 352b can be used to hold the leading suture, and the third bore 352c can be used to hold the trailing suture. By using each bore to hold a different filament, it can improve the ability for a user to distinguish between the various filaments, and can also help reduce the possibility of tangling between the filaments. In the illustrated embodiment, the third bore 352c has a diameter that is larger than the diameters of the first and second bores 352a, 352b, although any combination of diameter sizes, and any number of bores, can be used, depending, at least in part, on the number and size of the filaments associated with the implant.

Figure 5:
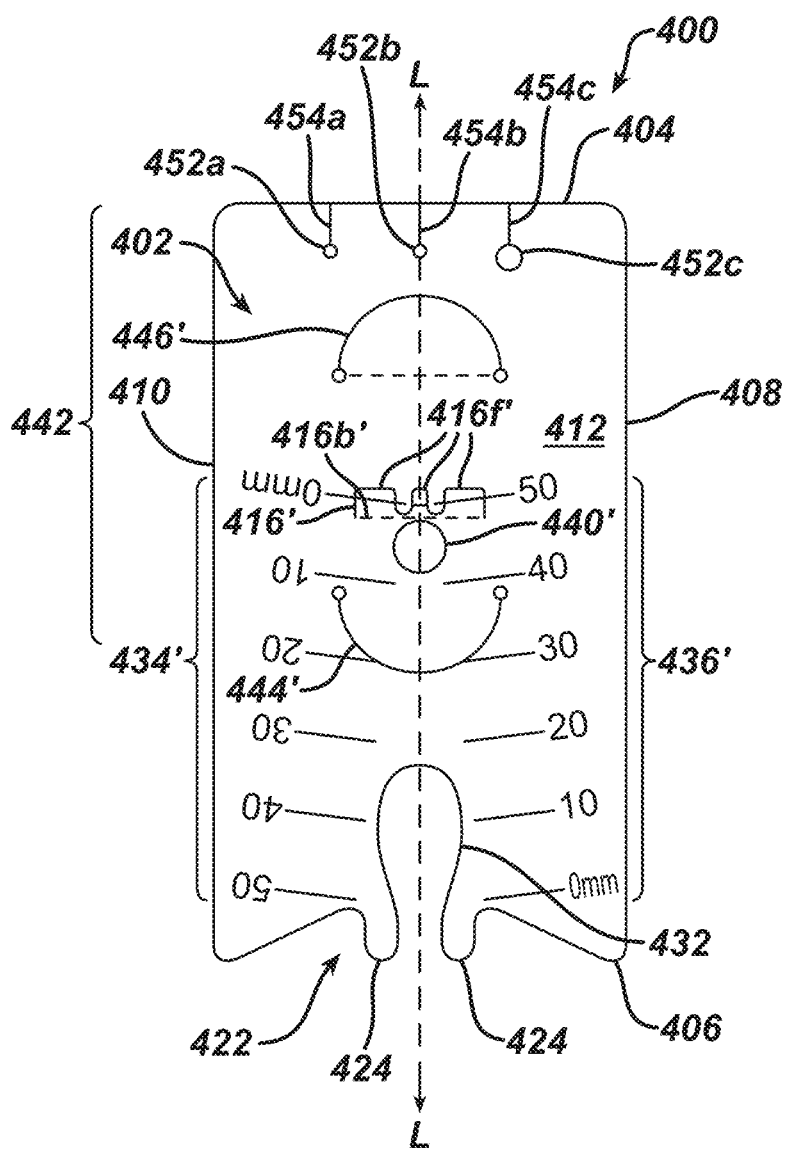
FIG. 5 is a top view of another exemplary embodiment of a surgical implant management device.

The device 400 illustrated in FIG. 5 is similar to the device 300 of FIG. 4 except that it includes an implantable body retainer 416', as well as an alignment opening 440' for integration with a graft preparation device. Further, the indicia 434', 436' provided for on the top surface 412 can be used in both directions. Features of the device such as the filament loop engaging region 422, e.g., prongs 424, the graft-receiving opening 432, and filament retention features formed in a second filament receiving region 442, for example the vertically-disposed filament retention tabs 444', 446' and the bores 452a, 452b, 452c and slits 454a, 454b, 454c, can be of a nature as described herein with respect to FIG. 4 and other disclosed embodiments.

The implantable body retainer 416' allows a body of an implant to extend approximately horizontally with respect to the central longitudinal axis L, i.e., a horizontal orientation. The previously described embodiments held the implant body in a vertical orientation. The tab of the implantable body retainer 416' can be configured to fold into or out of the paper along a fold 416b' to allow the implant body to be tucked underneath the tab. Further, in some embodiments, the tab can include one or more fingers 416f configured to make it easier for the user to grasp the tab 416'.

The alignment opening 440' provided for in FIG. 5 is substantially circular, as opposed to the more elongate configuration illustrated for the alignment openings 140, 240 of the devices 100, 200. A person skilled in the art will recognize that a variety of other shapes can be used to help integrate an implant management device with a graft preparation device, depending, at least in part, on the shape and size of a corresponding post on the graft preparation device.

The indicia 434', 436' on the top surface 412 are different than indicia of any of the previously described embodiments because they are both disposed in the same location and configured to allow for easy use in both directions on the same side of the device without needing to unfold the device 400. As shown, the first indicia 434' starts at 0 millimeters at the location of the implantable body retainer 416' and goes to 50 millimeters at a location proximate to the prongs 424, and the second indicia 436' starts at 0 millimeters at a location proximate to the prongs 424 and goes to 50 millimeters at the location of the implantable body retainer 416'. Providing the second indicia 436' at this location can allow for ligament graft measurements to be easily made based on indicia located on the top surface 412 in the compact configuration because the starting place for such measurements can generally occur at or near the second end 406.

Figure 6:
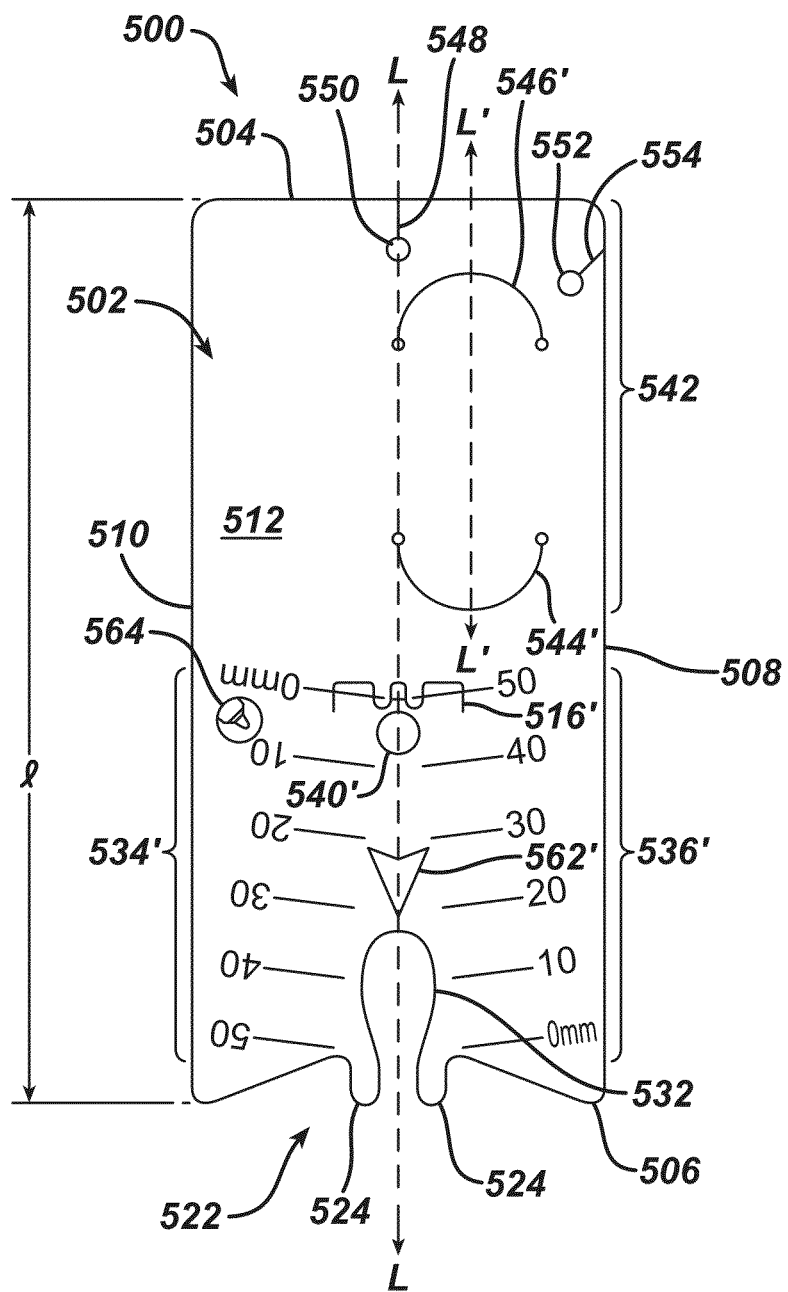
FIG. 6 is a top view of still another exemplary embodiment of a surgical implant management device.

FIG. 6 illustrates another embodiment of an implant management device 500. The device 500 is similar to the device 400 of FIG. 5 in that it includes an implantable body retainer 516', an alignment opening 540', a graft-receiving opening 532, prongs 524 formed as part of a filament loop engaging region 522, first and second indicia 534', 536', and filament retention features formed in a second filament receiving region 542, for example vertically-disposed filament retention tabs 544', 546'. Further, bores 550, 552 and slits 548, 554' similar to the bores 150, 152 and slits 148, 154 of the device 100 of FIGS. 2A-2D are also provided as filament retention features. Although the filament retention tabs 544', 546' of the device 500 are vertically disposed like the equivalent tabs 444', 446' of the device 400, they are disposed at a different location. Further, the device 500 provides for additional examples of instructional markings provided on the top surface 512.

As shown, filament retention tabs 544', 546' are still opposed to each other and a longitudinal axis L' that bisects the tabs 544', 546' is substantially parallel to the central longitudinal axis L, however, they are not centrally disposed on the device 500 as the tabs 444', 446' are in the device 400. Instead the tabs 544', 546' are offset to one side of the central longitudinal axis L, as shown at a location that is more proximate to the first wall 508 than the second wall 510. Further, a length l of the device is substantially longer than a length of the device 400, which allows for the filament retention tabs 544', 546' to be spaced a distance apart from the indicia 534', 536' formed on the top surface 512. As a result, it can be easier to view the indicia 534', 536' when filament is disposed around the filament retention tabs 544', 546' due to the wrapped filament not being disposed directly on any portion of the indicia 534', 536'.

The slit 548 and bore 550 can be used to assist in disposing filament around the filament retention tabs 544', 546'. The slit 548 can be formed in the first end 504, centrally disposed on the body 502 such that it extends a portion of the length of the central longitudinal axis L, substantially parallel to one terminal end of the tabs 544', 546'. The slit 548 can extend towards the filament retention tabs 544', 546', terminating at the bore 550 extending through the body 502. A portion of the filament can be passed through the slit 548 and disposed in the bore 550 prior to winding the filament around the tabs 544', 546'.

The second slit 554' and bore 552 combination can be formed along an edge of the body 502 to receive filament after it has been wound around the filament retention tabs 544', 546'. As shown, the second slit 554' can be formed in the first wall 508, proximate to a corner of the body 502. The slit 554' can extend diagonally with respect to the central longitudinal axis L, and can terminate at the second bore 552. Filament extending from the filament retention tabs 544', 546' can be passed through the slit 554' and disposed in the bore 552 to help manage the filament. Because the second slit 554' and bore 552 are disposed near the edge of the body 502, they help keep the filament out of the way of the user's view so the loop, ligament graft, and indicia 534', 536' can be more easily viewed.

The device of FIG. 6 further illustrates two additional instructional markings disposed on the top surface 512. One such marking is an alternative embodiment of an arrow 562' indicating to a user the location at which the ligament graft should be disposed. The arrow 562' serves a similar purpose as the arrow 262 of the device 200, but has a different look. A person skilled in the art will recognize a variety of other arrow types, and other types of instructions, that can be used to indicate where ligament grafts, or portions of the implant itself, should be disposed or otherwise placed when using the devices provided for herein. The second such marking is an image 564 of a writing instrument. The image 564 indicates to a user that this side of the device 500, i.e., the top side 512, can be used to mark indicators on any and all of the device itself, the implant, and the ligament graft.

Figure 7:
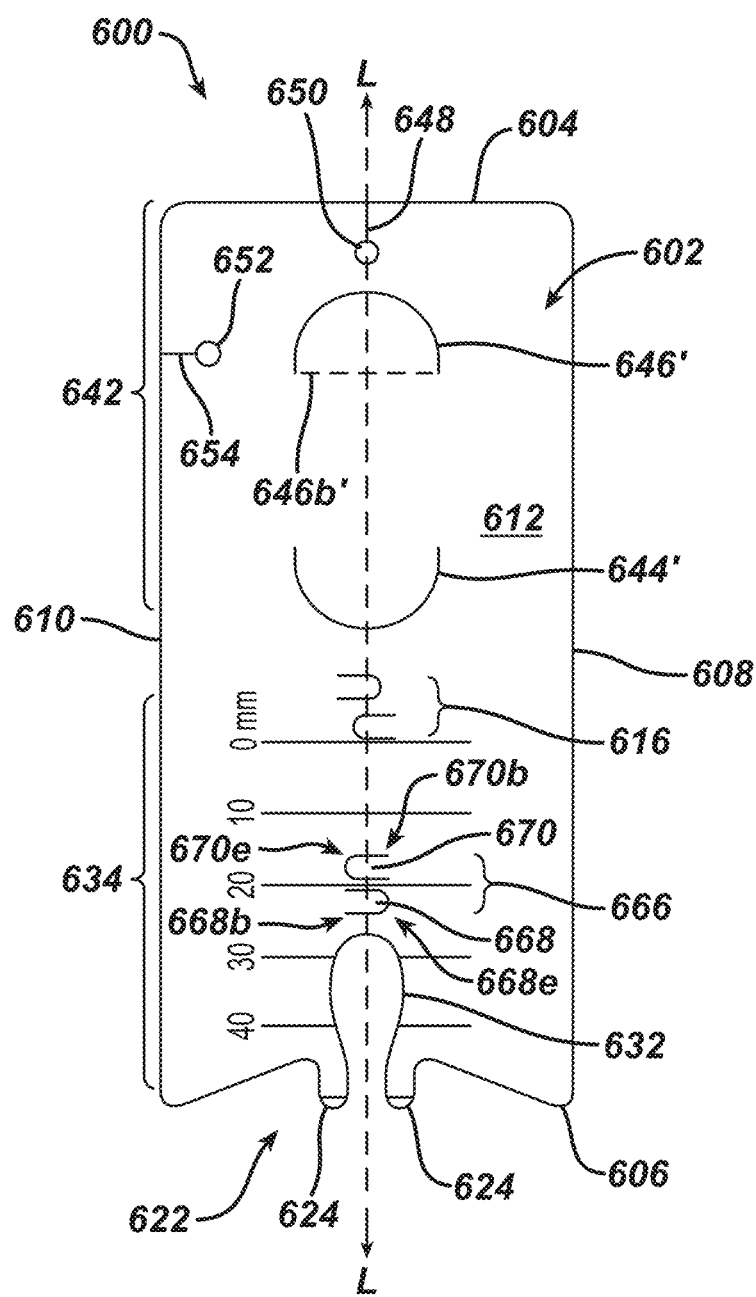
FIG. 7 is a top view of an exemplary embodiment of a surgical implant management device.

A further embodiment of an implant management device 600 is shown in FIG. 7. The device 600 includes some of the previously discussed features, including an implantable body retainer 616, a graft-receiving opening 632, prongs 624 formed as part of a filament loop engaging region 622, indicia 634, and filament retention features in a second filament receiving region 642, for example vertically-disposed filament retention tabs 644', 646' and bores 650, 652 and slits 648, 654, although the slit 654 is formed in the second wall 610 and the associated bore 652 is located proximate to the second wall 610. The vertically-disposed filament retention tabs 644', 646' are disposed centrally such that the central longitudinal axis L bisects the two tabs 644', 646', and they are spaced a distance apart from the indicia 634. The device further includes an additional filament management feature 666 located between the implantable body retainer 616 and the filament loop engaging region 622.

As shown, the feature 666 can include two staggered, opposed tabs 668, 670, similar to the tabs 118, 120 of the implantable body retainer 116 of the device 100. The tabs 668, 670 can be located between the implantable body retainer 616 and the graft-receiving bore 632. Both tabs 668, 670 can be configured to pivot at their respective bases 668b, 670b so that ends 668e, 670e of the tabs 668, 670 can be moved out of a plane that extends substantially through the body 602. As designed, both tabs 668, 670 pivot out of the page, thus allowing a portion of loops extending from a bottom side of an implant associated with the implantable body retainer 616 to be tucked underneath the tabs 668, 670 and held in place proximate to the top surface 612. The loops can then extend from the tabs 668, 670 and towards the prongs 624, still framing the graft-receiving opening 632 so that the loops can receive a ligament graft. The tabs 668, 670 can help prevent the various loops from becoming tangled with each other, and can help insure that each loop that is supposed to receive the ligament graft is properly positioned to do so. In the illustrated embodiment, the tabs 668, 670 are approximately centrally disposed such that they are substantially bisected by the longitudinal axis L. Further, as shown, the tabs 668, 670 can be substantially aligned longitudinally such that the base 668b of one tab 668 is approximately aligned with the end 670e of the other tab 670. In other embodiments the tabs 668, 670 can be aligned longitudinally such that the end 670e of the tab 670 terminates prior to the base 668b of the tab 668, similar to the alignment of the tabs 118 and 120 of the implantable body retainer 116 of the device 100.

The second slit 654 and second bore 652 are positioned on the body 602 such that they are aligned with a base 646b' of the tab 646'. As a result, a filament that is wrapped around the tabs 644', 646' can extend horizontally across the base of the tab 646' and directly into the second slit 654, and then into the second bore 652, for retention near the edge of the body 602. This alignment can help to alleviate undesirable tension in the filament while still keeping the filament out of the way of the user.

Figure 8:
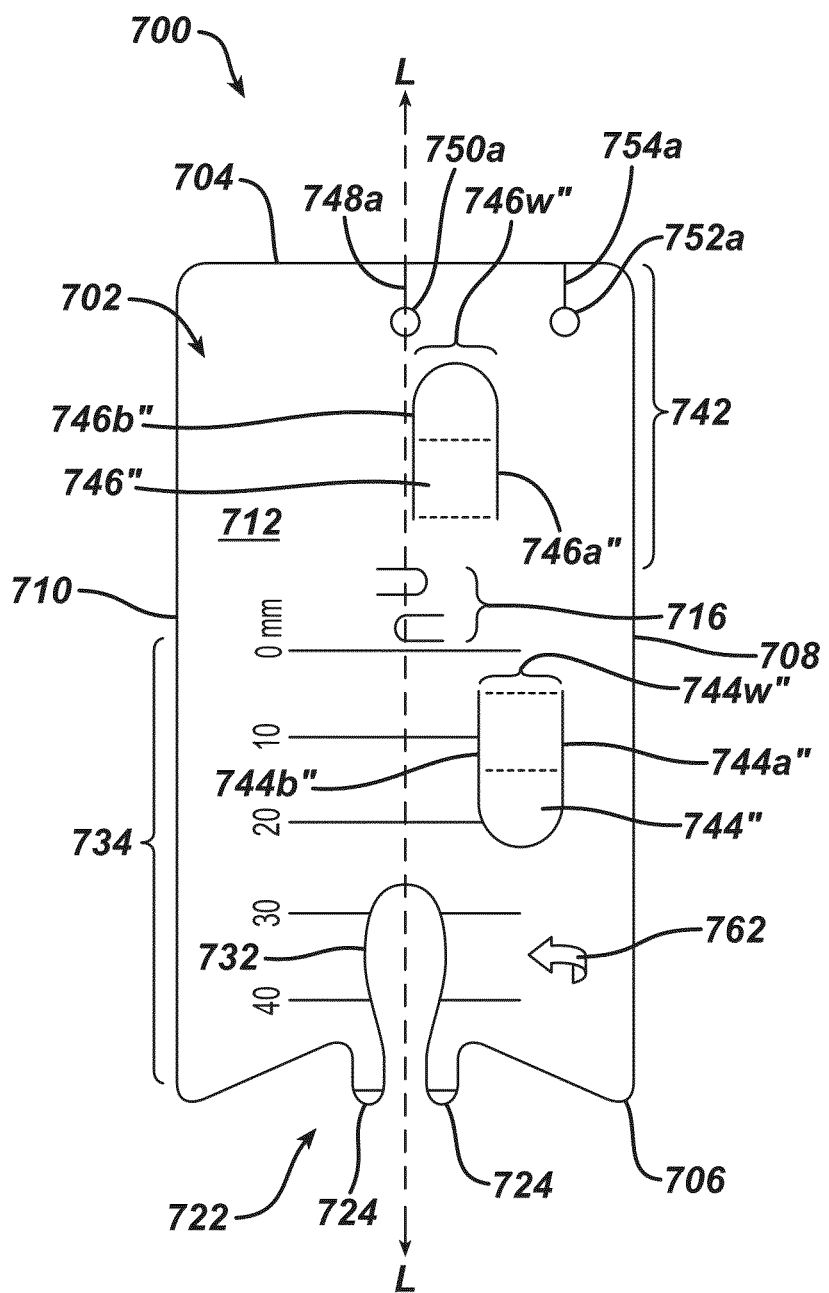
FIG. 8 is a top view of another exemplary embodiment of a surgical implant management device.

Yet a further configuration of an implant management device 700 is shown in FIG. 8. The device 700 includes some of the previously discussed features, including an implantable body retainer 716, a graft-receiving opening 732, prongs 724 formed as part of a filament loop engaging region 722, indicia 734, instructional markings such as an arrow 762, and filament retention features formed in a second filament receiving region 742, for example vertically-disposed filament retention tabs 744", 746" and bores 750a, 752a and slits 748a, 754a. The vertically-disposed filament retention tabs 744", 746" are different than in previous embodiments in that they are opposed but offset from each other.

As shown, each tab 744", 746" can include a first wall 744a", 746a" and a second wall 744b", 746b", with the second wall 744b" of the first tab 744" being close to vertically aligned with the first wall 746a" of the second tab 746". As also shown, the second wall 746b" of the second tab 746" can be approximately aligned with the central longitudinal axis L. Additionally, a width 744w", 746w" of the tabs 744", 746" can be smaller than a width of the comparable filament retention tabs in the previously described embodiments, e.g., filament retention tabs 144, 146 and 644', 646'. As shown, the width 744w", 746w" of each of the first and second tabs 744", 746" is approximately half the width of the comparable filament retention tabs in the previously described embodiments. However, because the tabs are offset from each other, the width formed by the distance between the first wall 744a" of the first tab 744" and the second wall 746b" of the second tab 746" can be approximately equal to a width of the comparable filament retention tabs of the previously described embodiments. As shown, two folds 744b", 744c" and 746b", 746c" can be formed in each tab 744", 746", with the folds 744b", 744c" and 746b", 746c" operating similar to the folds 144b, 144c and 146b, 146c of the tabs 144, 146 of the device 100.

The two slits 748a, 754a and bores 750a, 752a formed in the body 702 can operate in conjunction with the filament retention tabs 744", 746" to guide and/or maintain filament extending from a top side of an implant body associated with the device 700. The centrally-disposed slit 748a and bore 750a can be in substantial vertical alignment with the second wall 746b" of the second tab 746". The second slit 754a and bore 752a can be of a similar construction as the slit 748a and bore 750a, but as shown can be in substantial vertical alignment with the first wall 744a" of the first tab 744". Accordingly, a portion of filament can be passed through the centrally-disposed slit 748a and disposed in the bore 750a prior to winding the filament around the tabs 744", 746", and then another portion of the filament can be passed through the second slit 754a and disposed in the second bore 752a after winding the filament around the tabs 744", 746". The substantial vertical alignment of the slits 748a, 754a and bores 750a, 752a with the walls 746b" and 744a" can help prevent filament entanglement, as well as reduce unwanted tension in the filament. Further, because the second tab 746" intersects with a portion of the indicia 734, the reduced size of the tab 746", and the fact that it is offset with respect to the center of the body 702, can reduce any visual impairment caused by folding the tab 746" downward (into the page) in use. This configuration can also help reduce any visual impairment that results to indicia formed on a bottom side of the body 702, for instance indicia to assist in making measurements on a ligament graft.

Figure 9:
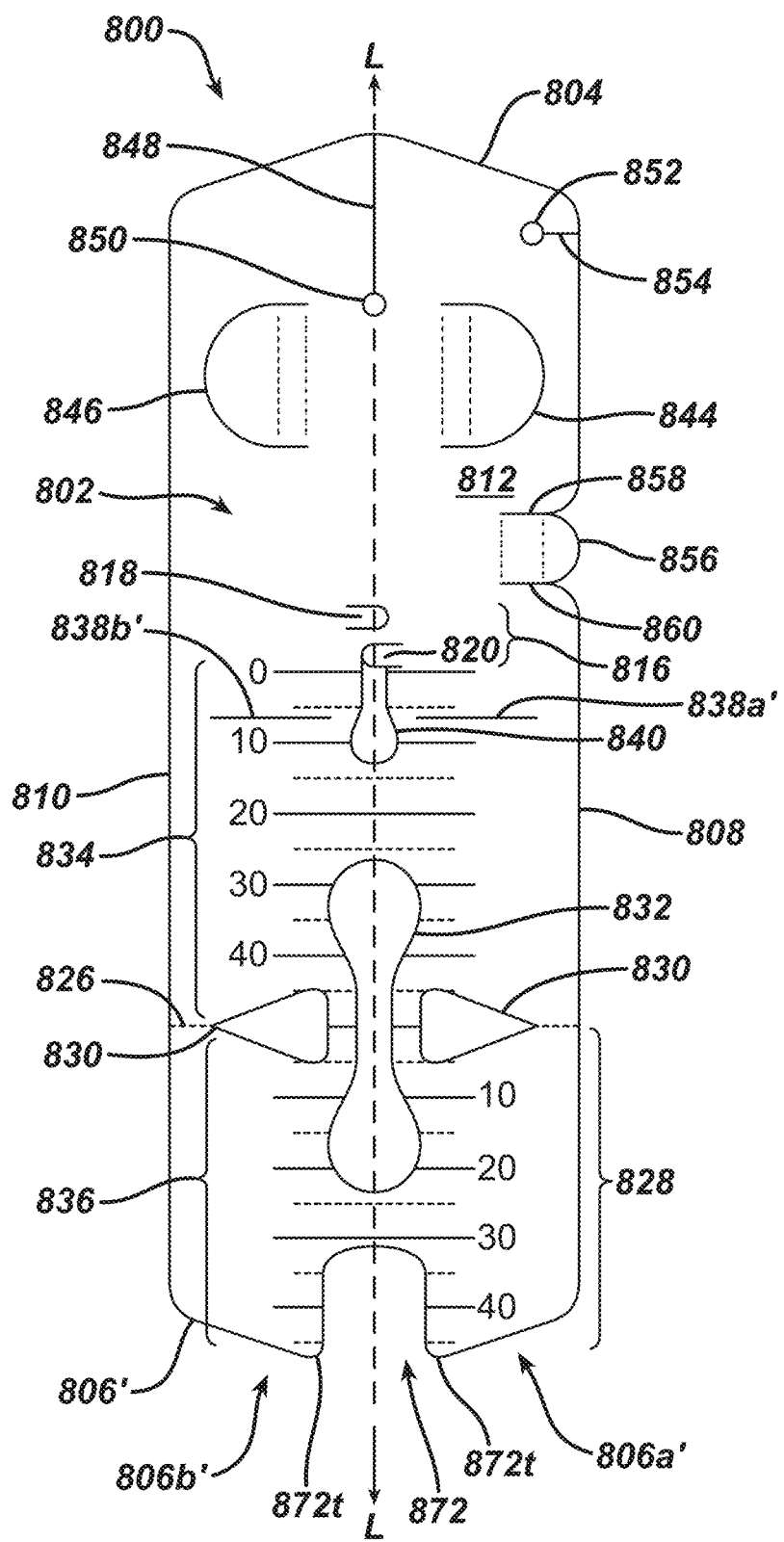
FIG. 9 is a top view of yet another exemplary embodiment of a surgical implant management device, the device being in an unfolded configuration.
Figure 10A:
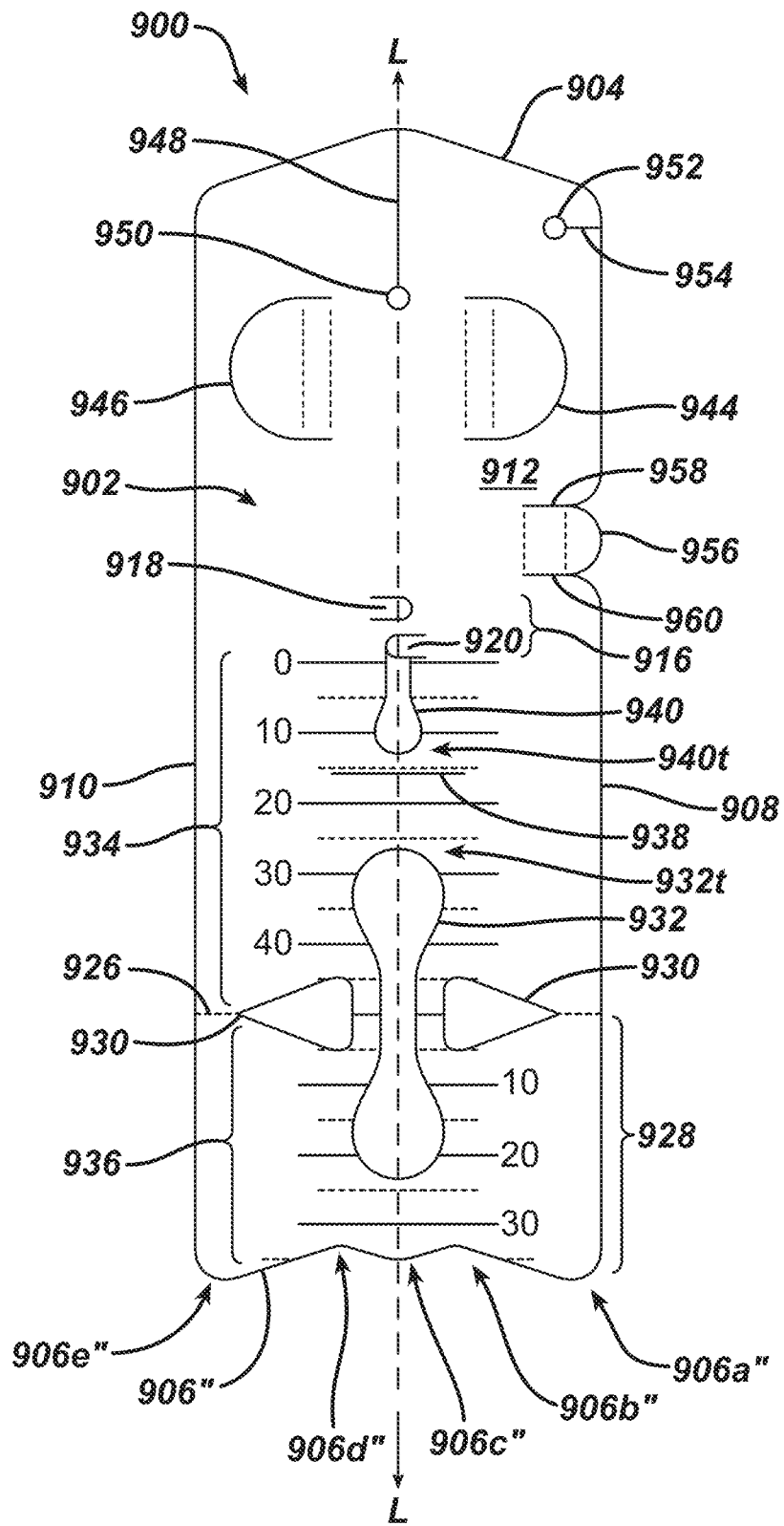
FIG. 10A is a top view of another exemplary embodiment of a surgical implant management device, the device being in an unfolded configuration.

FIGS. 9 and 10A provide for two alternative implant management devices 800, 900 in an unfolded configuration that illustrate non-limiting examples of differently shaped second ends 806', 906", respectively. Generally, the devices 800, 900 include many of the same features illustrated with respect to the devices 100, 200 of FIGS. 2A-2D and 3A-3B. Thus, as shown, the devices 800, 900 both have a body 802, 902 having a generally rectangular shape defined by a first end 804, 904, a second end 806', 906", and opposed walls 808, 810 and 908, 910 extending between the two ends 804, 806' and 904, 906", respectively. Each device 800, 900 further includes a central longitudinal axis L extending a length of the body 802, 902, and further includes a top side or surface 812, 912 and a bottom side or surface 814, 914 (not shown). Additional features provided for in the devices can include an implantable body retainer 816, 916 having opposed tabs 818, 820 and 918, 920, an alignment opening 840, 940, a second portion 828, 928 configured to be folded along a fold 826, 926 toward the bottom side 814, 914, i.e., into the page, to form a filament loop engaging region that includes prongs, opposed openings 830, 930, a graft-receiving opening 832, 932, first indicia 834, 934, second indicia 836, 936, and filament retention features formed in a second filament receiving region 842, 942, for example horizontally-disposed filament retention tabs 844, 846 and 944, 946, a plurality of bores 850, 852 and 950, 952 and slits 848, 854 and 948, 954, and a retention tab 856, 956 having slits 858, 860 and 958, 960.

As shown in FIG. 9, in one alternative embodiment, the second end can include a U-shaped cut-out 872. Two tapered edges 806a', 806b' can extend from terminal ends 872t of the cut-out 872 and to the opposed walls 808, 810. When the body 802 is folded along the fold 826 such that the second portion 828 moves into the page, towards the bottom side 814, the two tapered edges 806a', 806b' can be disposed in complementary retention slits 838a', 838b' formed in the body 802 between the fold 826 and the first end 804. As shown, the retention slits 838a', 838b' are disposed in-line with a portion of the alignment opening 840, proximate to the implantable body retainer 816 because the length of the second portion 828 is almost the same length as the length extending from the 0 millimeter indicia line to the fold 826. The U-shaped cut-out 872 helps prevent the body 802 from interfering with a graft preparation device by allowing the alignment opening 840 to be unobstructed. Thus, this configuration can be useful when the indicia 826 on the second portion 828 are provided for a length that is long enough to interfere with other features of the device 800, implant, or other structures used in conjunction with the same, e.g., a graft preparation device.

The alternative embodiment of FIG. 10A provides for a second end 906" that has a jagged shape. In the illustrated embodiment the second end 906" has an M-shape or W-shape such that three terminal peaks 906a", 906c", 906e" and two terminal valleys 906b", 906d" exist. A retention slit 938 formed between the fold 926 and the first end 904 can be configured to receive a portion of the second end 906" extending between the two terminal valleys 906b", 906d", including the central terminal peak 906c". Again, the location of the slit 938 can depend on the length of the second portion 928 folded towards the bottom side 914, i.e., into the page. In the illustrated embodiment, the retention slit 938 is more proximate to a terminal end 940t of the alignment opening 940 than a terminal end 932t of the graft-receiving opening 932.

FIG. 10B provides an alternative embodiment of a device 900' that is generally configured like the device 900 of FIG. 10A, but includes a differently configured implantable body retainer 916' and a differently configured filament retention feature, more particularly retention tabs 956a', 956b', which are differently configured than the retention tab 956 of FIG. 10A. As shown, opposed tabs 918', 920' of the implantable body retainer 916' of FIG. 10B have a larger surface area than the tabs 916, 918 of the device 900 of FIG. 10A. These larger tabs 918', 920' allow for a larger implant body to be more easily retained by the device 900'. A larger implant body can be used for surgeries requiring larger bone holes, or alternatively, in instances in which a surgeon drills a bone hole larger than originally anticipated. In such instances a length or diameter of the implant body can be configured to be larger than the diameter of the bone hole, and thus preventing the implant body from falling into the bone hole and the implant from losing its implant location.

The retention tabs 956a', 956b' serve a similar purpose as the retention tab 956, and thus can retain excess filament that extends from a top side of an implant body. While many configurations can be used to retain a filament, in the illustrated embodiment the tabs 956*a*', 956*b*' are configured in a manner similar to opposed tabs of implantable body retainers provided for herein, e.g., the opposed tabs 918, 920 of FIG. 10A or the opposed tabs 668, 670 of FIG. 7. As shown, the tabs 956*a*', 956*b*' are located proximate to a wall 908' of the body 902', thereby keeping the filament disposed away from indicia 934' formed on a top surface 912' of the body 902', and are staggered with respect to each other. Both tabs 956*a*', 956*b*' can be configured to pivot at their respective bases 956*ab*', 956*bb*' so that ends 956*ae*', 956*be*' of the tabs 956*a*', 956*b*' can be moved out of a plane that extends substantially through the body 902'. As designed, both tabs 956*a*', 956*b*' pivot out of the page, thus allowing filament to be tucked underneath the tabs 956*a*', 956*b*' and be supported by other portions of the top surface 912'. In the illustrated embodiment, the tabs 956*a*', 956*b*' are substantially aligned longitudinally such that the base 956*ab*' of one tab 956*a*' is approximately aligned with the end 956*be*' of the other tab 956*b*'. Likewise, the base 956*bb*' tab 956*b*' is approximately aligned with the end 956*ae*' of the tab 956*a*'. In other embodiments the tabs 956*a*', 956*b*' can be aligned longitudinally such that an end of one tab, such as the end 956*be*' of the tab 956*b*', terminates prior to a base of the other tab, such as the base 956*ab*' of the tab 956*a*'.

FIG. 11 illustrates another embodiment of an implant management device or card 1000 in an unfolded configuration. This card 1000 is particularly designed to provide instructions on the card itself to assist a user in transforming the unfolded card into a folded card having an implant stored thereon and a ligament graft associated therewith. In particular, an increasing number of dots 1076, 1078, 1080, and 1082 are provided for on a top surface 1012 to indicate the order of steps to be performed by the user to fold the card 1000, add an implant, add a ligament graft, and store filaments associated with the implant on the card 1000.

As shown, the card 1000 has a body 1002 having a generally rectangular shape defined by a first end 1004', a second end 1006, and opposed walls 1008, 1010 extending between the two ends 1004', 1006. The card 1000 has a central longitudinal axis L extending a length of the body 1002, and also includes a top surface 1012 and a bottom surface 1014 (not shown). A pair of folds 1025, 1026 are provided that extend substantially horizontal to the central longitudinal axis L, dividing the unfolded configuration into a first section 1074*a*, a second section 1074*b*, and a third section 1074*c*.

A first dot 1076 is provided proximate to an implantable body retainer 1016", which itself is located approximately centrally on the second section 1074*b*. The implantable body retainer 1016" in the illustrated embodiment is configured differently than previously described implantable body retainers. As shown, the implantable body retainer 1016" is a single vertical slit that extends substantially in-line with the central longitudinal axis L. The first step indicated by the first dot 1076 can include passing an implant body through the slit of the implantable body retainer 1016", from the top side 1012 to the bottom side 1014, while keeping at least a portion of the filament extending therefrom on the top side 1012. The filament that forms the loops of the implant can extend from the implant body through a first bore 1015" formed at a terminal end of the vertical slit, and filament from adjustable limb(s), a leading suture, and a trailing suture can extend from the implant body through a second bore 1017" formed at an opposite terminal end of the vertical slit. This configuration can thus hold an implant in place on the card 1000. In the illustrated embodiment, the second bore 1017" has a larger diameter than a diameter of the first bore 1015" because the second bore 1017" can be configured to hold a greater thickness of filament therein, although other sizes of bores can be used depending, at least in part, on the type, number, and thickness of the filaments associated with the implant.

The location of the implant body once situated on the card 1000 can typically be such that the portion of the loop closest to the implant body is substantially aligned with the 0 millimeter indicia line to insure accurate markings on the device, ligament graft, and/or implant. In the illustrated embodiment, the indicia 1034' on the top surface 1012 extend diagonally with respect to the central longitudinal axis L. Additionally, as shown, an instructional marking of an image 1064 of a writing instrument is provided to illustrate that a user can use the indicia 1034' to mark indicators on any and all of the device itself, the implant, and the ligament graft.

Two dots 1078 can be located on the second portion 1074*b*, proximate to the fold 1026. The two dots 1078 could just as easily be located on the third portion 1074*c*, proximate to the fold 1026. An arrow 1084 can be located next to the two dots 1078, and can be configured to illustrate that the second step includes folding the third portion 1074*c* towards the bottom side 1014, i.e., into the page in the illustrated embodiment. As a result, indicia 1036 on the third portion 1074*c*, which as shown are substantially perpendicular to the longitudinal axis L, are disposed on the bottom surface 1014 for purposes as described elsewhere herein. The second end 1006, which is part of the third portion 1074*c*, can include a central flap 1007 having a rounded edge that is configured to be received by a receiving slit 1038 formed on the second portion 1074*b*. Similar to other embodiments, the receiving slit 1038 can be disposed between a graft-receiving opening 1032 and the first end 1004'. In this embodiment, the slit 1038 is actually located between the second bore 1017" and the second fold 1025 because the length of the third portion 1074*c* is so long.

The first fold 1026 can substantially bisect the graft-receiving opening 1032, and thus folding the third portion 1074*c* onto the second portion 1074*b* results in an opening similar to the openings described in other embodiments herein. Unlike previously described embodiments, however, there are not two triangularly-shaped openings also bisected by the fold 1026. Instead, opposed, matching openings 1030' formed equidistant from the central longitudinal axis L terminate at the fold 1026 such that when the third portion 1074*c* is folded onto the second portion 1074*b*, a portion of the third portion 1074*c* obstructs the openings 1030' from the bottom side 1014. Nevertheless, loops from an implant can still be disposed on the two prongs 1024 that are formed as a result of folding the third portion 1074*c* onto the second portion 1074*b* at least because of the pliable nature of the card 1000. The prongs 1024 can hold the loops in a tensioned state and the illustrated configuration allows the loops to receive a ligament graft disposed in the graft-receiving opening 1032.

Three dots 1080 can be located on the third portion 1074*c*, adjacent to an arrow 1062' that points towards the graft-receiving opening 1032. The three dots 1080 can indicate that the third step is to dispose a ligament graft through the graft-receiving opening 1032, thus being received by loops of the implant being tensioned by the prongs 1024. An image of a ligament graft 1086 can also be provided on the top surface 1012 to help illustrate the purpose of the arrow 1062'.

Filaments extending from a top side of an implant body, which can include adjustable limb(s), a leading suture, and a trailing suture, can be configured to extend from the implantable body retainer 1016" and towards the first portion 1074*a*. The first portion 1074*a* can include one or more filament retention features. As shown, filament retention features of the card 1000 include a centrally disposed slit 1048 and bore 1050, as well as two opposed, substantially V-shaped cutouts 1088 formed in first and second walls 1008, 1010 of the body 1002. The filaments can be passed through the slit 1048 and a portion thereof can be held in the bore 1050, and then a remaining portion of the filament can be wrapped around the two V-shaped cutouts 1088 in a direction substantially perpendicular to the central longitudinal axis L.

Four dots 1082 can be located on the second portion 1074b, proximate to the fold 1025. The four dots 1082 could just as easily be located on the first portion 1074a, proximate to the fold 1025. An arrow 1090 can be located next to the four dots 1082, and can be configured to illustrate that the fourth step includes folding the first portion 1074a towards the bottom side 1014, i.e., into the page in the illustrated embodiment. Alternatively, the first portion 1074a could be folded towards the top side 1012, i.e., out of the page in the illustrated embodiment. The first end 1004' can include a central flap 1005' having a rounded edge that is configured to be received by a second receiving slit 1039' formed on the second portion 1074b. As shown, the second receiving slit 1039' can be proximate to the first receiving slit 1038, although the location of both slits can be dependent on the size of the first and third portions 1074a, 1074c that they are configured to receive.

By folding over the first portion 1074a, a portion of the filaments wrapped around the V-shaped cutouts 1088 can be protected from unintended fraying or cutting because a portion of the filaments is disposed between the two portions 1074a, 1074b. A centrally located diamond-shaped opening 1092 can be provided between the first and second portions 1074a, 1074b, which becomes a V-shaped opening when the first portion 1074a is folded onto the second portion 1074b. The diamond-shaped opening 1092 can help provide a desired amount of tension to the filaments as they are moved closer to the implant body when the first portion 1074a is folded towards the second portion 1074b. As a result, the filaments do not loosen undesirably and get in the way of the user during operation.

A person skilled in the art will recognize that instructions of the nature described with respect to the card 1000 can be applied to devices and cards having a variety of configurations and a variety of different features, e.g., bores, openings, slits, tabs, without departing from the spirit of the present disclosure. Further, a person skilled in the art will recognize that the number, amount, and type of instructions can change depending, at least in part, on the configuration of the card and the type of procedure with which the card is being used, and thus instructions that include more, fewer, or different steps can be derived from the disclosures contained herein. The teachings of instructions provided for herein can easily be adapted for any and all of the device and card configurations disclosed herein, derivable therefrom, or for other configurations of implant management devices and cards known to those skilled in the art.

Figure 12:
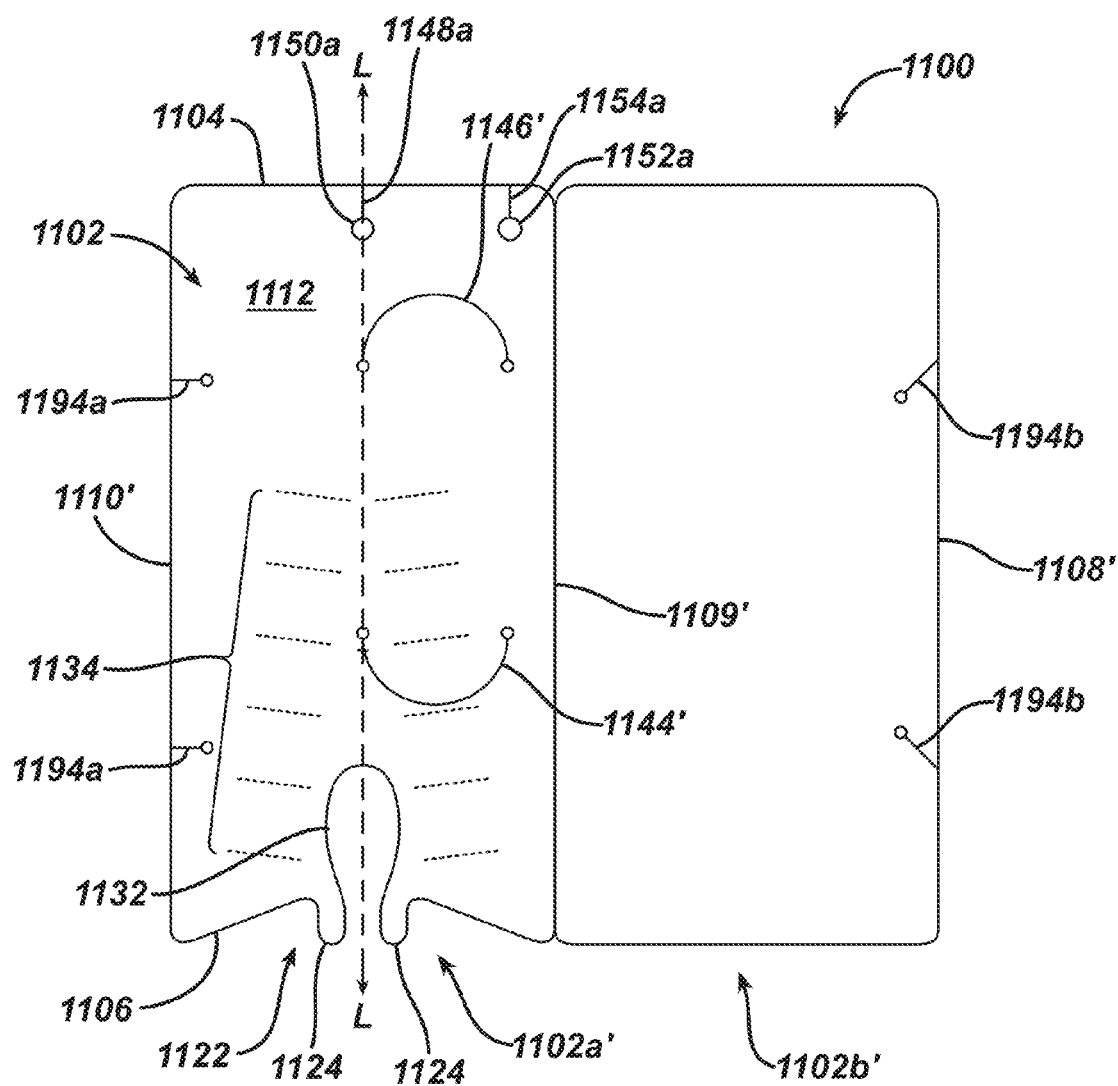
FIG. 12 is a top view of another exemplary embodiment of a surgical implant management device, the device being in an unfolded configuration.

FIG. 12 is another example of an implant management device 1100 in an unfolded configuration that can be folded to protect at least a portion of the implant. Protecting portions of the implant can be useful when packaging the implant and implant management device for distribution and sale, or alternatively, at the location of a surgical procedure prior to and during the procedure to prevent unintended fraying or cutting of filaments associated with the implant.

As shown, the implant 1100 has a body 1102 having a generally rectangular shape defined by a first end 1104, a second end 1106, and opposed walls 1108', 1110' extending therebetween. The body 1102 includes two portions 1102a' and 1102b' divided by a fold 1109'. As shown, the fold 1109' extends substantially parallel to the central longitudinal axis L, with the central longitudinal axis L in this embodiment being disposed centrally through the first portion 1102a'. The second section 1102b' can be folded toward a bottom side 1114 (not shown) of the first section 1102a', i.e., into the page, such that filament wrapped around vertically-disposed filament retention tabs 1144', 1146' can be protected between the first and second sections 1102a', 1102b'. First and second locking slits 1194a, 1194b can be formed in the first and second walls 1108', 1110', respectively, to allow the second portion 1102b' to be secured to the first portion 1102a'. As shown, the first locking slits 1194a extend substantially perpendicularly to the central longitudinal axis L and the second locking slits 1194b extend substantially diagonally with respect to the central longitudinal axis L. One of the portions 1102a', 1102b' can be twisted at the location of the slits 1194a, 1194b to allow one slit to engage the other, thereby forming a secure, interlocking connection. A person skilled in the art will recognize other ways by which a locking connection can be formed between two portions 1102a', 1102b'. Additionally, the device 1100 can include some of the same features described in previous embodiments, including a filament loop engaging region 1122, e.g., prongs 1124, located at the second end 1106, a graft-receiving opening 1132, indicia 1134 located on a top surface 1112 of the body 1102, and filament retention features, for example vertically-disposed filament retention tabs 1144', 1146' and bores 1150a, 1152a and slits 1148a, 1154a.

Figure 13:
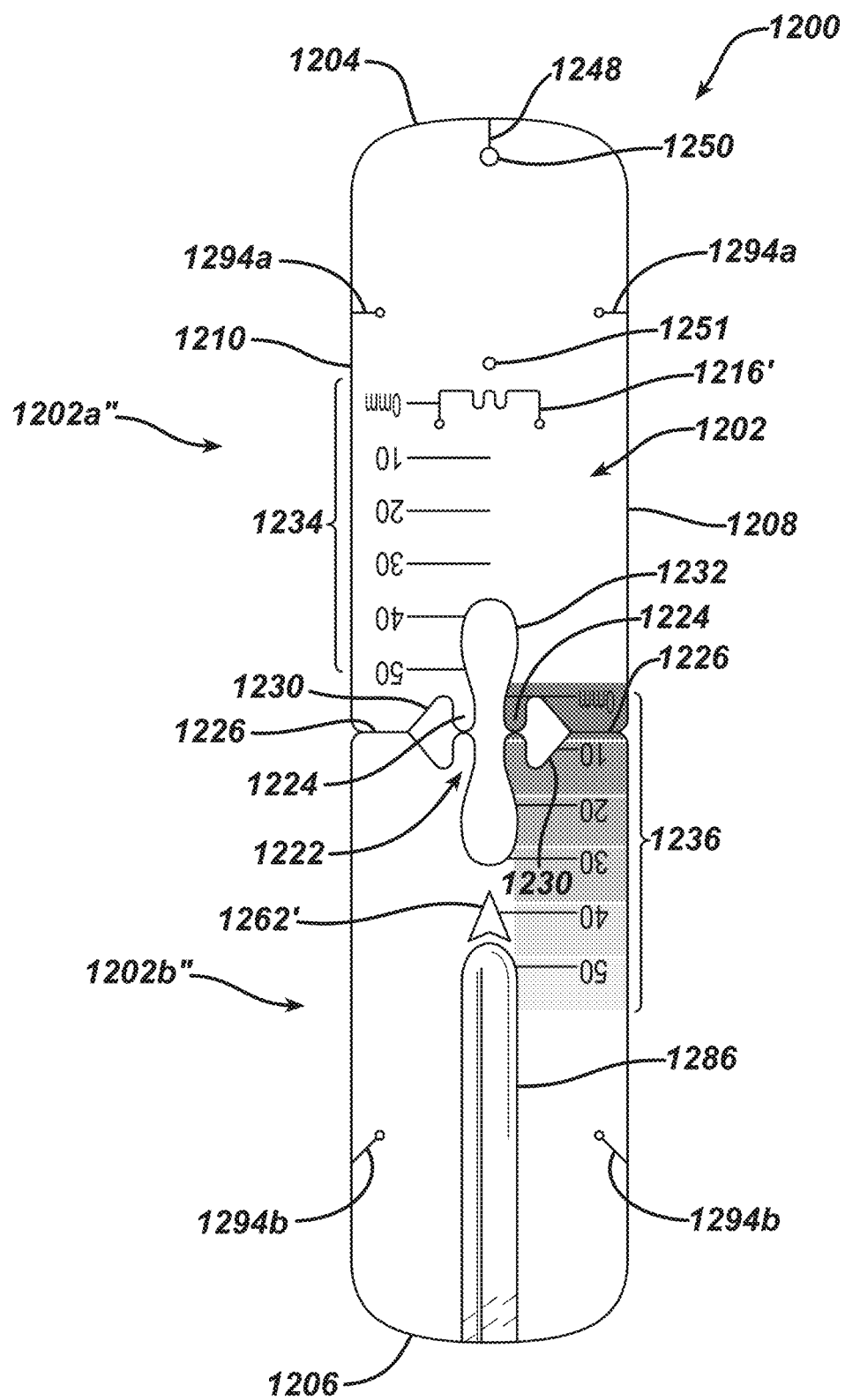
FIG. 13 is a top view of yet another exemplary embodiment of a surgical implant management device, the device being in an unfolded configuration.

The implant management device 1200 of FIG. 13 provides yet another embodiment of a device that can be folded to protect at least a portion of the implant. The device 1200 as shown has a body 1202 having a generally rectangular shape defined by a first end 1204, a second end 1206, opposed walls 1208, 1210 extending between the two ends 1204, 1206, a central longitudinal axis L extending a length of the body 1202, and a top side or surface 1212 and a bottom side or surface 1214 (not shown). As shown, the body 1202 includes two portions 1202a'' and 1202b'' divided by a fold 1226, and the fold 1226 extends substantially perpendicular to the central longitudinal axis L. The second section 1202b'' can be folded toward the bottom side 1214, i.e., into the page, such that the second end 1206 is located proximate to the first end 1204. A first locking slit 1294a can be formed in each of the first and second walls 1208, 1210 of the first portion 1202a'', and a second locking slit 1294b can also be formed in each of the first and second walls 1208, 1210 of the second portion 1202b''. The locking slits 1294a, 1294b can operate in a manner similar to the locking slits 1194a, 1194b of the device 1100, thereby forming a secure, interlocking connection between the first and second portions 1202a'' and 1202b''. As a result, any filament stored on the bottom side 1214 of the first portion 1202a'' can be protected by the second portion 1202b''. Features such as an implantable body retainer 1216', a graft-receiving opening 1232, a filament loop engaging region 1222 that includes prongs 1224 and opposed openings 1230, first and second indicia 1234, 1236, and instructional markings, such as an arrow 1262' and an image 1286 of a ligament graft, can be similar to those features previously described.

The device 1200 also includes filament retention features. In the illustrated embodiment, the filament retention features include a centrally disposed slit 1248 terminating in a centrally disposed bore 1250, and a second centrally disposed bore 1251, proximate to the implantable body retainer 1216'. As discussed in further detail below with respect to FIG. 14B, the bore 1251 can be used in conjunction with a filament management device 1400 to help retain excess filament. The slit 1248 and bore 1250 can be used in a manner as described with respect to other embodiments to help retain and direct excess filament toward the filament retention feature resulting from using the bore 1251 in conjunction with the filament management device 1400 of FIG. 14B. In alternative embodiments, the excess filament can be retained only by slit 1248 and bore 1250 and/or excess filament can remain relatively free while being disposed between the first and second portions 1202a'', 1202b''.

Although the illustrated embodiments of implant management devices are described as having a generally rectangular shape, a person skilled in the art will recognize other shapes that can be used to include the various device features provided for herein. Further, any and all of the implant management devices provided for herein can be made from a variety of different materials. In some exemplary embodiments, the devices are formed from a polymer, such as polyolefin or high density polyethylene because of its water-proof nature. Other non-limiting examples of materials that can be used to form implant management devices include metals, paper-based materials (e.g., paperboard, cardboard), and bio-compatible materials. Optionally, the device can be coated with one or more water-proof materials. One exemplary, non-limiting method for forming the implant management device is to die-cut a sheet of polyethylene. A weight of the implant management device itself can be approximately in the range of about 0.05 ounces to about 1.0 ounces. This amount of weight provides a desired amount of stability during the graft preparation stages. Further, a variety of different techniques and types of materials can be used to mark or otherwise provide indicia, instructions, or other markings on the implant management devices. By way of non-limiting examples, techniques for providing indicia, instructions, or other markings can include printing using ink, etching, embossing, and providing laser markings. For embodiments that include printing on the implant management devices, various inks, including waterproof inks such as Tampapur TPU 980 2-part epoxy ink from Marabu GmbH & Co. KG of Tamm, Germany, or other medical grade and/or bio-compatible inks can be used.

Filament Management Devices

Figures 14A, 14B:
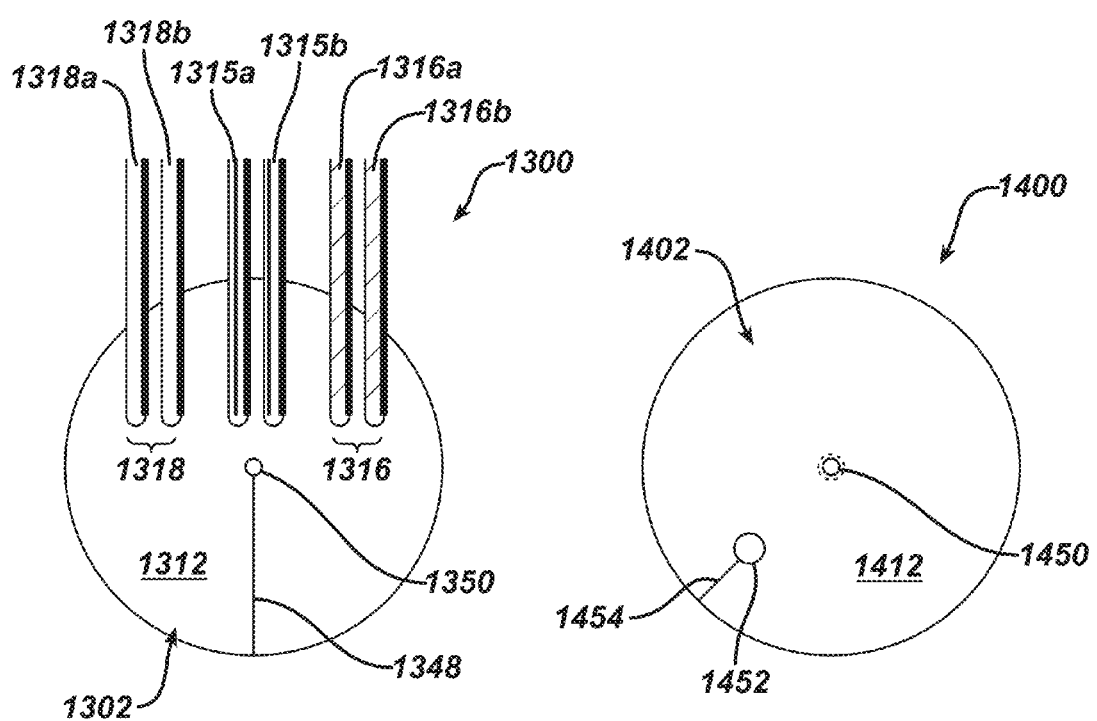
FIG. 14A is one exemplary embodiment of a filament management device for use with a surgical implant management device.
FIG. 14B is another exemplary embodiment of a filament management device for use with a surgical implant management device, for example the surgical implant management device of FIG. 13.

FIG. 14A illustrates one exemplary embodiment of a filament management device 1300 that can be used in conjunction with the implant management devices provided for herein or otherwise known in the art. The device can be used to retain filament(s) extending from an implant, as well as to align terminal ends of the implant filament(s) so that the various filaments can be moved and/or trimmed to desired length(s).

The filament management device 1300 of FIG. 14A has a body 1302 that is generally circular in shape and has a top surface 1312 and a bottom surface 1314 (not shown). The device 1300 can also include a slit 1348 extending from a perimeter of the body 1302 to a bore 1350 located at an approximate center of the circular body 1302. Filament, such as the illustrated adjustable limbs 1315a, 1315b, limbs 1316a, 1316b of a leading suture 1316, and limbs 1318a, 1318b of a trailing suture 1318, can be passed through the slit 1348 and disposed in the bore 1350. The filament management device 1300 can then be used to move and/or trim the limbs of the filaments to complementary lengths. Complementary lengths can mean equal lengths, or it can mean desired unequal lengths, depending, at least in part, on the filaments with which the filament management device is being used and the type of procedure in which the filaments are being used. For example, in an instance in which a user desires all of the filaments extending from an implant body to have equal lengths, the filaments can be tensioned and the device 1300 can be slid along a length of the filaments until the device 1300 is proximate to what would become the terminal ends of the filaments at the desired length. The filaments can then be trimmed to the desired length.

In instances in which the device 1300 is used for trimming the lengths of filament, the device 1300 can be disassociated from the filament. Alternatively, the device 1300 can remain associated with the filaments to help manage them, for instance by making it easier to keep track of the various filaments and by preventing them from becoming tangled. In some embodiments, one or more instructional markings can be provided on at least one of the top or bottom surfaces 1312, 1314 to inform a user that filaments associated with an implant can be disposed in the bore 1350. For example, an illustration of the adjustable limbs 1315a, 1315b, the limbs 1316a, 1316b of the leading suture 1316, and the limbs 1318a, 1318b of the trailing suture 1318 can be formed on the top surface 1312.

Filaments can be associated with the filament management device 1300 immediately prior to removing an implant from an implant management device. As a result, filament previously associated with filament retention features of the implant management devices can be held by the filament management device 1300. This can prevent the filament from becoming tangled or damaged as the implant is moved from a location at which the ligament graft was being prepared, for instance a location of the graft preparation device, to a patient's body. The filament management device 1300 can then be disassociated from the filaments immediately prior to the filaments being disposed in the body. Alternatively, the filament management device 1300 can be used for a period of time while the implant is still associated with the implant management device. For example, a user may use the filament management device 1300 to form the complementary limb lengths while the implant is still coupled to or otherwise associated with the implant management device.

The device 1400 illustrated in FIG. 14B provides a different, non-limiting example of an alternative configuration of a filament management device. In one exemplary embodiment, the device 1400 can be used in conjunction with the implant management device 1200.

As shown, the device 1400 has a body 1402 that is generally circular in shape and has a top surface 1412 and a bottom surface 1414 (not shown). The device 1400 can also include a bore 1450 located at an approximate center of the circular body 1402. The bore 1450 can be configured to mate with the bore 1251 of the implant management device 1200 such that the top surface 1412 is approximately parallel to the top surface 1212. While a person having skill in the art will recognize a variety of components that can be used to mate the filament management device 1400 to the implant management device 1200, in one exemplary embodiment a cylindrically-shaped grommet (not illustrated) can be disposed between the two devices 1200, 1400, with respective bores 1251, 1450 of the devices 1200, 1400 receiving opposed bases of the grommet. The bases of the grommet can be open or closed. The resulting configuration can resemble a spool, with the devices 1200, 1400 serving as the ends of the spool and a cylindrical wall extending between the two bases of the grommet serving as the surface around which the excess filament(s) can be disposed.

A second bore 1452 can also be formed through the body 1402, a distance away from the center. A slit 1454 can extend from the perimeter of the circular body 1402 to the second bore 1452, providing an access point to pass filament into the bore 1452. The second bore 1452 can be used to help manage filament by making it easier to keep track of various filaments and by preventing filaments from becoming tangled. For example, terminal ends of filament that has been wrapped around a grommet extending between the implant management device 1200 and the filament management device 1400 can be disposed through the slit 1454 and into the bore 1452. By having the second bore 1452 a distance away from the center, it can be easier to pass filaments into the bore 1452 and remove them from the bore 1452 than when a bore is centrally disposed because the filaments have a shorter distance to travel and thus have a decreased possibility of becoming caught in the slit 1454 as they travel therethrough. Similar to the device 1300, in some embodiments, one or more markings can be made on one or both of the top and bottom surfaces 1412, 1414 to indicate particular purposes of features of the device 1400.

The devices 1300, 1400 can be sized and shaped to be complementary to the sizes and shapes of the implant management device and implant. Any of the materials suitable for forming the implant management devices are also suitable for forming the filament management devices 1300, 1400. A grommet used in conjunction with the device 1400, or other component that serves a similar purpose as a grommet, can be made of any of the materials suitable for forming the implant management devices, including but not limited to a metal or plastic.

Attaching Surgical Implant to Implant Management Device

Figure 15A:
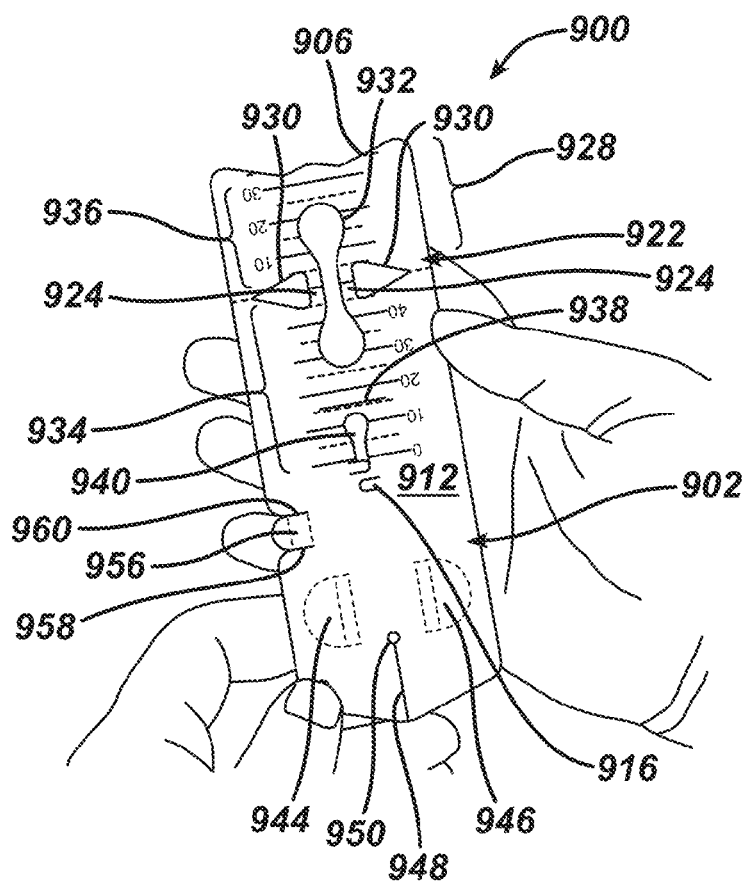
FIGS. 15A-15S are sequential views illustrating one exemplary embodiment of forming the surgical implant management device of FIG. 10A and associating the implant of FIG. 1A therewith.
Figure 15B:
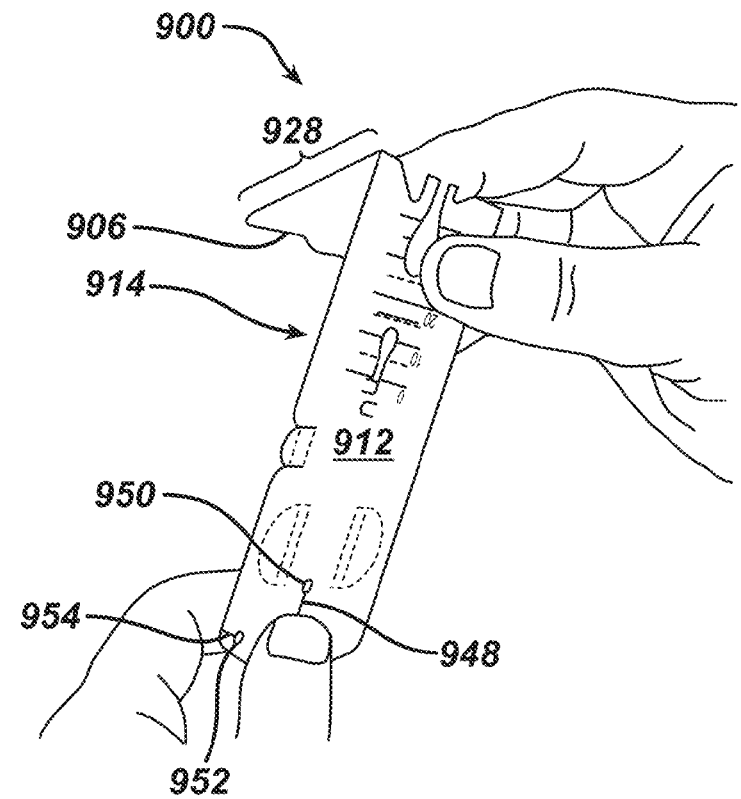
Figure 15C:
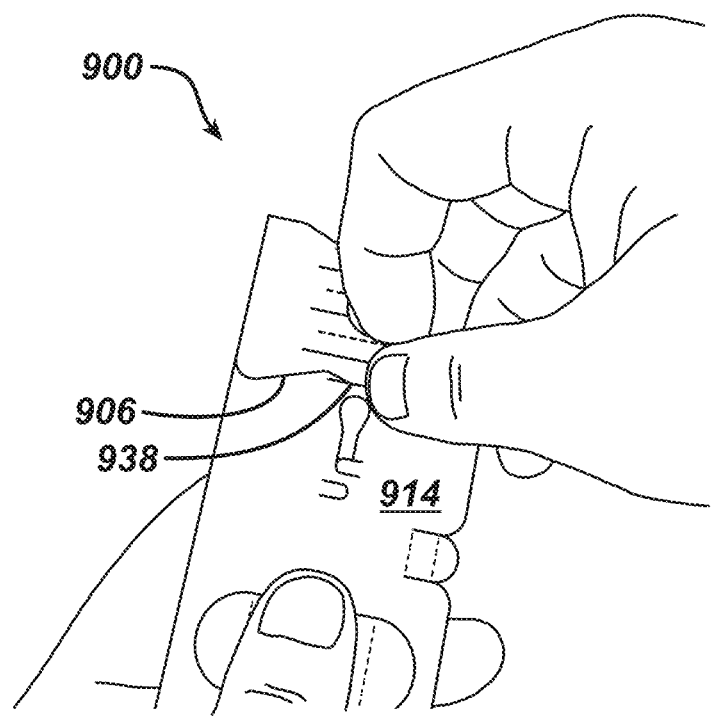
Figure 15D:
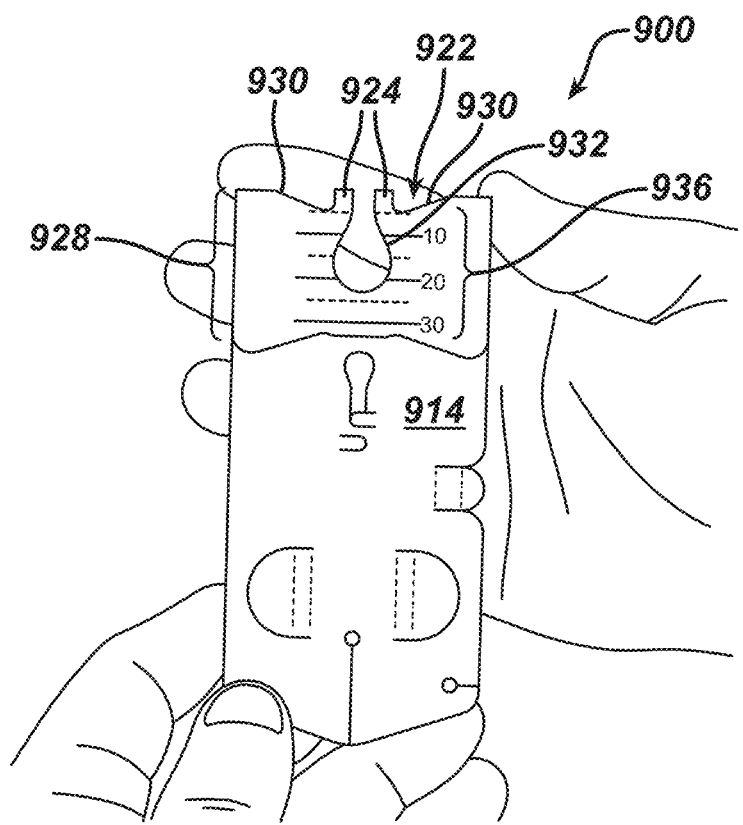
Figure 15E:
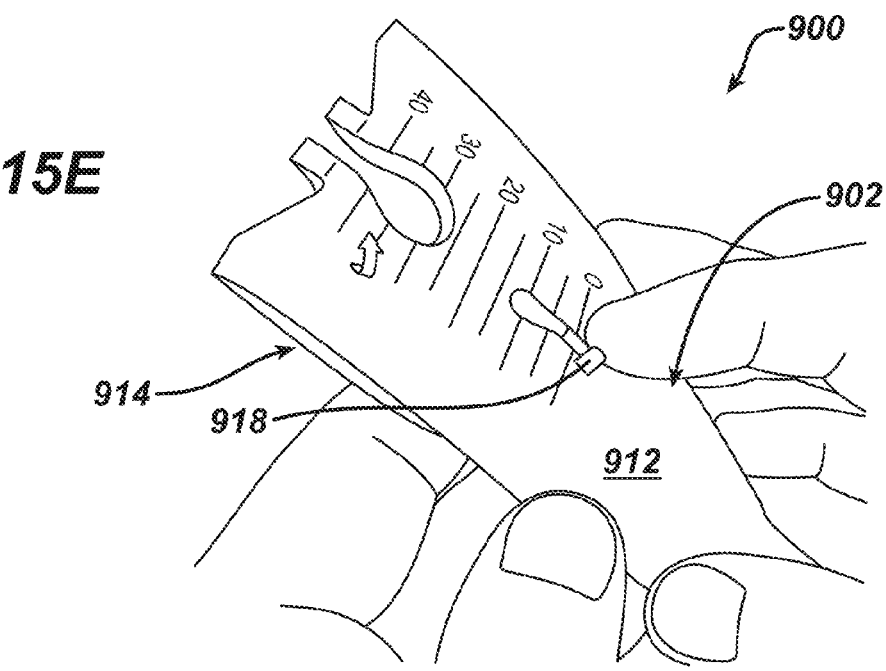
Figure 15F:
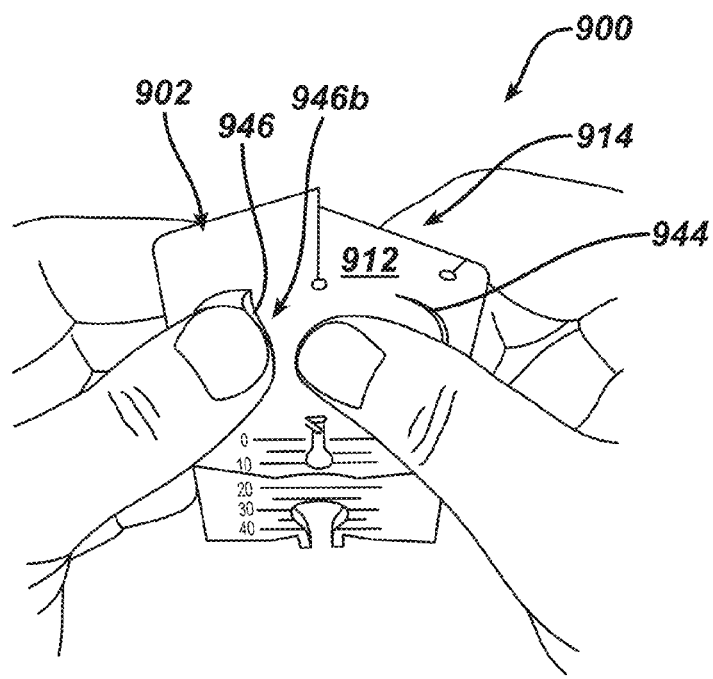
Figure 15G:
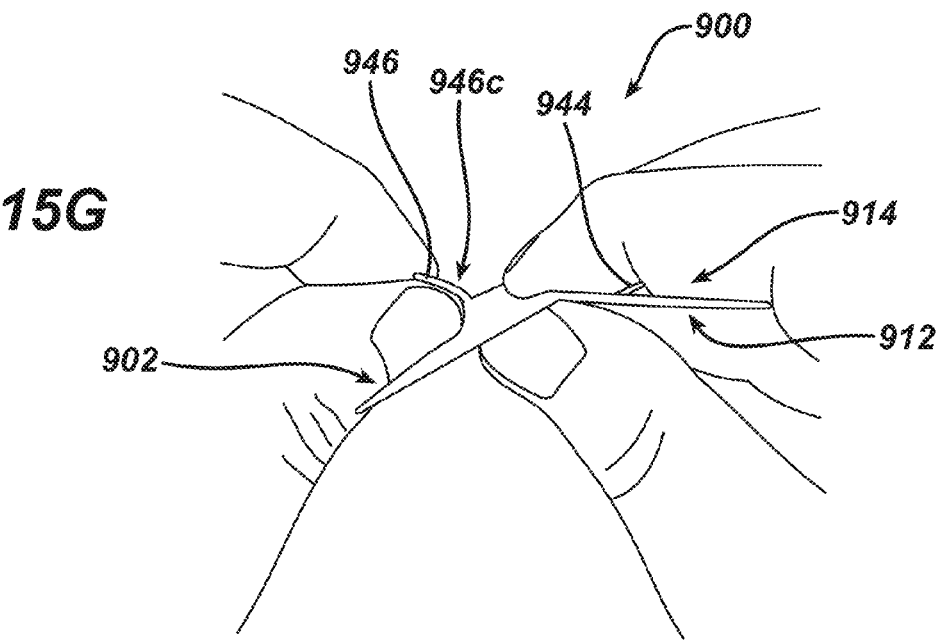
Figure 15H:
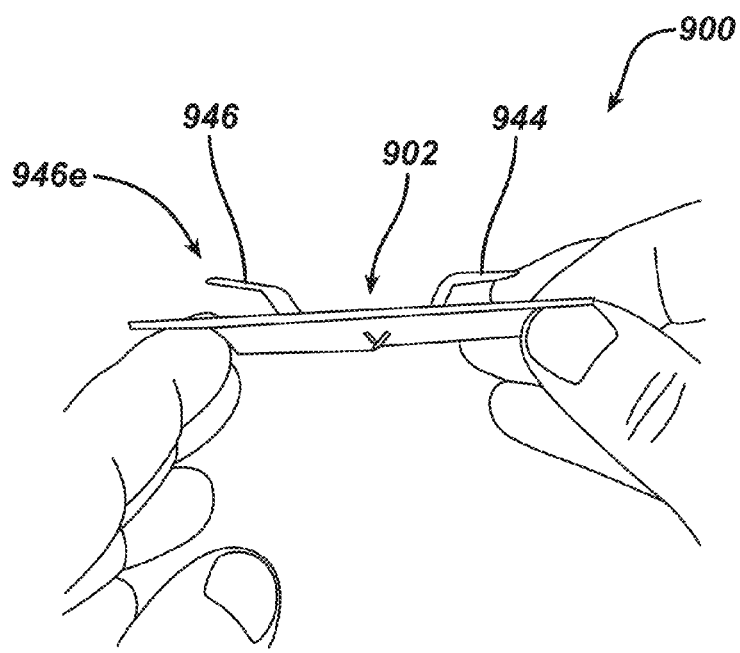
Figure 15I:
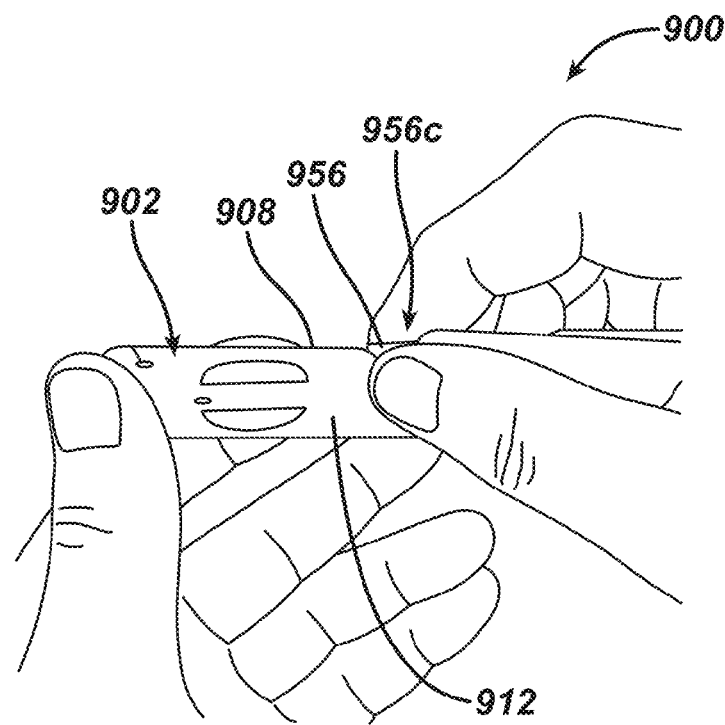
Figure 15J:
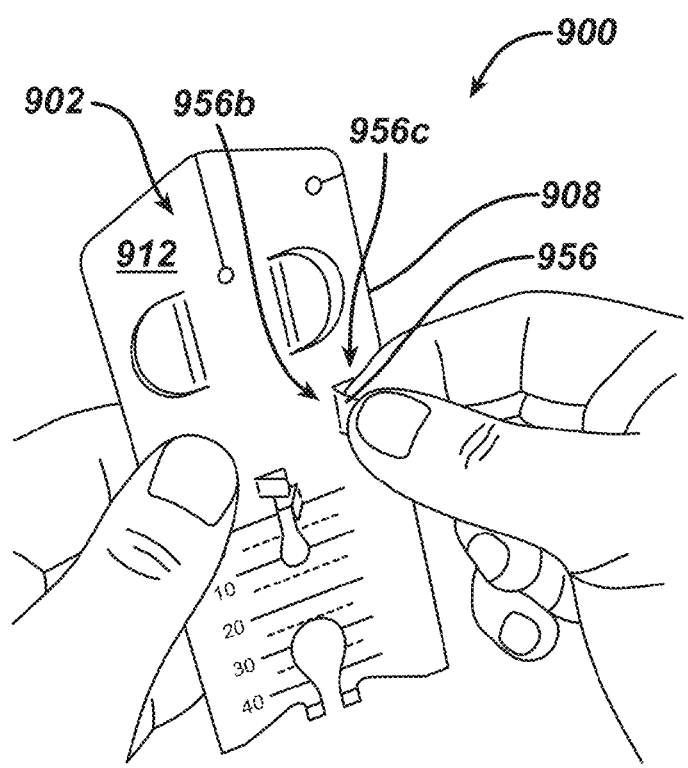
Figure 15K:
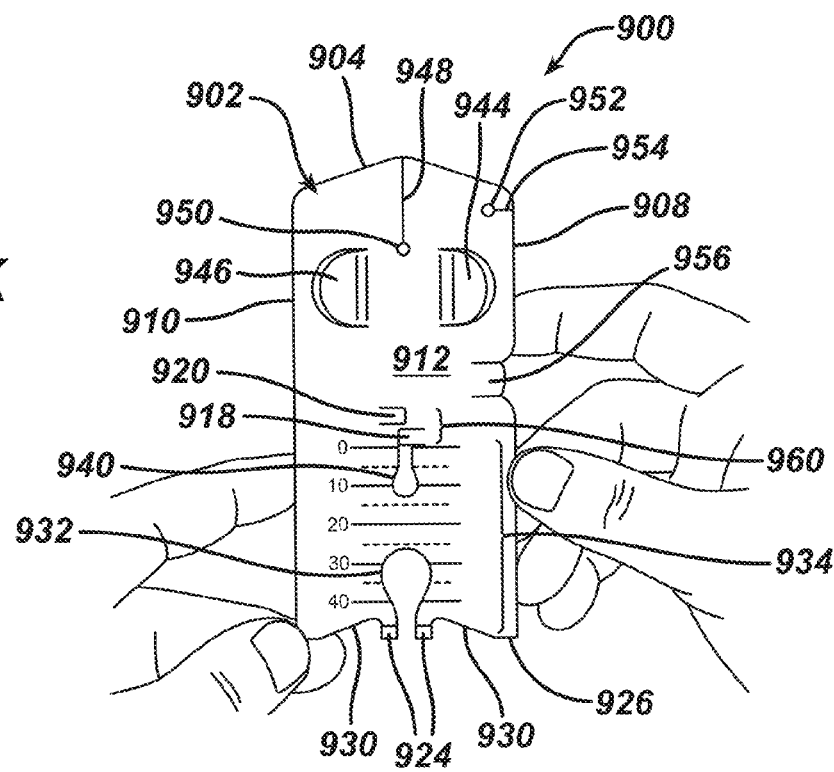
Figure 15L:
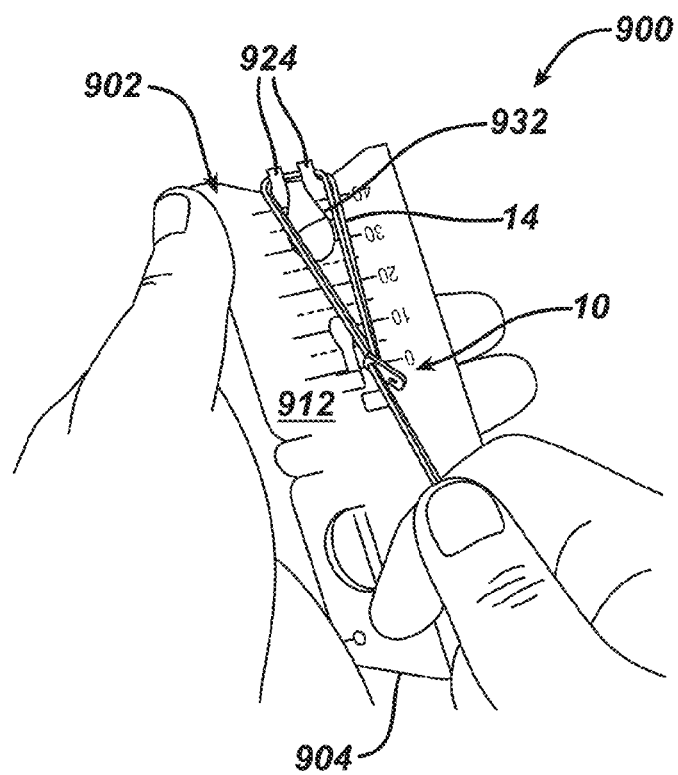
Figure 15M:
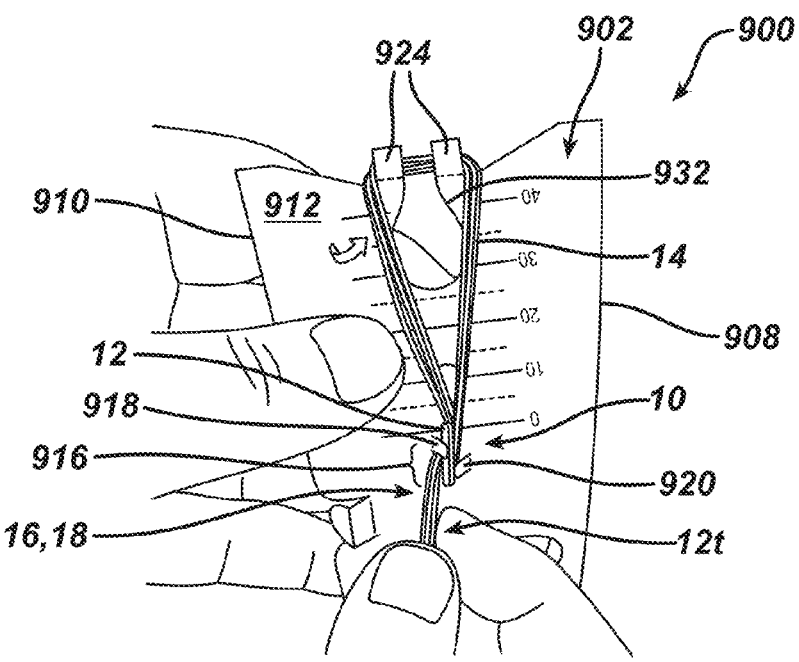
Figure 15N:
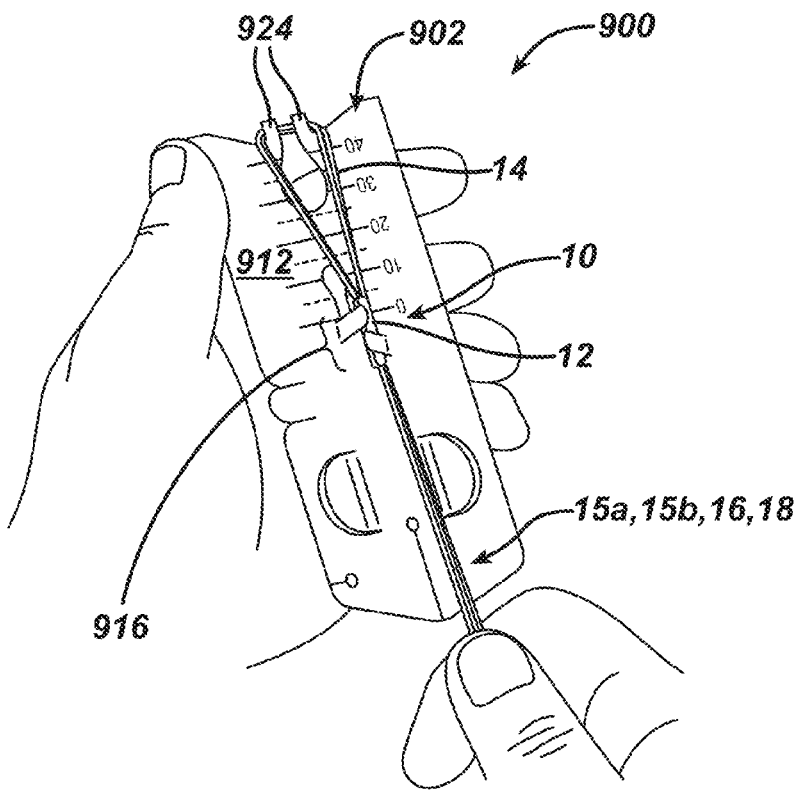
Figure 15O:
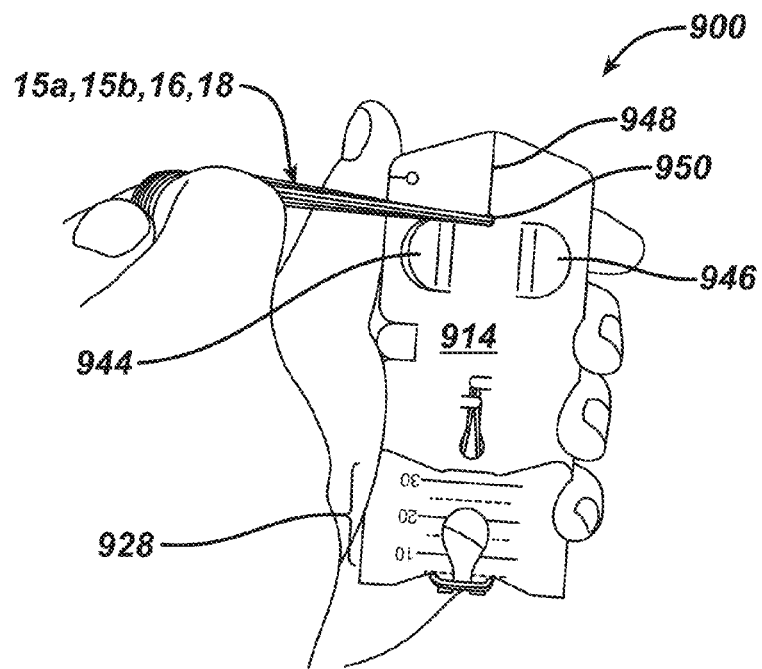
Figure 15P:
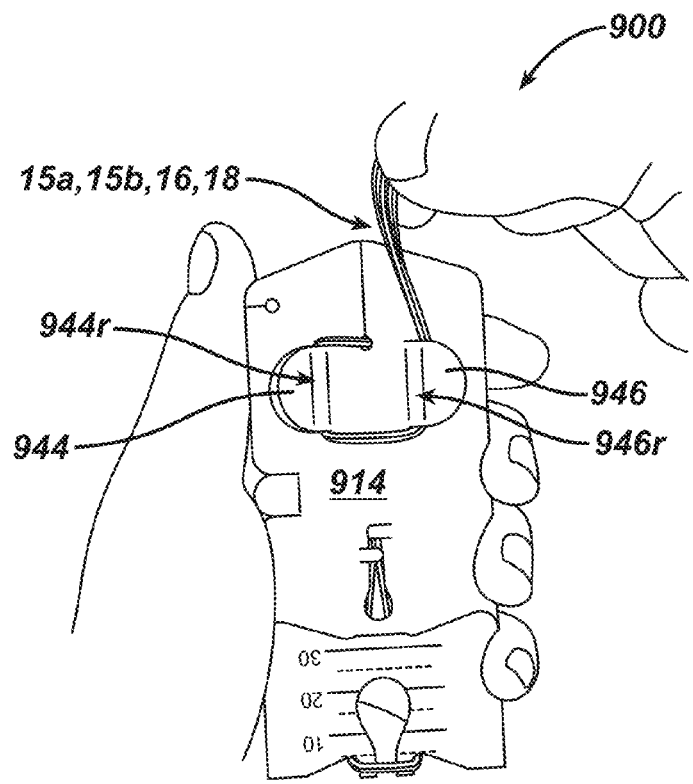
Figure 15Q:
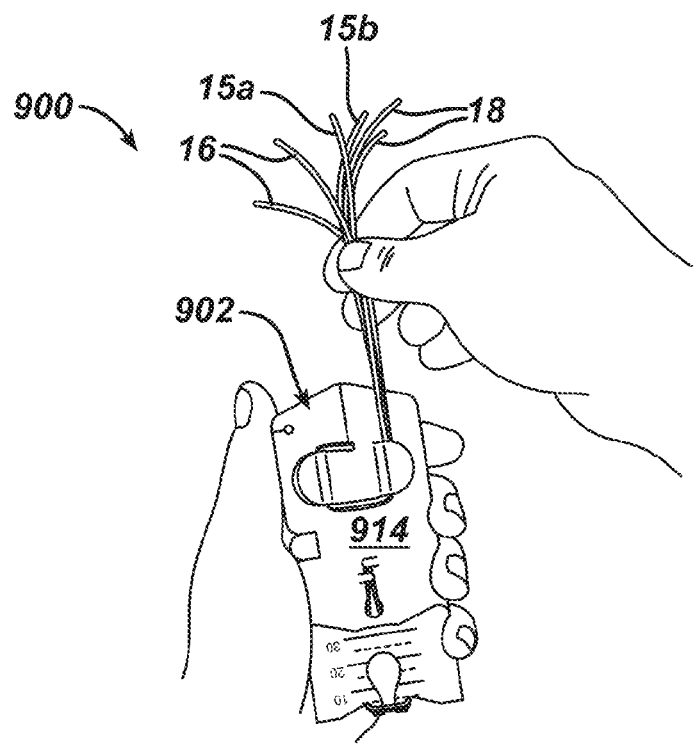
Figure 15R:
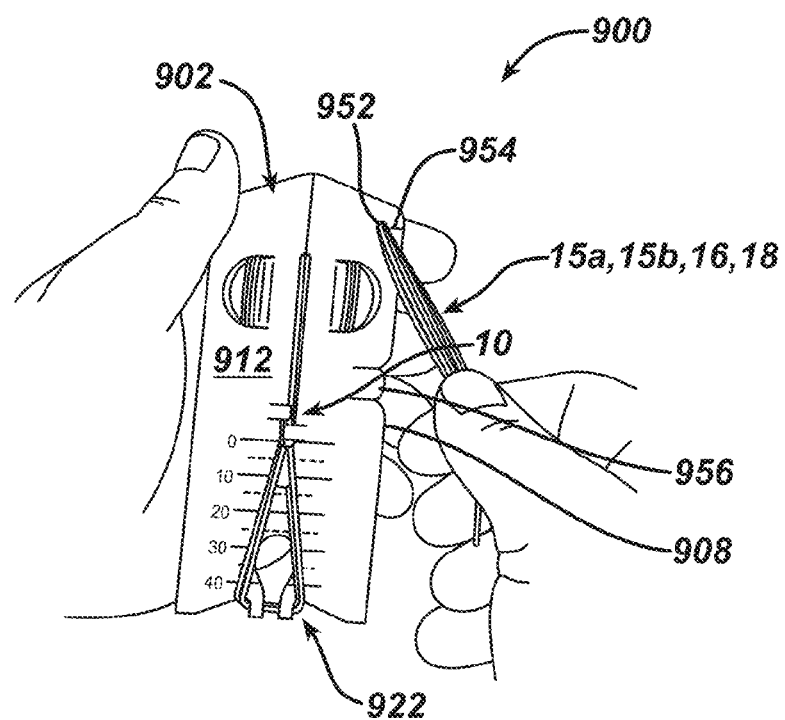
Figure 15S:
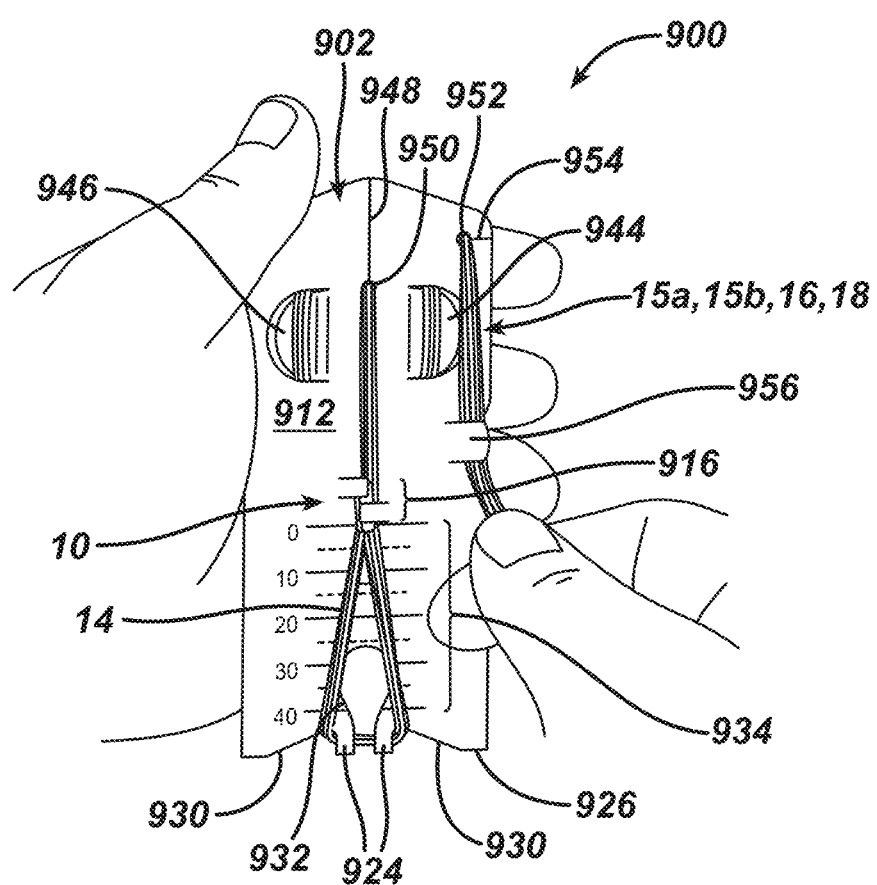

FIGS. 15A-15S illustrate one exemplary embodiment for placing an implant management device, as shown the device 900 of FIG. 10A, in a compact configuration. As shown in FIG. 15A, the device 900 can come in a flat, die cut configuration having the indicia 934, 936 formed on its top surface 912 and the graft-receiving opening 932, opposed openings 930, alignment opening 940, and the plurality of bores 950, 954 (FIG. 15B) and slits 938, 948, 954 (FIG. 15B), 958, 960 that serve as filament retention features already formed therein. The implantable body retainer 916, the fold 926 that is used to form the prongs 924 of the filament loop engaging region 922, the horizontally-disposed filament retention tabs 944, 946, and the retention tab 956 can start in their unformed configurations.

The second portion 928 can be folded toward the bottom surface 914 of the body 902, as shown in FIG. 15B, and the second end 906 can be disposed in the retention slit 938, as shown in FIG. 15C. The resulting configuration is shown in FIG. 15D, in which the second portion 928 is held in place, adjacent to the bottom surface 914, so that the indicia 936 on the second portion 928 are visible when viewing the bottom surface 914. Additionally, the graft-receiving opening 932 and the opposed openings 930 form the prongs 924 of the filament loop engaging region 922. They also form a new terminal end of the body 902 when in the compact configuration.

As shown in FIG. 15E, the opposed tabs 918, 920 (920 is hidden from view in FIG. 15E) that form the implantable body retainer 916 can be flexed or folded so that they are no longer flush with a plane that extends substantially through the top surface 912. FIG. 15E illustrates the tab 918 being flexed away from the body 902, towards the top surface 912 (as opposed to towards the bottom surface 914). The other tab 920 can be flexed in a similar manner, towards the top surface 912.

The horizontally-disposed filament retention tabs 944, 946 can also be flexed or folded so that they are no longer flush with the plane that extends substantially through the top surface 912. As shown in FIG. 15F, the second tab 946 can be folded at a first fold 946b, towards the top surface 912 (as opposed to towards the bottom surface 914), so it is out of the aforementioned plane. The tab 946 can then be flexed back down toward the bottom surface 914 along the fold 946b so that the tab 946 ends up being disposed below the bottom surface 914. In alternative embodiments, the tab 946 can just be flexed down towards the bottom surface 914. The second tab 946 can also be folded at a second fold 946c, back towards the body 902, as shown in FIG. 15G. As a result, an end portion 946e of the tab 946 can be substantially parallel to the aforementioned plane, as shown in FIG. 15H. FIGS. 15F-15H also illustrate that these same flexing or folding maneuvers were applied to the first tab 944.

The retention tab 956 disposed in the first wall 908 can also be flexed or folded so it is configured to be at least partially disposed around filament. FIG. 15I illustrates that the tab 956 can be folded along a more centrally disposed fold 956c, towards the top surface 912. Then the tab 956 can be folded along a second fold 956b, back towards the body 902, as shown in FIG. 15J. This results in the formation of a sleeve in which filament can be disposed, as described in greater detail herein.

After all of the folding and flexing is completed, the implant management device 900 can look like the device as illustrated in FIG. 15K. A person skilled in the art will recognize that the various steps leading up to this configuration can generally be performed in any order without departing from the spirit of the present disclosure. Accordingly, by way of non-limiting example, the horizontally-disposed retention tabs 944, 946 can be formed after the retention tab 956, or alternatively, before the second portion 928 is folded towards the bottom surface 914.

FIG. 15L illustrates one option for a beginning step to associate the implant 10 of FIG. 1A with the implant management device 900. As shown, the loops 14 are disposed around the prongs 924 and the remaining portion of the implant 10 is moved toward the first end 904. It can be helpful to keep all of the loops 14 aligned so that they are not twisted or crossed, and so that each frames the graft-receiving opening 932, as more clearly illustrated in FIG. 15M.

FIG. 15M also illustrates the implant body 12 being associated with the tabs 918, 920 of the implantable body retainer 916. The tab 916 that is more proximate to the 0 millimeter indicia line can be flexed towards the second wall 910 to allow the body 12 to pass under it, and then it can be flexed back towards the body 902 to help secure one end of the body 12 to the device 900. The other tab 920 can then be flexed towards the first wall 908, and subsequently back towards the body 902 after the body 12 is disposed thereunder, to help secure the other end of the body 12 to the device 900. The terminal end of the body 12 associated with the more proximate tab 918 can typically be located approximately at the 0 millimeter indicia line to help insure accurate usage, such as when a user is making markings on the top surface 912 or the loops 14. As shown in FIG. 15N, the filaments extending from the top side 12t of the body 12, i.e., the adjustable limbs 15a, 15b, the leading suture 16, and the trailing suture 18, can be pulled tight to confirm secure placement of the implant body 12 with respect to the device 900.

After the body 12 is secured by the implantable body retainer 916, the adjustable limbs 15a, 15b, leading suture 16, and trailing suture 18 can be inserted through the central slit 948 and disposed in the bore 950 at which the slit 948 terminates, as shown in FIG. 15O. A tension can be applied to each of the limbs 15a, 15b and sutures 16, 18 to insure that loose filament does not interfere with viewing the top surface 912 and implant 10. While maintaining the tension, as shown in FIG. 15P, the limbs 15a, 15b and sutures 16, 18 can be wrapped around the horizontally-disposed filament retention tabs 944, 946. More particularly, the limbs 15a, 15b and sutures 16, 18 can be wrapped around receiving regions 944r, 946r of the tabs 944, 946 until the remaining portions of limbs 15a, 15b and sutures 16, 18 are at desired lengths. FIG. 15Q illustrates one example of limbs 15a, 15b and sutures 16, 18 at desired lengths, in which the remaining portions of the filaments 15a, 15b, 16, 18 can be retained by the other filament retention features, but is not so much that excess filament will get in the way of the user. In one exemplary embodiment, the filaments 15a, 15b, 16, 18 are wrapped around the tabs 944, 946 for approximately three full rotations before the remaining portions are directed to additional filament retention features.

As shown in FIG. 15R, the limbs 15a, 15b and sutures 16, 18 can be moved towards the slit 954 formed in the first wall 908. The limbs 15a, 15b and sutures 16, 18 can be passed through the slit 954 and enter the bore 952 to be retained therein. The excess portions of the limbs 15a, 15b and sutures 16, 18 can then be advanced towards the retention tab 956. As shown in FIG. 15S, the retention tab 956 can engage the limbs 15a, 15b and sutures 16, 18 to secure their location along the edge of the body 902. Excess portions of the limbs 15a, 15b and sutures 16, 18 can extend from the retention tab 956, towards the filament loop engaging region 922, although it can be preferable that this amount not be enough so as to interfere with the user's vision of the top surface 912 or with preparation steps performed leading up to a surgical procedure.

The method described with respect to FIGS. 15A-15S can be performed by a user on location, e.g., a surgery room, or alternatively, the implant 10 can be associated with the implant management device 900 at a manufacturing facility prior to shipping and packaging the combination of the device 900 and implant 10. Further, a person having skill in the art will recognize a variety of other ways by which an implant can be associated with an implant management device in view of the disclosures provided for herein, depending, at least in part, on the configurations of the implant management device and the implant, and the type of procedure with which the device and implant are being used.

Graft Preparation Device

Figure 16:
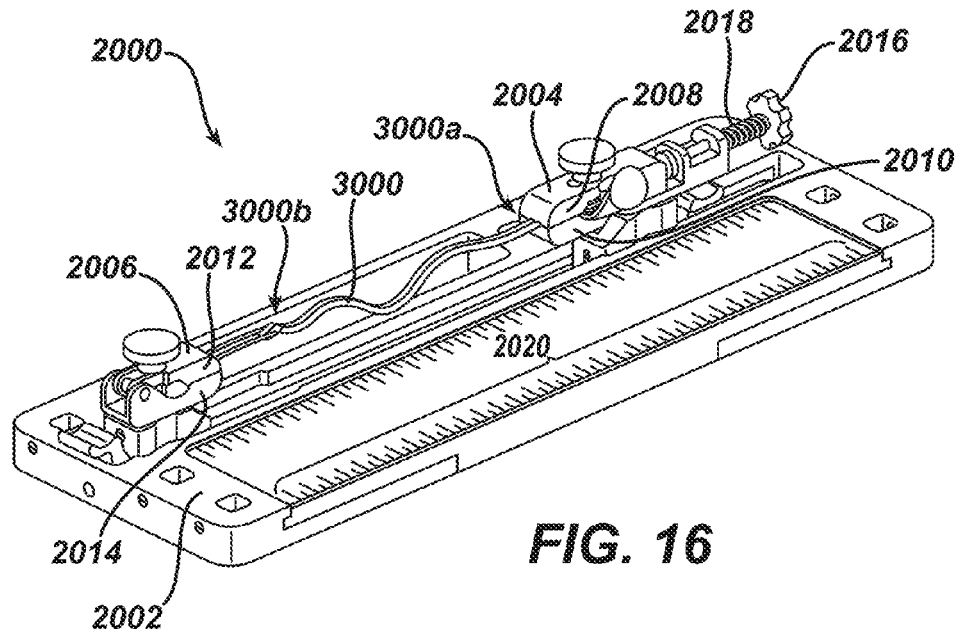
FIG. 16 is a perspective view of one exemplary embodiment of a graft preparation device.

Once an implant is coupled to the implant management device, the device can be used in conjunction with a graft preparation device or board to assist in making measurements. Graft preparation devices are generally known to those skilled in the art, and thus only a general description of such a device is provided for herein. As illustrated in FIG. 16, a graft preparation device 2000 can include a platform 2002 having a first retention element 2004 and an opposed second retention element 2006 extending from the platform 2002. The retention elements 2004, 2006 can generally be configured to grasp opposed terminal ends 3000a, 300b of a ligament graft 3000. In the illustrated embodiment, the retention elements 2004, 2006 include jaws 2008, 2010 and 2012, 2014, respectively, for grasping the terminal ends 3000a, 3000b of the ligament graft 3000, although a variety of other techniques can be used to secure a location of the ligament graft 3000 with respect to the preparation device 2000. A tensioning element 2016 can be in mechanical cooperation with the first retention element 2004 and it can be operable to supply tension to the ligament graft by linearly displacing the first grasping element 2004 along a length of the platform 2002. As shown, a sliding threaded shaft 2018 can extend between the tensioning element 2016 and the first retention element 2004 to assist in the linear displacement. Indicia 2020 can be provided on the platform 2002 to help read the length of the ligament graft, or to make markings or indicators on the ligament graft. Further details about graft preparation devices are provided in U.S. Pat. No. 6,796,977 of Yap et al., the content of which is incorporated by reference herein in its entirety.

Figure 17A:
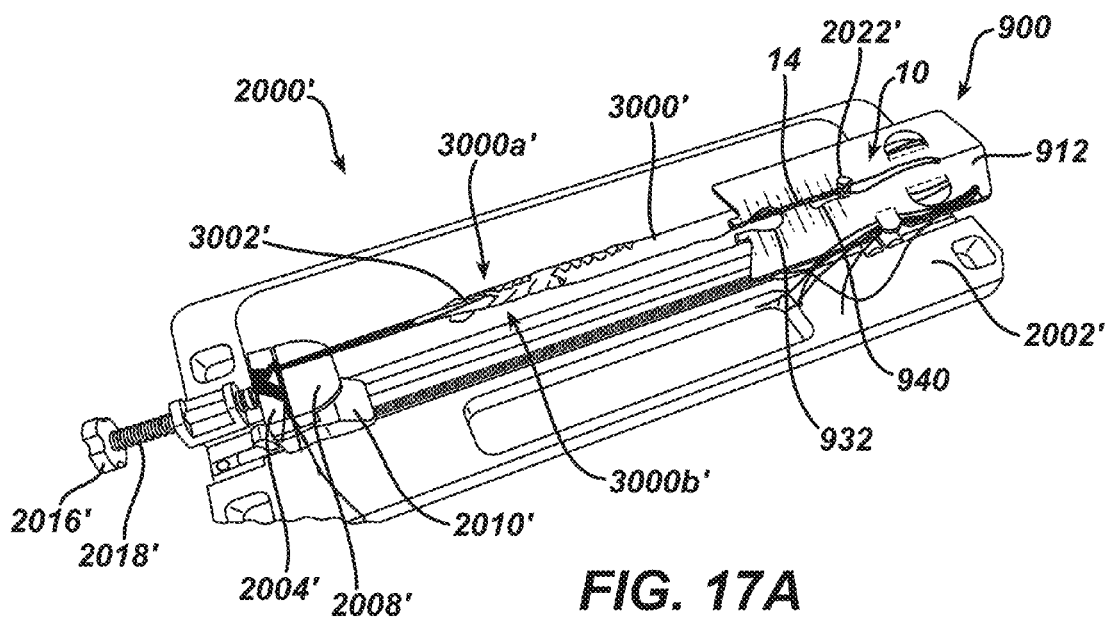
FIG. 17A is a perspective view of the surgical implant management device and implant of FIG. 15S coupled to a graft preparation device, the implant and draft preparation device having a ligament graft associated therewith.
Figure 17B:
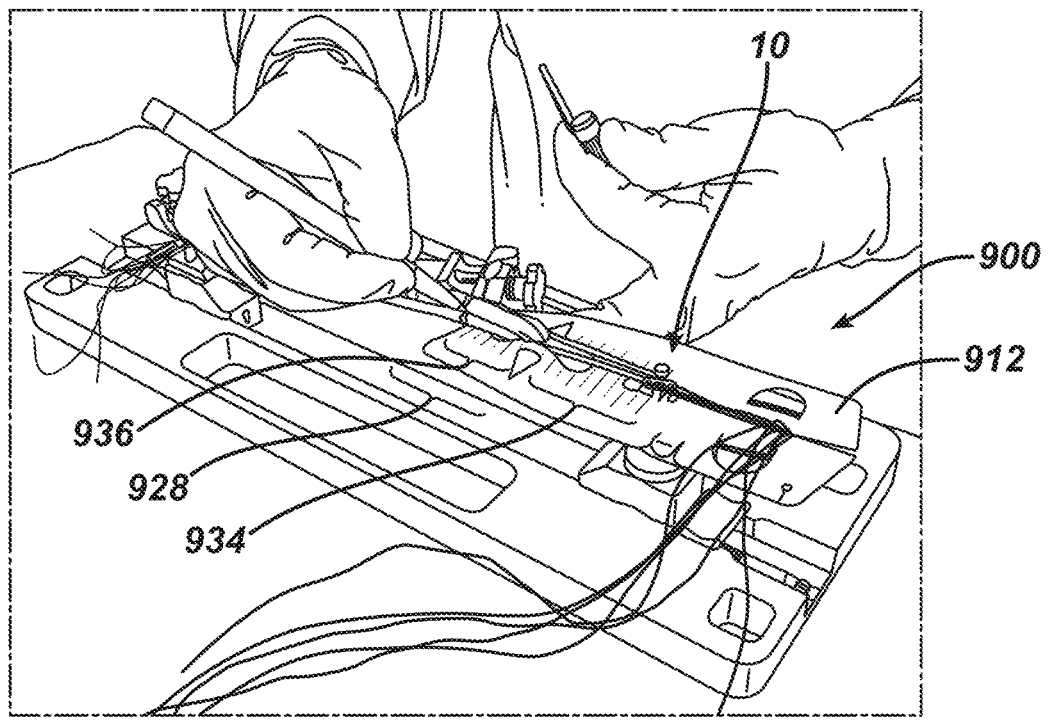
FIG. 17B is a perspective view of the surgical implant management device, implant, graft preparation device, and ligament graft of FIG. 17A, illustrating a user marking the ligament graft.

FIGS. 17A and 17B illustrate an alternative embodiment of a graft preparation device or board 2000' being used in conjunction with the implant management device 900 and implant 10 of FIG. 15S. The graft preparation device 2000' can include a platform 2002' and first and second retention elements 2004', 2006' extending therefrom. As shown, the first retention element 2004' includes jaws 2008', 2010' for grasping a ligament graft 3000', and the second retention element 2006' includes a post 2022' configured to receive the alignment opening 940 of the implant management device 900. The ligament graft 3000', which as shown is disposed through the graft-receiving opening 932 and is thus coupled to the loops 14, can extend from the implant management device 900 and towards the first retention element 2004'. In the illustrated embodiment, the ligament graft 3000' is not long enough to reach first retention element 2004', and thus one or more free limbs of suture 3002' can be whip-stitched onto both terminal ends 3000a', 3000b' of the ligament graft 3000'. The suture 3002' can then be wrapped around the first retention element 2004' to secure the suture 3002' with respect to the first retention element 2004' and apply tension to the ligament graft 3000'. As tension is supplied by a tensioning element 2016' to the first retention element 2004', via a sliding thread shaft 2018', the tension translates through the suture 3002' and to the ligament graft 3000'. As the ligament graft 3000' is moved away from the post 2022', tension in the ligament graft 3000' increases. A person skilled in the art will recognize a variety of other ways by which the implant device 900, and the ligament graft 3000', can be associated with graft preparation devices to supply the desired tension.

As shown in FIG. 17B, because of the configuration of the implant management device 900, and in particular the indicia 934, 936 provided for on the top surface 912, when the desired tension is supplied to the ligament graft 3000', markings or indicators can be made on the device 900, the implant 10, e.g., the loops 14, and/or the ligament graft 3000' without relying on a separate measurement instrument, such as a ruler or indicia formed on a graft preparation device. The indicators can then be used by a surgeon during a surgical procedure to provide valuable feedback about the location of the implant 10, and graft 3000'. The second portion 928 of the device 900 can actually be returned to the unfolded configuration so that measurements related to the ligament graft 3000' can be made, as shown.

A person skilled in the art will recognize that a variety of measurements and related indicators can be made using this set-up, depending, at least in part, on the devices being used and the type of procedure being performed. By way of non-limiting example, in some surgical procedures, such as an ACL repair, a tunnel can be formed having two different diameters. The implant 10 can be configured to have a final implant location in the tunnel with the smaller diameter while the ligament graft 3000' can have a final implant location in the tunnel having a larger diameter. The user can measure the depths of the tunnel and use the indicia 934, 936 to mark the loops 14 and ligament graft 3000' so that the user knows when the implant 10 and the ligament graft 3000' are at desired locations. A working example of the types of measurements that can be made during an ACL repair are provided below with respect to FIGS. 18A-18F.

ACL Repair Using Indicators Made on Implant and Ligament Graft

Figure 18A:
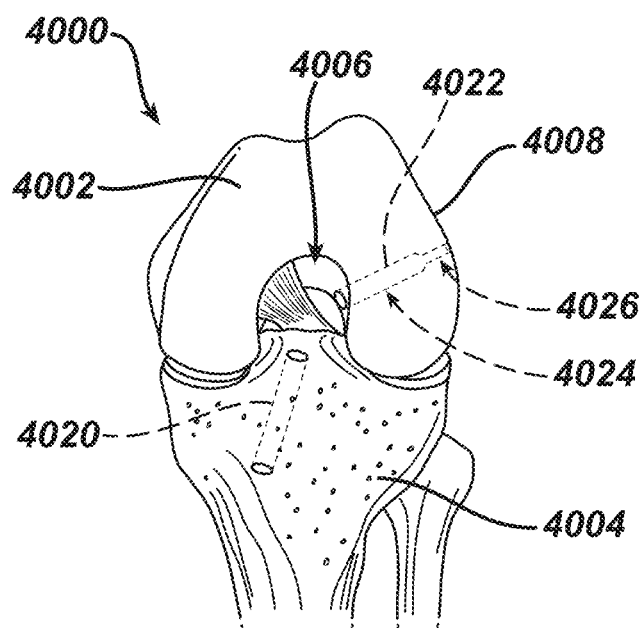
FIGS. 18A-18F are schematic, sequential views of one exemplary embodiment for implanting the ligament graft of FIG. 17B in a bone tunnel using the implant of FIG. 15S that was previously associated with the graft preparation device of FIG. 17B.

As illustrated in FIG. 18A, a knee 4000 can be prepared for an ACL repair procedure by forming the necessary tunnels 4020, 4022 in the femur 4002 and tibia 4004. Techniques known to those skilled in the art can be used to form these tunnels. The femoral tunnel 4022 can include both a main channel 4024 and a passing channel 4026, with the passing channel 4026 having a smaller diameter than the main channel 4024. The tibial tunnel 4020 can be situated such that components passed from the tibial tunnel 4020 can easily pass through joint space 4006 between the tibia 4004 and femur 4002 and into the main channel 4024 of the femoral tunnel 4022.

The depths of the various tunnels can be measured and those measurements can be indicated by making markings or indicators on any of the implant management device, implant 10, and ligament graft 3000'. In some embodiments, marking the indicators on the device, implant, and ligament graft can occur in conjunction with, i.e., simultaneously with, the tunnel formation in the bone. This can eliminate separate bone tunnel measuring. Further, if a first person forms the bone tunnel while a second person makes the markings or indicators indicative of the bone tunnel depths at the same time, it can make for a more accurate and efficient process than previous surgical procedures.

The implant 10, device 900, and ligament graft 3000' can be prepared in advance of marking indicators on at least one of these components. While some of the specifics of the preparation steps are discussed above with respect to FIGS. 15A-15S and FIGS. 17A-17B, generally the implant can be coupled to the device 900 if it did not already come pre-packaged as such and the ligament graft 3000' can be prepared for coupling to loops 14 of the implant. The ligament graft 3000' can be cleaned by removing any excess tissue, and then the free limbs of suture 3002' can be whip-stitched on both terminal ends 3000a', 3000b' of the ligament graft 3000'. The ligament graft 3000' can be passed through the graft-receiving opening such that an approximate center portion of the ligament graft 3000' engages the implant filament loops 14 and the terminal ends 3000a', 3000b' are on opposite sides of the loops 14, approximately adjacent to each other. The free limbs of suture 3002' can then be coupled to the first retention element 2004', and the post 2022' can engage the alignment opening 940 of the device 900. Tension can be applied to the free limbs of suture 3002' to position the device 900, implant 10, and ligament graft 3000' in a suitable position for marking.

Figure 18B:
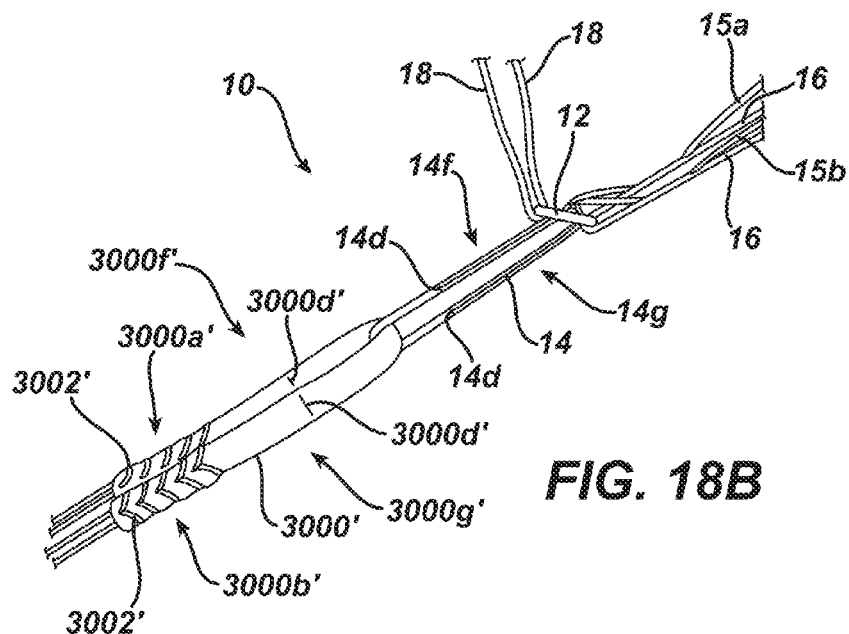

In one exemplary embodiment, a full depth of the femoral tunnel 4022 can be marked on the loops 14 of the implant 10. This measurement can sometimes be referred to as a total bone stock depth. In such an embodiment, if the depth of the femoral tunnel 4022 is 40 millimeters, then a user can place one or more indicators 14d on the loops 14, for instance on both a first side 14f and a second side 14g of the loops 14 as shown in FIG. 18B, 40 millimeters away from the implant body 12. By keeping the implant 10 on the device 900, a user can rely on the indicia 934 disposed between the implantable body retainer 916 and the prongs 924 to mark the indicators 14d on the loops 14. The surgeon can then rely on the indicators 14d during the procedure, as discussed in greater detail below.

Further, a depth of just the main channel 4022 can be marked on the ligament graft 3000'. This measurement can sometimes be referred to as a graft-in-tunnel depth. In such an embodiment, if the depth of the main channel 4022 is 25 millimeters, then a user can place one or more markings or indicators 3000d' on the ligament graft 3000', for instance on both a first side 3000f' and a second side 3000g' of the ligament graft 3000' as shown in FIG. 18B, 25 millimeters away from the location at which the ligament graft 3000' is in contact with loops 14 of the implant 10. By keeping the implant 10 on the device 900, a user can rely on the indicia 936 disposed on the second portion 928 to mark indicators 3000d' on the graft 3000'. The surgeon can then rely on the indicators 3000d' during the procedure, as discussed in greater detail below.

After the indicators 14d, 3000d' have been made on the implant 14 and the ligament graft 3000', the implant 10 can be decoupled or otherwise disassociated from the implant management device 900. In some procedures, the implant 10 can be removed from the device 900 in the opposite order by which the implant 10 was originally associated with the device 900. Thus, the adjustable limbs 15a, 15b, leading suture 16, and trailing suture 18 can be pulled out of the retention tab 956 and bore 952 and slit 954, and then unwound from the horizontally-disposed filament retention tabs 944, 946. The limbs 15a, 15b and sutures 16, 18 can then be pulled out of the bore 950 and slit 948, the implant body 12 can be removed from the implantable body retainer 916, and the loops 14 can be pulled away from the prongs 924. The resulting configuration of the implant 10 disassociated from the device 900 is illustrated in FIG. 18B. As shown, the ligament graft 3000' is disposed within the loops 14, and the ligament graft indicators 3000d' are formed on the first and second sides 3000f', 3000g' of the ligament graft 3000' and the loop indicators 14d are formed on the first and second sides 14f, 14g of the loop 14. The implant 10 further includes limbs 16a, 16b of the leading suture 16, limbs 18a, 18b of the trailing suture 18, and the adjustable limbs 15a, 15b that can collapse the loop 14, which as shown can extend into the receiving portions 17a, 17b of the leading suture limbs 16a, 16b. Further, the free limbs of suture 3002' are associated with the terminal ends 3002a', 3002b' of the ligament graft 3000' to help apply tension to, and otherwise control, the ligament graft 3000' when using the graft preparation device and during the surgical procedure.

Figure 18C:
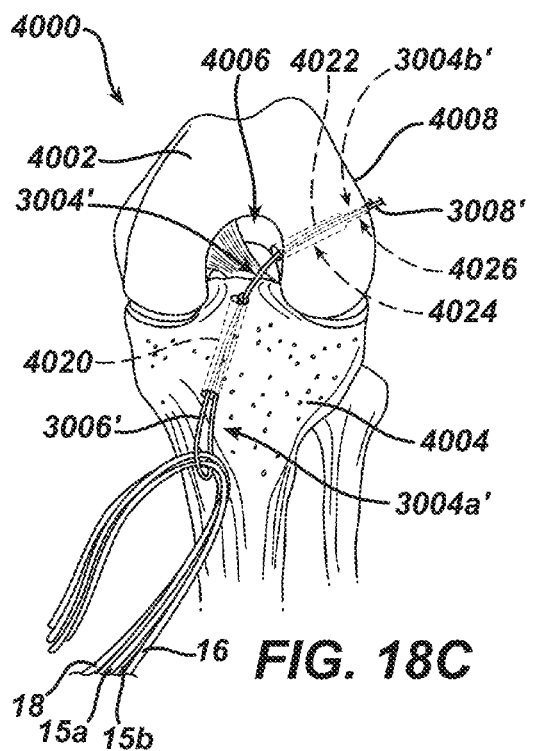

As shown in FIG. 18C, a passing loop suture or shuttle suture 3004' can be used to help initially pull the implant 10 through the tibial and femoral tunnels 4020, 4022. Passing loop sutures or shuttle sutures are known to those skilled in the art, but in the illustrated embodiment, it includes a first end 3004a' having a loop 3006' formed therein for receiving filaments and a second end 3004b' that is a limb 3008' that can be grasped by a surgeon to move the loop 3006'. A portion of each of the leading suture 16, the trailing suture 18, and the adjustable limbs 15a, 15b can be inserted through the loop 3006, and then travel with the passing loop suture 3004' as it passes from the tibial tunnel 4020, through the joint space 4006, and into and through the femoral tunnel 4022. In some embodiments, approximately no more than about 7 centimeters to about 10 centimeters of each of the leading suture 16, trailing suture 18, and adjustable limbs 15a, 15b should be passed through the tunnels 4020, 4022 with the passing loop suture 3004' so that the filaments 15a, 15b, 16, 18 do not get caught in the tunnels 4020, 4022.

Figure 18D:
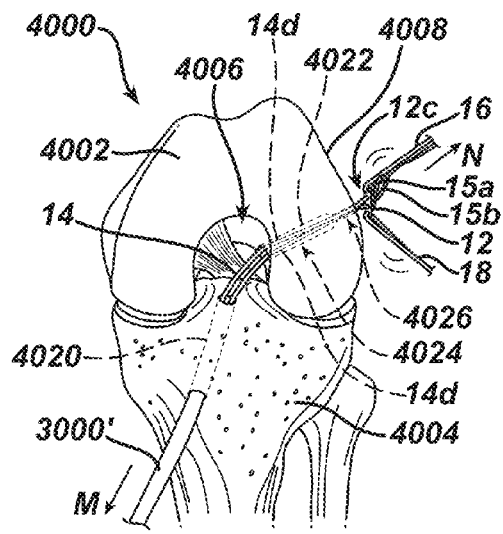

Once the implant body 12 is in the joint space 4006, a portion of each of the leading suture 16, the trailing suture 18, and the adjustable limbs 15a, 15b can be disposed through the femoral tunnel 4022 so that they can be grasped by a surgeon outside of the tunnel 4022. The implant body 12 can be viewed in the joint space 4006 using a number of techniques known to those skilled in the art, but in some embodiments a surgeon can insert an endoscope or other viewing device into the joint space 4006. The implant body 12 can then be pulled into the femoral tunnel 4022 by applying a majority of the tension to the leading suture 16. At the same time, it can be helpful to maintain adequate tension on the trailing suture 18, as well as the adjustable limbs 15a, 15b to the extent they are not being tensioned by the tension applied to the leading suture 16, such that the trailing suture 18 and adjustable limbs 15a, 15b are at least taut. Further, tension can also be applied to the ligament graft 3000' that extends through the tibial tunnel 4020, or to the free limbs of suture 3002' associated therewith, the tension being applied in a direction M, moving away from the femoral tunnel 4022 and toward the tibial tunnel 4020. The direction M is illustrated in FIG. 18D, which is described in further detail below.

As the implant body 12 is pulled through the femoral tunnel 4022, it can be helpful to know once the implant body 12 has passed through the entirety of the tunnel, including through the passing channel 4026, so the surgeon can know that the body 12 is in a position to be flipped or otherwise situated against the femoral cortex 4008 to set the implanted location of the body 12. It may not be easy for a surgeon to know that the implant body 12 has exited the passing channel because resistance provided by tissue and other body parts surrounding the femoral cortex 4008 can be similar to the resistance that existed when the implant was disposed in the femoral tunnel 4022. Further, it can be more difficult to dispose a viewing device such as an endoscope near the femoral cortex 4008, as opposed to the joint space 4006, because of the tissue and other components proximate to the femoral cortex 4008. Thus, without knowing if the implant has exited the femoral tunnel 4022, a surgeon may continue to try and pull the implant body 12 through the femoral tunnel 4022, only to discover that he or she is actually pulling the implant body 12 through tissue or other portions of the body, and in turn damaging the implant, the graft, and/or the tissue or other portions of the body.

The indicators 14d on the loops 14, however, can remedy the problem of not knowing when the implant has excited the femoral tunnel 4022. Using the endoscope or other viewing device disposed in the joint space 4006, the surgeon can view the entrance to the main channel 4024 to observe a location of the indicators 14d with respect to the main channel 4024. When the indicators 14d are no longer visible in the joint space 4006 because they are disposed in the main channel 4024, the surgeon knows that the implant body 10 has exited the passing channel 4026 because the location of the indicators 14d is representative of the length of the femoral tunnel 4022. The surgeon then knows that he or she can flip or otherwise situate the implant body 12 against the femoral cortex 4008. While a variety of techniques known to those skilled in the art can be used to flip or reorient the body 12 against the femoral cortex 4008, in the illustrated embodiment of FIG. 18D, the leading and trailing sutures 16, 18 are manipulated such that a bottom surface 12c of the implant body 12 rests against the cortex 4008. Alternatively, or additionally, a force can be selectively applied to the ligament graft 3000' in an approximate direction M to tension the ligament graft 3000' and help manipulate the body 12 into the desired position by "flipping" it. Once the surgeon has oriented the implant body 12 as desired, the surgeon can confirm its location as lying flat on the femoral cortex 4008, directly adjacent to the femoral tunnel 4022, using a variety of techniques, including by using tactile feedback received from pulling the leading and trailing sutures 16, 18 and the ligament graft 3000', and/or using visual aids.

Figure 18E:
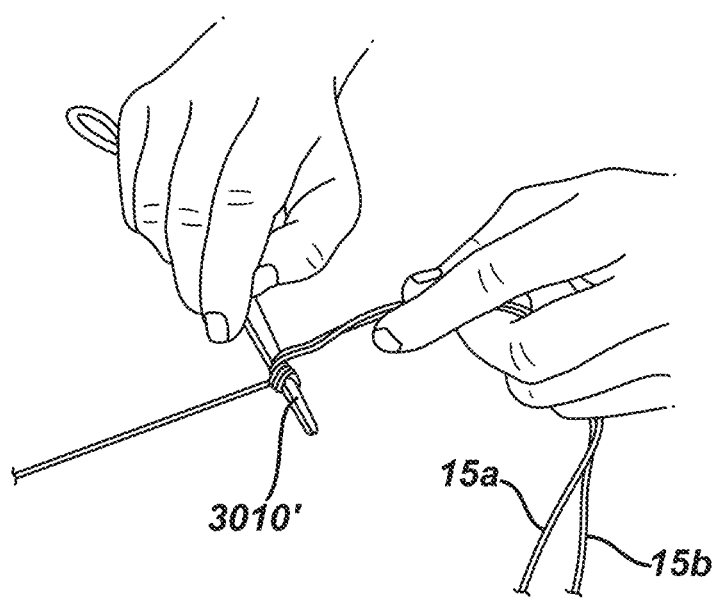

Once the body 12 is disposed at its desired location, tension can be applied in a direction N to the adjustable limbs 15a, 15b to decrease the circumference of the loops 14, thereby drawing the ligament graft 3000' associated therewith further into the main channel 4024. The tension can be applied in a variety of manners, including simply by pulling in the direction N. In some embodiments, as shown in FIG. 18E, the adjustable limbs 15a, 15b can be wrapped around an object, as shown a tool 3010', to assist with achieving the desired tension. Downward tension in the direction M on the ligament graft 3000' can also be applied while applying tension to the adjustable limbs 15a, 15b so that the ligament graft 3000' and free limbs of suture 3002' associated therewith are not jerked too quickly in the direction N.

As the ligament graft 3000' is advanced through the main channel 4024 and toward the passing channel 426, it can be helpful to know once the ligament graft 3000' is disposed directly adjacent to the passing channel 4026. Otherwise, the surgeon may continue to try and pull the ligament graft 3000' through the passing channel 4026 even though the passing channel 4026 is not generally configured to have a ligament graft disposed therein. Trying to pull the ligament graft 3000' into the passing channel 4026 can cause undesirable harm to the implant 10, the ligament graft 3000', and/or the knee 4000.

Figure 18F:
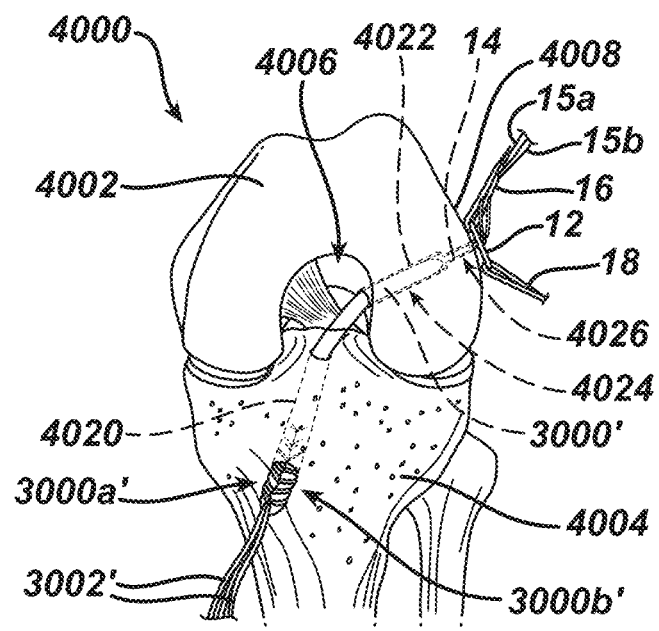

The indicators 3000d' on the ligament graft 3000', however, can remedy the problem of not knowing when the ligament graft 3000' is directly adjacent to the passing channel 4026. Again using the endoscope or other viewing device disposed in the joint space 4006, the surgeon can view the entrance to the main channel 4024 to observe a location of the indicators 3000d' with respect to the main channel 4024. When the 3000d' are no long visible in the joint space 4006 because they are disposed in the main channel 4024, the surgeon knows that the ligament graft 3000' is located directly adjacent to the passing channel 4026 because the location of the indicators 3000d' is representative of the length of the main channel 4024. The surgeon thus knows that the ligament graft 3000' does not need to be pulled any further through the femoral tunnel 4022, otherwise it may be undesirably pulled into the passing channel 4026. The configuration that results from the body 12 being disposed on the femoral cortex 4008 and the ligament graft 3000' being disposed directly adjacent to the passing channel 4026 is illustrated in FIG. 18F.

Once the implant 10 and ligament graft 3000' are secure, the knee 4000 can be cycled as desired to remove excess laxity from the system. Subsequently, the adjustable limbs 15a, 15b can be re-tensioned to insure the desired location of the ligament graft 3000'. Tibial fixation can then be commenced, using techniques known to those skilled in the art. Further, the adjustable limbs 15a, 15b can be trimmed so that there are not excess limbs disposed at the surgical site. The limbs 15a, 15b should generally be trimmed in a manner that does not sacrifice the integrity of the loops 14 and their connection to the implant body 12, which is aided by the limbs 15a, 15b being disposed in the receiving portions 17a, 17b of the leading suture 16. Further, both the leading and trailing sutures 16, 18 can be disassociated from the implant body 12 after the body is desirably positioned. They can be removed either by pulling them out or by cutting and pulling them out, depending on the manner in which they are initially associated with the implant body 12.

MPFL Repair

Figure 19A:
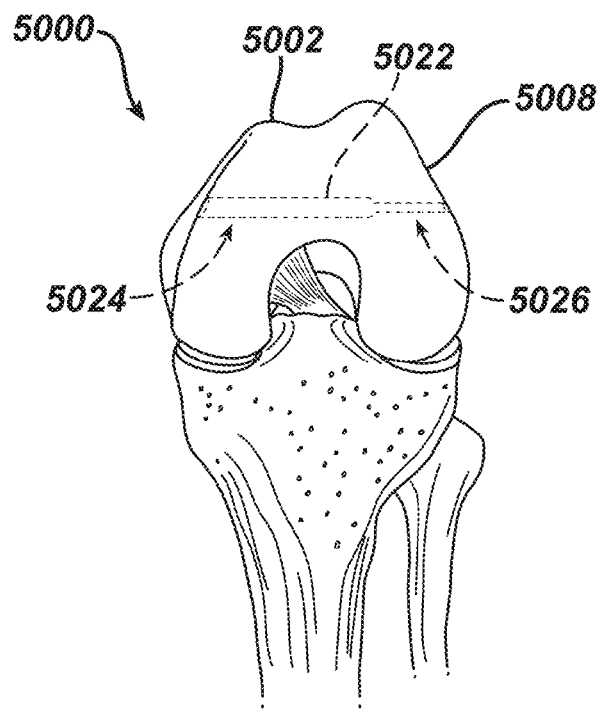
FIG. 19A is a schematic view of one exemplary embodiment of a knee having a femoral tunnel formed therein, the tunnel being configured to receive the ligament graft of FIG. 17B using the implant of FIG. 15S.
Figure 19B:
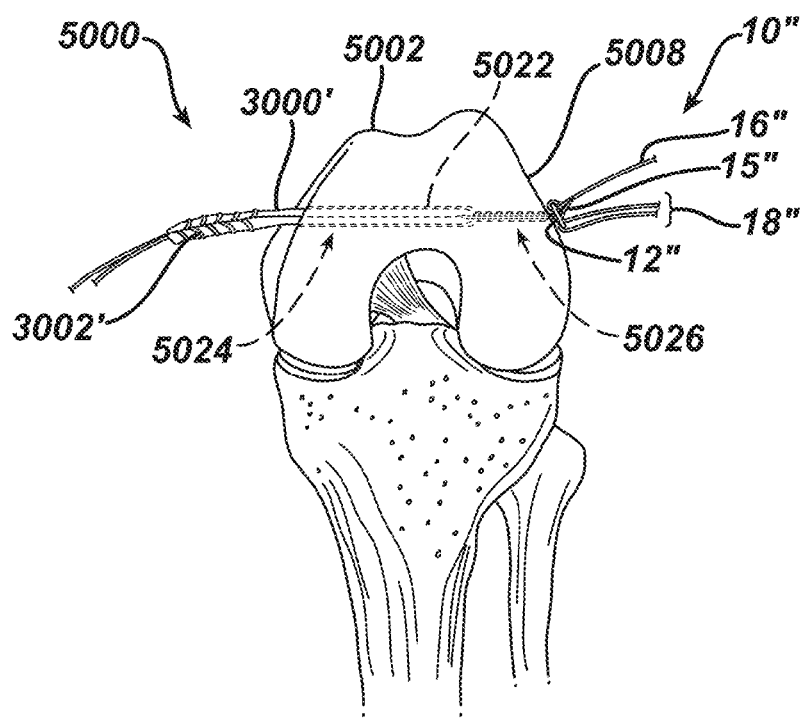
FIG. 19B is a schematic view of the knee of FIG. 19A having the ligament graft of FIG. 17B and an implant associated therewith.

FIGS. 19A and 19B illustrate portions of an MPFL repair procedure that can be performed in view of the disclosures provided for herein. As shown in FIG. 19A, a femoral bone tunnel 5022 can be formed in the femur 5002, with the tunnel 5022 including both a main channel 5024 and a passing channel 5026, the passing channel 5026 having a smaller diameter than the main channel 5024. An implant, implant management device, and ligament graft can be prepared in manners as described earlier, and they can be inserted into the tunnel 5022 using techniques described herein or otherwise known to those skilled in the art. In one exemplary embodiment, an implant 10" and ligament graft 3000' are passed into, and for some portions thereof, through the main channel 5024 and the passing channel 5026 using techniques described with respect to FIGS. 18A-18F. The implant 10" can have previously been associated with any of the embodiments of a surgical implant management device as described herein or derivable therefrom, including the device 900.

A configuration that results during a portion of the procedure described above with respect to FIGS. 18A-18F is provided in FIG. 19B, in which a body 12" of the implant 10" rests against the femoral cortex 5008, adjacent to an opening in the passing channel 5026, the loops 14" being disposed substantially in the passing channel 5026, and the graft 3000' being disposed in the main channel 5024. As shown, the free limbs of suture 3002' are associated with the graft 3000' on one side of the knee 5000, and a limbs 15" and sutures 16", 18" are associated with the implant body 12" on the other side of the knee 4000, although at least any of the free limbs of suture 3002' and sutures 16", 18" can be disassociated with the respective graft 3000' and implant body 12" to complete the implant procedure. In the illustrated embodiment, the implant 10" includes a single adjustable limb 15" associated with the loops 14" to adjust a diameter of the loops 14", the leading suture 16" includes a single limb extending from the body 12" to help guide the body 12" through the femoral tunnel 5022, and the trailing suture 18" includes two limbs to also assist in guiding and placing the body 12" during the procedure. Thus, this implant 10" represents another, non-limiting example of an implant for use in conjunction with the disclosures herein. In the illustrated embodiment, the adjustable limb 15" and leading suture 16" can be disassociated from the body 12" by cutting or trimming them to a desired length, and the trailing suture 18" can be disassociated with the body 12" entirely. In other embodiments, the leading suture 16" can also be completely disassociated from the body 12" and/or the trailing suture 18" can also include a single limb.

The ACL and MPFL repair methods provided for herein are just two examples of surgical procedures that can be performed using the implant management device 900 and implant 10 provided for herein. A person skilled in the art will recognize a variety of other surgical procedures, including variations on cruciate and collateral ligament repairs, with which the implant management device 900 and/or the implant 10, and the other implant management devices and implants provided for herein or otherwise known to those skilled in the art, can be used without departing from the spirit of the present disclosure. Some, non-limiting exemplary embodiments of methods for using implants of the nature provided for herein are disclosed in U.S. patent application Ser. No. 13/793,514 and U.S. patent application Ser. No. 14/103,167, the contents of each which have already been incorporated by reference in their entireties.

Still further, a person skilled in the art will recognize that many other approaches can be taken for making particular markings or indicators on any of the implant management device, implant, and ligament graft without departing from the spirit of the present disclosure. By way of non-limiting example, instead of the indicators on the ligament graft being made such that their disappearance from view indicates that the ligament graft has reached the desired location, the indicators can instead be configured such that their appearance into a view indicates that the ligament graft has reached the desired location. In such an instance, rather than marking the depth of the main channel on the ligament graft, instead the depth of the main channel plus the distance extending between the femoral tunnel and the tibial tunnel can be marked on the ligament graft. Then, once the indicators exit the tibial tunnel and are visible in the joint space, the surgeon will know that the ligament graft is at the desired location. In still further embodiments, the indicators can be made such that they are still indicative of desired locations, but are visible outside of the knee, and thus not in the joint space. A variety of other indicator configurations can be derived from the disclosures provided for herein without departing from the spirit of the present disclosure.

One skilled in the art will appreciate further features and advantages of the invention based on the above-described embodiments. Accordingly, the invention is not to be limited by what has been particularly shown and described, except as indicated by the appended claims. For example, although the embodiments of an implant management device provided for herein are configured for use with an implant having a cortical button, the various devices, and features thereof, can be adapted for use with other types of implants, such as all different types of suture anchors. Likewise, the present disclosure provides a few variations of a particular feature, e.g., an implantable body retainer, but a person skilled in the art will recognize other configurations that can achieve similar results. Thus, by way of non-limiting example, other configurations for maintaining a location of an implant body on a device, e.g., sutures to hold the body on the device, can be utilized without departing from the spirit of the present disclosure. Still further, while various features described herein are provided for at particular locations, a person skilled in the art will recognize that in many instances those features can be located elsewhere on the device without negatively impacting the performance of the device. For example, some of the slits and bores used for filament retention can be disposed in alternate locations. All publications and references cited herein are expressly incorporated herein by reference in their entirety.

What is claimed is:

1. A method for preparing a ligament graft for implantation, comprising:
    positioning a ligament graft through a graft-receiving opening of an implant management card, the implant management card having disposed thereon an implantable body having one or more filament loops associated therewith, at least a portion of the graft-receiving opening being disposed within a loop opening of at least one loop of the one or more filament loops;
    applying tension to the ligament graft; and
    marking a first depth on at least one loop of the one or more filament loops, wherein indicia for use in marking the first depth are provided for on a first surface of the implant management card.

2. The method of claim 1, further comprising decoupling the implantable body and the one or more filament loops associated therewith from the implant management card.

3. The method of claim 1, further comprising marking a second depth on the ligament graft, wherein indicia for use in marking the second depth are provided for on a second, opposed surface of the implant management card.

4. The method of claim 3, further comprising unfolding the implant management card to reveal the indicia for use in marking the second depth.

5. The method of claim 3, wherein the second depth marked is indicative of a graft-in-tunnel depth.

6. The method of claim 1, wherein the first depth marked is indicative of a total bone stock depth.

7. The method of claim 1, wherein applying tension to the ligament graft further comprises:
 positioning a post of a graft preparation board in an alignment opening of the implant management card; and
 moving the ligament graft away from the post to apply tension to the ligament graft.

* * * * *